US010900931B2

(12) United States Patent
Merrill et al.

(10) Patent No.: US 10,900,931 B2
(45) Date of Patent: Jan. 26, 2021

(54) CONTINUOUS FLOW FLUID CONTAMINANT SENSING SYSTEM AND METHOD

(71) Applicant: Quansor Corporation, Sault Ste. Marie, MI (US)

(72) Inventors: John H. Merrill, Grand Marais, MI (US); Alex A. Waldrop, III, South Portland, ME (US); Eric R. Becks, Cheboygan, MI (US)

(73) Assignee: Quansor Corp, Edgarton, WI (US)

( * ) Notice: Subject to any disclaimer, the term of this patent is extended or adjusted under 35 U.S.C. 154(b) by 412 days.

(21) Appl. No.: 15/767,486

(22) PCT Filed: Oct. 14, 2016

(86) PCT No.: PCT/US2016/057239
§ 371 (c)(1),
(2) Date: Apr. 11, 2018

(87) PCT Pub. No.: WO2017/066721
PCT Pub. Date: Apr. 20, 2017

(65) Prior Publication Data
US 2018/0299410 A1 Oct. 18, 2018

Related U.S. Application Data

(60) Provisional application No. 62/241,196, filed on Oct. 14, 2015.

(51) Int. Cl.
G01N 29/036 (2006.01)
G01N 29/30 (2006.01)
G01N 29/44 (2006.01)
G01N 33/18 (2006.01)
G01N 5/02 (2006.01)
G01N 29/00 (2006.01)
H03B 5/36 (2006.01)

(52) U.S. Cl.
CPC ............ G01N 29/036 (2013.01); G01N 5/02 (2013.01); G01N 29/00 (2013.01); G01N 29/30 (2013.01);
(Continued)

(58) Field of Classification Search
USPC ...................................... 73/61, 42
See application file for complete search history.

(56) References Cited

U.S. PATENT DOCUMENTS 5,271,837 A * 12/1993 Discepolo ................ B01J 39/04
210/282
5,614,830 A * 3/1997 Dickert .............. G01N 15/0656
210/695

(Continued)

Primary Examiner — Peter J Macchiarolo
Assistant Examiner — Mohammed E Keramet-Amircolai

(57) ABSTRACT

A sample fluid (14) is pumped through a first cavity (38) associated with a first piezoelectric resonator (20.1) and pumped through a second cavity (40) associated with a second piezoelectric resonator (20.2). An electrode (26) of the first piezoelectric resonator (20.1) exposed to the sample fluid (14) in the first cavity (38) is coated with an adsorption layer (34.1) that provides for adsorbing a substance (12) to be detected in the sample fluid (14). The adsorbed substance (12) changes the resonant frequency of the first piezoelectric resonator (20.1) relative to that of the second piezoelectric resonator (20.2), wherein a change in the frequency difference therebetween relative to an initial frequency difference is responsive to and provides a measure of the mass of adsorbed substance (12). The adsorption layer (34.1) of the first piezoelectric resonator (20.1) is automatically refreshed when a change in the frequency difference crosses a threshold ($\Delta F_{EOR}$).

69 Claims, 34 Drawing Sheets

(52) U.S. Cl.
CPC ..... G01N 29/4436 (2013.01); G01N 33/1826 (2013.01); H03B 5/364 (2013.01); *G01N 2291/014* (2013.01); *G01N 2291/0255* (2013.01); *G01N 2291/0256* (2013.01); *G01N 2291/02809* (2013.01); *G01N 2291/0426* (2013.01)

(56) References Cited

U.S. PATENT DOCUMENTS

| | | | |
|---|---|---|---|
| 6,928,861 B1* | 8/2005 | Rice | G01N 15/04 324/71.4 |
| 8,210,027 B2 | 7/2012 | Goel | |
| 9,086,338 B2* | 7/2015 | Shinobu | G01N 5/02 |
| 10,278,617 B1* | 5/2019 | Satterfield | G01N 33/497 |
| 2001/0054305 A1* | 12/2001 | Banda | G01N 29/28 73/24.01 |
| 2004/0050147 A1* | 3/2004 | Remmlinger | G01N 27/72 73/53.07 |
| 2006/0091763 A1* | 5/2006 | Yoshimine | H03B 5/32 310/311 |
| 2006/0133952 A1* | 6/2006 | Zhang | B82Y 15/00 422/400 |
| 2010/0229656 A1* | 9/2010 | Johnson | B01L 3/5027 73/863.11 |
| 2011/0248700 A1* | 10/2011 | Huber | G01N 29/022 324/109 |
| 2012/0304776 A1 | 12/2012 | Novotny | |
| 2020/0176291 A1* | 6/2020 | Rinzan | G01N 29/036 |

* cited by examiner

CONTINUOUS FLOW FLUID CONTAMINANT SENSING SYSTEM AND METHOD

CROSS-REFERENCE TO RELATED APPLICATIONS

The instant application claims the benefit of prior U.S. Provisional Application Ser. No. 62/241,196 filed on 14 Oct. 2015.

BRIEF DESCRIPTION OF THE DRAWINGS

In the accompanying drawings:

FIG. 4 illustrates and exploded view of a sensor cell assembly of a fluid contaminant sensing system incorporating the pair of quartz-crystal resonators illustrated in FIG. 3a;

DESCRIPTION OF THE EMBODIMENT(S)

Figure 1A:
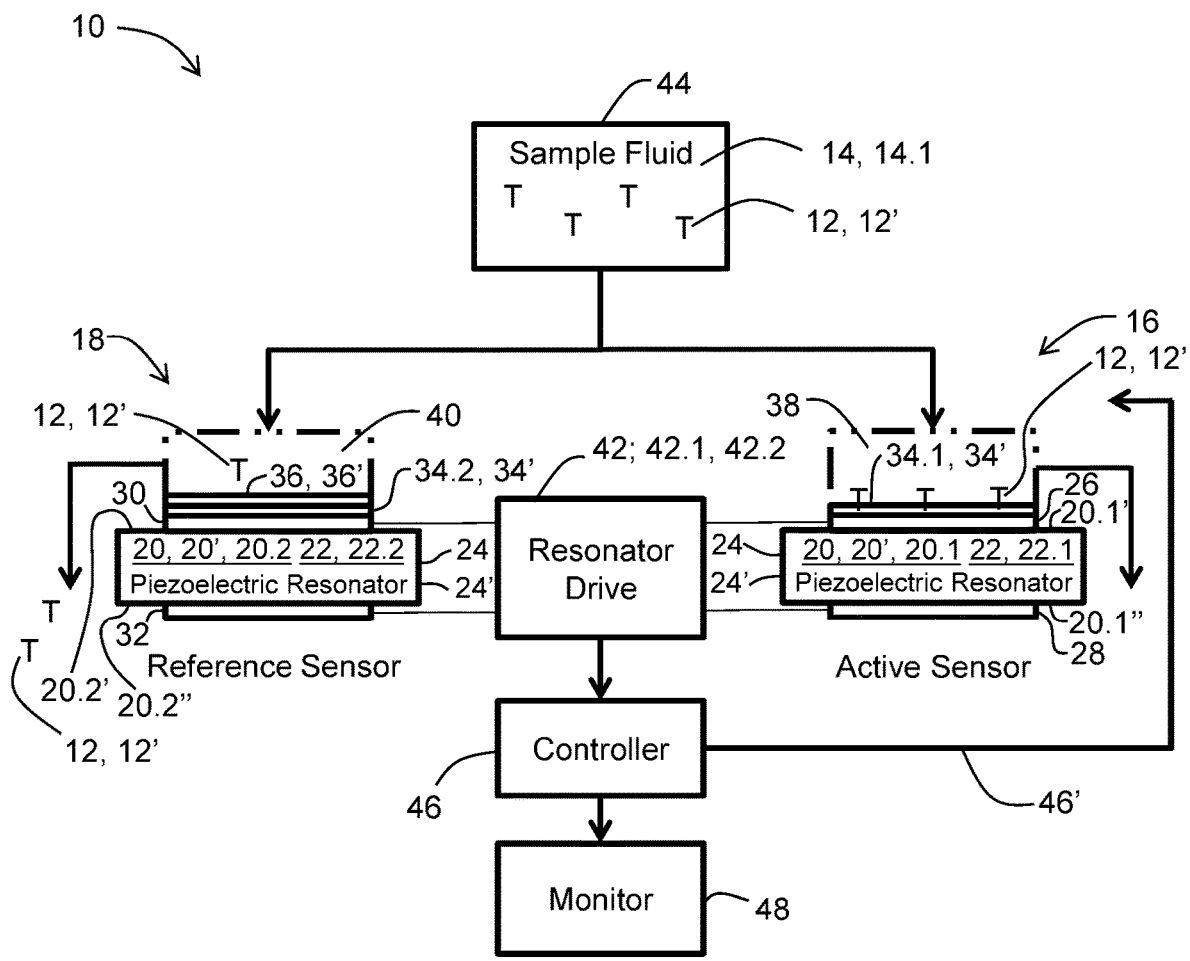
FIG. 1a illustrates a fluid contaminant sensing system comprising active and reference sensors, under normal operation.

Referring to FIG. 1a, a fluid contaminant sensing system 10 provides for continuously sensing an adsorbable substance 12—also referred to as a target analyte 12—in a sample fluid 14, for example, for sensing a contaminant 12' in a stream of water 14.1 by measuring the resonant frequency of an associated miniature piezoelectric resonator, wherein the adsorption of the adsorbable substance 12 on a surface of the miniature piezoelectric resonator causes the mass of the miniature piezoelectric resonator to increase, which causes the resonant frequency thereof to decrease, so as to provide for measuring the moles, mass or weight of the adsorbable substance 12 responsive to the affect thereof on the resonant frequency. The fluid contaminant sensing system 10 incorporates an active sensor 16 and a reference sensor 18, each of which sample, and are exposed to, the sample fluid 14, and each of which incorporate a corresponding associated piezoelectric resonator 20, for example a quartz-crystal resonator 20', comprising either a continuous piezoelectric wafer 22, or separate active 22.1 and reference 22.1 piezoelectric wafers, of associated piezoelectric 24, or quartz-crystal 24' material. More particularly, the active sensor 16 incorporates an associated active piezoelectric resonator 20.1 comprising an underlying piezoelectric wafer 22, 22.1 of piezoelectric material 24 that incorporates first 26 and second 28 electrodes on—e.g. deposited on, e.g. by sputtering, or bonded to—corresponding first 20.1' and second 20.1" surfaces thereof. Similarly, the reference sensor 18 incorporates an associated reference piezoelectric resonator 20.2 comprising an underlying piezoelectric wafer 22, 22.2 of piezoelectric material 24 that incorporates third 30 and fourth 32 electrodes on—e.g. deposited on, e.g. by sputtering, or bonded to—corresponding third 20.2' and fourth 20.2" surfaces thereof.

The first electrode 26 of the active sensor 16 and the third electrode 30 of the reference sensor 18 are each respectively coated with an adsorption layer 34.1, 34.2 of adsorption material 34' that—absent any further modification thereof—provides for preferentially adsorbing the adsorbable substance 12 when the adsorbable substance 12 comes into contact with the adsorption material 34'. The adsorption layer 34.2 of the reference sensor 18 is either further coated with a blocking layer 36 of an associated blocking substance 36', or treated with the blocking substance 36', wherein the blocking substance 36' binds to the adsorption binding sites of the associated adsorption material 34' of the associated adsorption layer 34.2 of the reference sensor 18 so as to prevent any subsequent adsorption of an adsorbable substance 12 that might be contained in the sample fluid 14 when exposed thereto.

The active sensor 16 incorporates a first cavity 38 adjacent to and bounded in part by the adsorption layer 34.1 of the first electrode 26. Similarly, the reference sensor 18 incorporates a second cavity 40 adjacent to and bounded in part by the blocking layer 36 of the third electrode 30. The sample fluid 14 is pumped through both the first 38 and second 40 cavities at approximately the same rates, wherein the flow rate through the first cavity 38 is either predetermined (for example, by using an associated positive displacement pump) or measured, so as to provide for determining the total volume of sample fluid 14 that flows through the first cavity 38 and is subject to sensing by the active sensor 16. The flow rate of the sample fluid 14 may be corrected for temperature by also measuring the temperature thereof.

The active 20.1 and reference 20.2 piezoelectric resonators are resonated by at least one associated resonator drive circuit 42, each comprising an associated oscillator, the frequency of which is inherently controlled by the associated active 20.1 or reference 20.2 piezoelectric resonator to which the oscillator is connected. In one embodiment, as resonator drive circuit 42 is shared between the active 20.1 and reference 20.2 piezoelectric resonators, and is alternately repetitively switched therebetween, so as to drive each of the active 20.1 and reference 20.2 piezoelectric resonators at alternate, mutually-exclusive intervals of time. In another embodiment, a separate, distinct resonator drive circuit 42.1, 42.2 is associated with each of the active 20.1 and reference 20.2 piezoelectric resonators, wherein the resonator drive circuits 42.1, 42.2 are either alternately activated or coupled, and deactivated or decoupled, during alternate period of times, particularly for embodiments for which the active 20.1 and reference 20.2 piezoelectric resonators comprise different portions of a single continuous piece of associated piezoelectric material 24; or simultaneously activated and coupled to the active 20.1 and reference 20.2 piezoelectric resonators, respectively, for example, for embodiments for which the active 20.1 and reference 20.2 piezoelectric resonators comprise different distinct pieces of piezoelectric material 24.

The resonant frequency of the each of the active 20.1 and reference 20.2 piezoelectric resonators is dependent primarily upon the respective masses thereof, but can also be affected by the temperature, density and viscosity of the associated sample fluid 14 within the first 38 and second 40 cavities. Following initial manufacture, the masses of the underlying associated portions of either the associated continuous piezoelectric wafer 22, or the corresponding separate active 22.1 and reference 22.1 piezoelectric wafers, and the corresponding pairs of first 26 and second 28 electrodes and third 30 and fourth 32 electrodes, together with the associated adsorption layers 34.1, 34.2, would typically be substantially the same, so as to provide for the active 20.1 and reference 20.2 piezoelectric resonators to have substantially the same nominal resonant frequency prior to introduction of the blocking layer 36 to the reference piezoelectric resonator 20.2, the latter of which acts to increase the mass thereof and lower the corresponding resonant frequency relative to that of the virgin active piezoelectric resonator 20.1. As the sample fluid 14 containing detectable amounts of the adsorbable substance 12 is pumped through the first 38 and second 40 cavities, the flow through the first cavity 38 so as to provide sufficient residence time therewithin for the adsorbable substance 12 therewithin to become adsorbed by the adsorption layer 34.1 on the first electrode 26 of the active sensor 16, thereby increasing the mass thereof, and as a result, decreasing the associated resonant frequency of the active piezoelectric resonator 20.1. If either the active 16 or reference 18 sensor was constructed as a corresponding quartz-crystal resonator 20', this would be commonly referred to as a quartz-crystal microbalance (QCM), which provides for measuring the moles, mass or weight of a substance adsorbed on the quart-crystal resonator 20' thereof, responsive to a change in the resonant frequency thereof.

The change in resonant frequency of an AT-cut quartz-crystal resonator 20' as a result of an accumulation of mass thereon can be characterized by what is known as the Sauerbrey equation, which treats the mass that is adsorbed by or deposited on the quartz-crystal resonator 20' as an extension of the thickness of the underlying quartz-crystal material 24', and which, for a quartz-crystal resonator 20' exposed to air, is given by:

$$\Delta f = \frac{2 \cdot f_0^2}{A \cdot \sqrt{\rho_q \cdot \mu_q}} \cdot \Delta m \qquad (1)$$

assuming that the adsorbed or deposited mass is rigid and evenly-distributed, and assuming that the relative change of frequency, i.e. $\Delta f/f_0$, is less than 2%, wherein $\Delta f$ is the change in resonant frequency (Hz) of the quartz-crystal resonator 20' as a result of a $\Delta m$ change of mass (g) thereof $f_0$ is the nominal resonant frequency (Hz) of the quartz-crystal resonator 20' prior to the change of mass thereof; A is pizoelectrically active area (cm$^2$) of the quartz-crystal material 24' of the quartz-crystal resonator 20' between the first 26 and second 28 electrodes, or between the third 30 and fourth 32 electrodes; $\rho_q$ is the density of the quartz-crystal material 24' ($\rho_q$=2.648 g/cm$^3$); and $\mu_q$ is the shear modulus of the quartz-crystal material 24' for an AT-cut crystal ($\mu_q$=2.947×10$^{-11}$ g·cm$^{-1}$·s$^{-2}$). The change of frequency $\Delta f$ given by equation (1) is substantially independent of the associated electrode geometry.

If the relative change of frequency is greater than 2%, the change in mass $\Delta m$ of the quartz-crystal material 24' of the quartz-crystal resonator 20' can be determined by what is known as the Z-match method using the following equation $$\frac{\Delta m}{A} = \frac{N_q \cdot \rho_q}{\pi \cdot Z \cdot f_L} \cdot \tan^{-1}\left[Z \cdot \tan\left(\pi \cdot \frac{f_0 - f_L}{f_0}\right)\right] \qquad (2)$$

wherein $f_L$ is the frequency (Hz) of the mass-loaded quartz-crystal resonator 20'; $N_q$ is a frequency constant for an AT-cut crystal ($N_q$=1.668×10$^{-13}$ Hz·Å), and $$Z = \left(\frac{\rho_q \cdot \mu_q}{\rho_f \cdot \mu_f}\right)^{\frac{1}{2}} \qquad (3)$$

wherein $\rho_f$ is the density (g/cm$^3$) of the adsorbed or deposited mass, and $\mu_f$ is the shear modulus (g·cm$^{-1}$·s$^{-2}$) of the adsorbed or deposited mass.

For operation of the quartz-crystal resonator 20' in a liquid—as is the case for the active 20.1 and reference 20.2 piezoelectric resonators —, the change in resonant frequency of the quartz-crystal resonator 20' as a result of the viscosity of the liquid in contact with the quartz-crystal resonator 20', i.e. the sample fluid 14, is given by:

$$\Delta f = -f_0^{\frac{3}{2}} \cdot \left(\frac{\eta_l \cdot \rho_l}{\pi \cdot \rho_q \cdot \mu_q}\right)^{\frac{1}{2}} \qquad (4)$$

wherein $\rho_l$ is the density of the liquid in contact with the quartz-crystal resonator 20', and $\eta_l$ is the viscosity of the liquid in contact with the quartz-crystal resonator 20'. This viscosity- and density-dependent change in frequency, as well an associated temperature-dependent change in frequency—in addition to the effect of the mass of the adsorbable substance 12 or target analyte 12 on the change $\Delta f$ in resonant frequency—is inherently compensated for by simultaneously measuring the resonant frequencies of the active 20.1 and reference 20.2 piezoelectric resonators with each exposed to a different sample of the same sample fluid 14, and using the frequency difference therebetween to provide a measure of the change of mass of the active piezoelectric resonator 20.1, because the resonant frequencies of both the active 20.1 and reference 20.2 piezoelectric resonators would be similarly perturbed by the effect of temperature, density and viscosity, and the effect of the associated perturbation of each would be cancelled by the differencing of the associated separate resonant frequencies. Similarly, the resonant frequencies of each of the active 20.1 and reference 20.2 piezoelectric resonators can each be affected—and jointly affected—by other artifacts such as vibrations; chemical properties, including ionic strength of, and pH changes in, the sample fluid 14 can elicit or affect an associated frequency response in both the active 20.1 and reference 20.2 piezoelectric resonators that would be inherently compensated for by frequency differencing. Furthermore, the ionic strength of, and pH changes in, the sample fluid 14 can affect the mass of the associated adsorption layer 34.1, 34.2 in both the active 20.1 and reference 20.2 piezoelectric resonators, which in turn elicits associated frequency responses therein that would be inherently compensated for by frequency differencing.

With the sample fluid 14 split and pumped at substantially the same flow rate through both the first 38 and second 40 cavities, both the active 20.1 and reference 20.2 piezoelectric resonators will experience substantially the same effects of temperature, density and viscosity of the sample fluid 14 on the associated resonant frequencies of thereof, so that the difference in resonant frequencies of the active 20.1 and reference 20.2 piezoelectric resonators—referred to as the frequency difference of the active 20.1 and reference 20.2 piezoelectric resonators—will be substantially responsive to the difference in mass thereof. The active 20.1 and reference 20.2 piezoelectric resonators are calibrated to provide a relationship—either tabular or functional—between frequency difference and the corresponding mass or moles of adsorbable substance 12 adsorbed on the adsorption layer 34.1 of the active piezoelectric resonator 20.1, which together with the separately determined total moles, volume or mass of sample fluid 14, can then be used to continuously determine a concentration of the adsorbable substance 12 in the sample fluid 14.

For example, FIG. 1a illustrates a point in time for which four quanta of adsorbable substance 12 are in the source 44 of sample fluid 14, with three quanta of adsorbable substance 12 having been pumped into each of the first 38 and second 40 cavities, which all three of the quanta of adsorbable substance 12 pumped into the first cavity 38 having been adsorbed by the adsorption layer 34.1 of the active piezoelectric resonator 20.1, with two of the three quanta of adsorbable substance 12 pumped into the second cavity 40 having been discharged therefrom, and with the remaining quantum of adsorbable substance 12 pumped into the second cavity 40 awaiting discharge therefrom, and not otherwise contributing to the mass of the reference piezoelectric resonator 20.2.

A controller 46 operatively coupled to the at least one associated resonator drive circuit 42 determines the frequency difference—i.e. the amount by which the resonant frequency of the reference piezoelectric resonator 20.2 exceeds that of the active piezoelectric resonator 20.1—between the active 20.1 and reference 20.2 piezoelectric resonator, and determines the concentration of the adsorbable substance 12 in the sample fluid 14 for display on, or transfer to, an associated display 48 either incorporated with, or remotely located with respect to, the fluid contaminant sensing system 10.

Figure 1B:
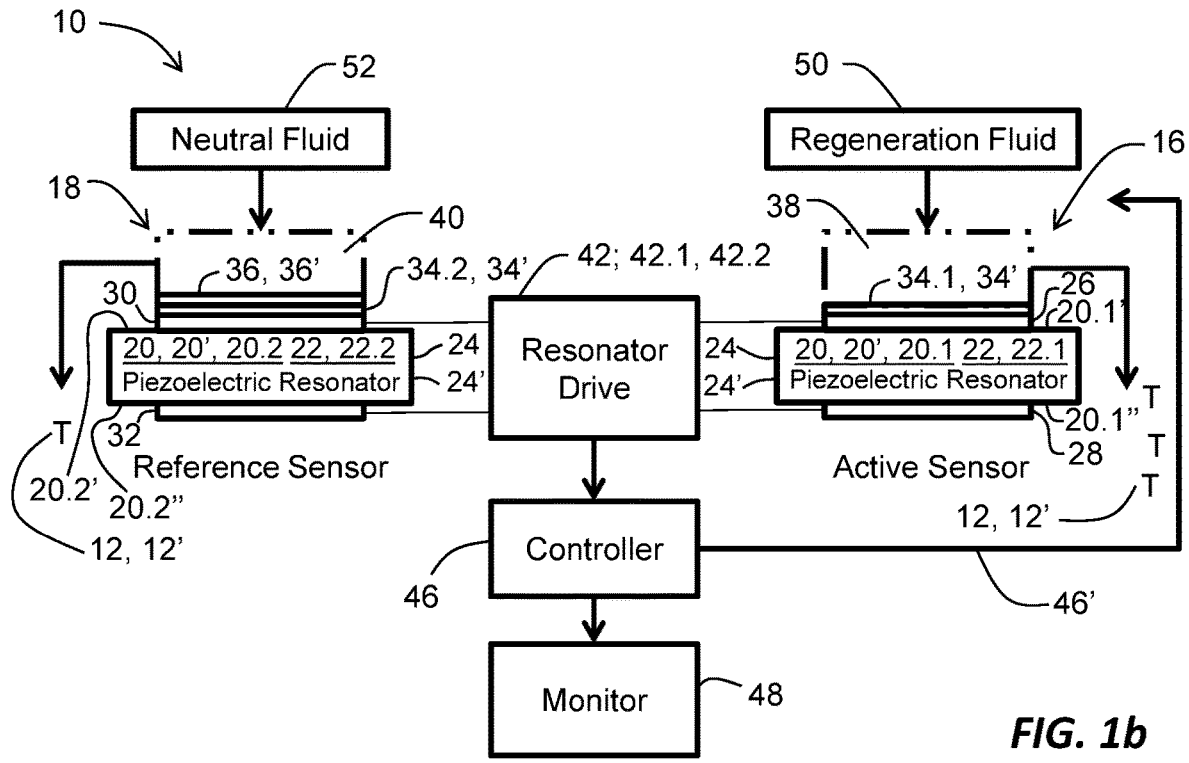
FIG. 1b illustrates the fluid contaminant sensing system of FIG. 1a during an associated operation to refresh the associated active sensor.

Referring to FIG. 1b, if the frequency difference exceeds a corresponding first threshold—indicating that the mass of the active piezoelectric resonator 20.1 is in excess of an effective operating range, then, responsive to one or more control signals 46' from the controller 46, the active piezoelectric resonator 20.1 is refreshed with an associated refresh process by pumping a regeneration fluid 50 through the first cavity 38, which selectively removes the adsorbable substance 12 adsorbed on the adsorption layer 34.1 of the active piezoelectric resonator 20.1, thereby increasing the associated resonant frequency thereof, which in turn reduces the associated frequency difference between the active 20.1 and reference 20.2 piezoelectric resonator, with the resonant frequency of the reference piezoelectric resonator 20.2 measured while pumping a neutral fluid 52 through the associated second cavity 40.

For example, for the refresh process having commenced with the fluid contaminant sensing system 10 in the state illustrated in FIG. 1a, FIG. 1b illustrates the remaining quantum of adsorbable substance 12 in the second cavity 40 having been flushed therefrom by the neutral fluid 52, and illustrates the three quanta of adsorbable substance 12 having been dislodged from the adsorption layer 34.1 by the regeneration fluid 50 and discharged therewith from the first cavity 38.

Figure 1C:
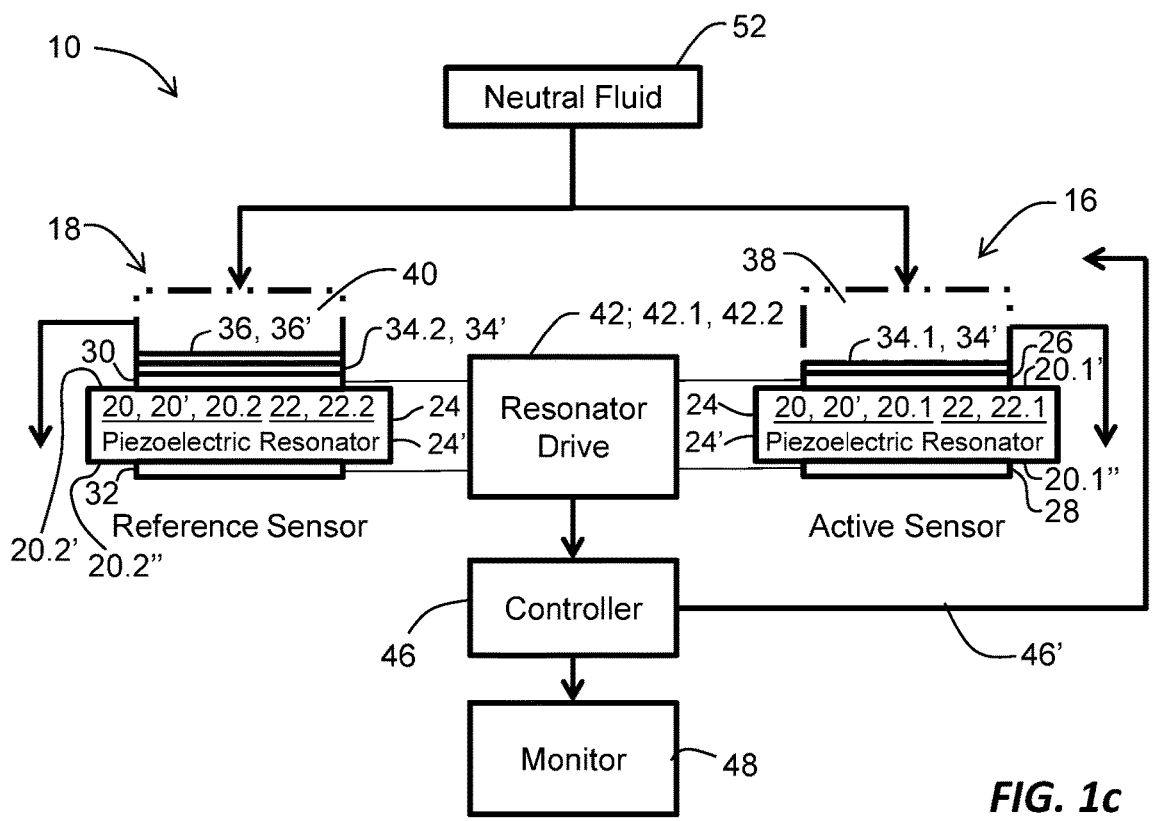
FIG. 1c illustrates the fluid contaminant sensing system of FIGS. 1a and 1b during an associated operation to rinse the associated active sensor prior to resuming normal operation.

Referring to FIG. 1c, after the frequency difference is reduced to less than the second threshold, responsive to one or more control signals 46' from the controller 46, the fluid contaminant sensing system 10 may commence a rinse process to clear the regeneration fluid 50 from the first cavity 38, wherein the neutral fluid 52 is pumped through both the first 38 and second 40 cavities until the frequency difference stabilizes over time, after which the fluid contaminant sensing system 10 resumes normal operation of sampling and measuring the sample fluid 14, as illustrated in FIG. 1a.

Figure 2:
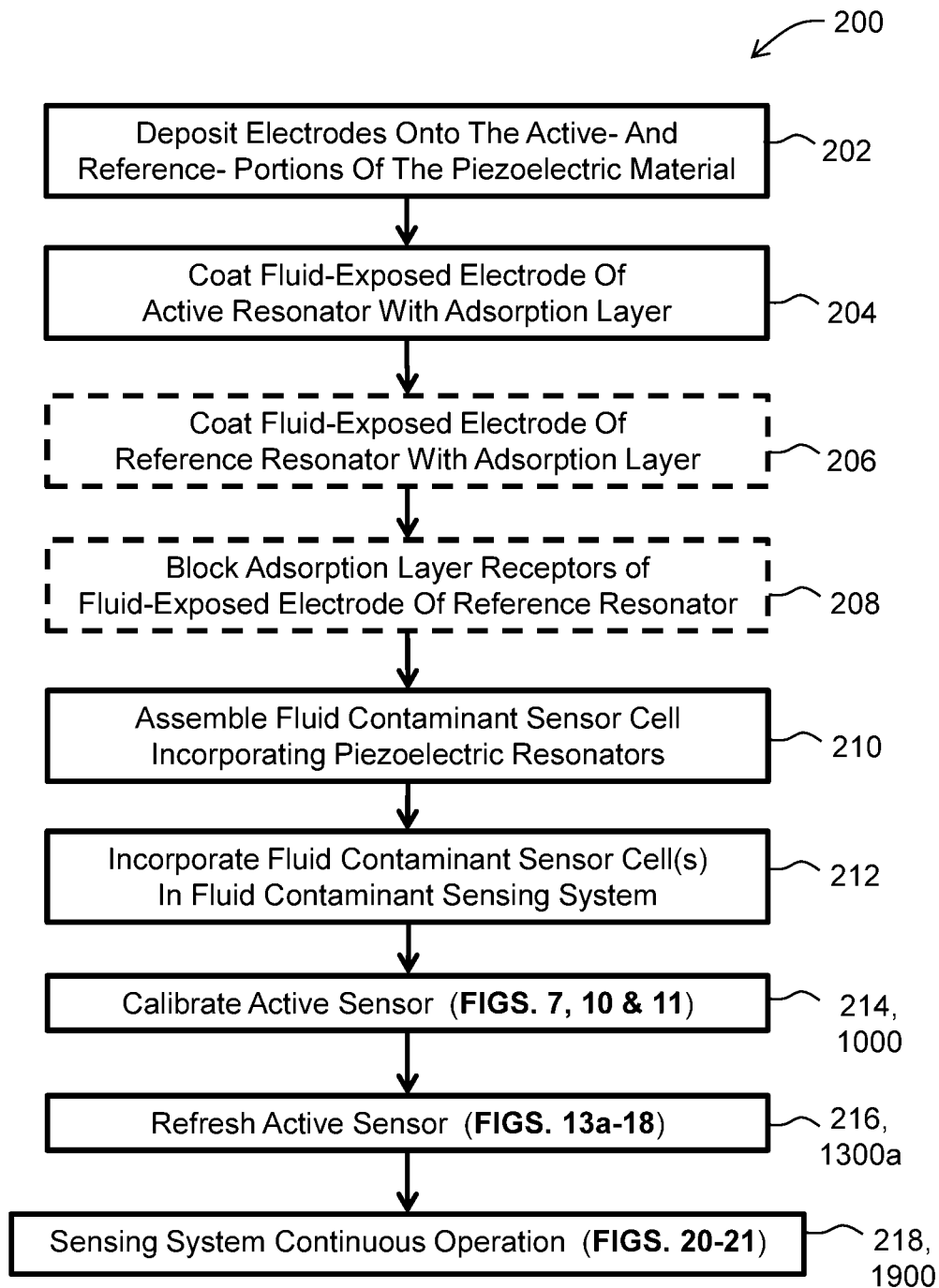
FIG. 2 illustrates a process for preparing and using the active and reference sensors of the fluid contaminant sensing system illustrated in FIGS. 1a through 1c.

Referring to FIG. 2, the active 20.1 and reference 20.2 piezoelectric resonators are made and used in accordance with a process 200, and a first embodiment of an associated fluid contaminant sensor cell 54 made in accordance therewith is illustrated in FIGS. 3a-6b, wherein each of the associated active 20.1 and reference 20.2 piezoelectric resonators are constructed as a corresponding quartz-crystal microbalance (QCM) 56.1, 56.2 on different, distinct portions of a continuous piezoelectric wafer 22 of quartz-crystal material 24', i.e. comprising a single quartz crystal 24' so as to provide for the active 20.1 and reference 20.2 piezoelectric resonators to have substantially the same associated physical and electrical characteristics. In step (202), and referring to FIG. 3a, the associated first 26 and third 30 electrodes of the active 20.1 and reference 20.2 piezoelectric resonators, respectively, are deposited on first 20.1' and third 20.2' surface portions of a first surface 22' of the continuous piezoelectric wafer 22, and the associated second 28 and fourth 32 electrodes of the active 20.1 and reference 20.2 piezoelectric resonators, respectively, are deposited on second 20.1" and fourth 20.2" surface portions of a second surface 22" of the continuous piezoelectric wafer 22, wherein the first 20.1' and second 20.1" surface portions of the active piezoelectric resonator 20.1 are directly opposed to one another across the continuous piezoelectric wafer 22 at a first location 58 on the continuous piezoelectric wafer 22, and the third 20.2' and fourth 20.2" surface portions of the reference piezoelectric resonator 20.2 are directly opposed to one another across the continuous piezoelectric wafer 22 at a second location 60 on the continuous piezoelectric wafer 22, with the first 58 and second 60 locations being sufficiently separated from one another so as to provide for the active 20.1 and reference 20.2 piezoelectric resonators to act independently of one another. The first 26 and second 28 electrodes are substantially mirror images of one another, and of a circular shape, although the shape is not limiting. Similarly, the third 30 and fourth 32 electrodes are substantially mirror images of one another, and of a circular shape, although the shape is also not limiting, but the size and shape of the third 30 and fourth 32 electrodes is substantially the same as the size and shape of the first 26 and second 28 electrodes so as to provide for the associated resulting active 20.1 and reference 20.2 piezoelectric resonators to have similar mechanical and electrical properties with substantially the same resonant frequency and substantially the same sensitivities to changes in mass and to the effects of temperature, density, viscosity and other factors that affect the resonant frequency of the associated piezoelectric resonators 20.

For example, for each of the first 26 and third 30 electrodes on the first surface 22' of the piezoelectric wafer 22, corresponding associated respective conductive paths 26.1 and 30.1 are also deposited on the first surface 22' of the piezoelectric wafer 22, each extending from the associated electrode 26, 30 to the periphery 62 of the piezoelectric wafer 22. Similarly, for each of the second 28 and fourth 32 electrodes on the second surface 22" of the piezoelectric wafer 22, corresponding associated respective conductive paths 28.1 and 32.1 are also deposited on the second surface 22" of the piezoelectric wafer 22, each extending from the associated electrode 28, 32 to the periphery 62 of the piezoelectric wafer 22.

The conductive paths 26.1, 28.1 from the first 26 and second 28 electrodes on opposing surfaces 22', 22" of the piezoelectric wafer 22 are misaligned with respect to one another, for example having a relative included angle of approximately 90 degrees, so as to not act to resonate the portion of the piezoelectric wafer 22 therebetween, and to thereby limit the piezoelectric action of the first 26 and second 28 electrodes to the region of the piezoelectric wafer 22 directly therebetween. Similarly, the conductive paths 30.1, 32.1 from the third 30 and fourth 32 electrodes on opposing surfaces 22', 22" of the piezoelectric wafer 22 are misaligned with respect to one another, for example having a relative included angle of approximately 90 degrees, so as to not act to resonate the portion of the piezoelectric wafer 22 therebetween, and to thereby limit the piezoelectric action of the third 30 and fourth 32 electrodes to the region of the piezoelectric wafer 22 directly therebetween, wherein conductive paths 26.1, 28.1 are diametrically opposed with respect to conductive paths 30.1, 32.1 with respect to a plan view of the piezoelectric wafer 22.

For example, in one set of embodiments, the piezoelectric wafer 22 piezoelectric wafer 22 is and AT-cut quartz crystal having a nominal diameter of 0.538 inches (13.67 mm), from International Crystal Manufacturing, and configured to resonate at about 10 MHz—or more generally, in the range of 3 to 50 MHz. The particular diameter is not limiting, nor is the particular resonant frequency, although the resolution of the associated mass or mole measurements is finer (i.e. increases) with increasing resonant frequency.

The electrodes 26, 28, 30 and 32 and the associated conductive paths 26.1, 28.1, 30.1 and 32.1 are formed by depositing associated layers of titanium—for example, each having a thickness of about 100 Å—on the first 22' and second 22" surfaces of the piezoelectric wafer 22, and then depositing associated layers of gold—for example, having a thickness of about 1000 Å—on the first 22' and second 22" surfaces of the piezoelectric wafer 22 over the associated titanium layers. For example, the various layers may be deposited by vapor deposition of with heating or sputtering of the material to be deposited.

Figure 6A:
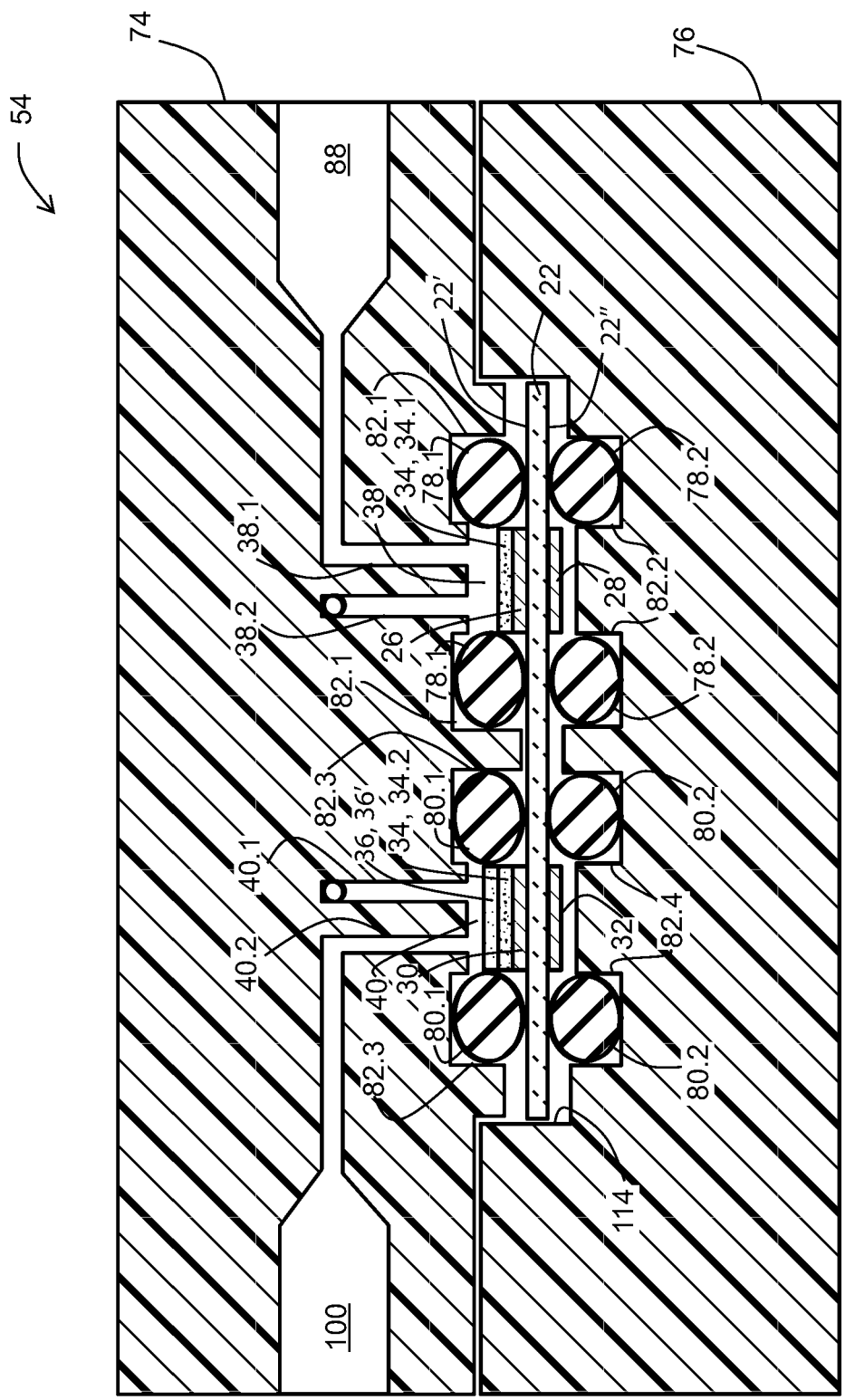
FIG. 6a illustrates a first cross-sectional view the sensor cell assembly of a fluid contaminant sensing system illustrated in FIG. 4—but assembled—with the section taken through associated inlet and outlet ports of the cavities associated with the active and reference sensors.
Figure 6B:
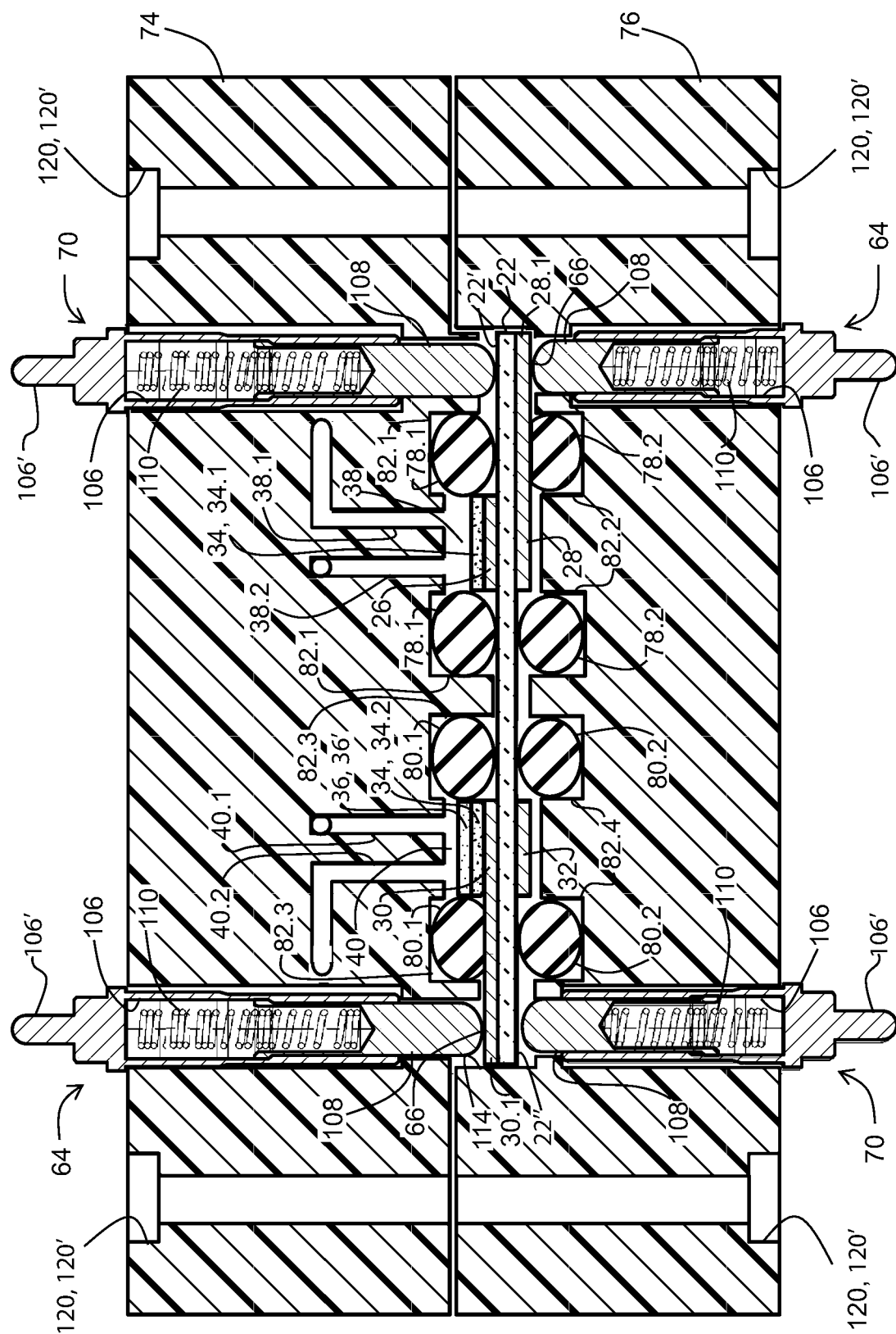
FIG. 6b illustrates a second cross-sectional view the sensor cell assembly of a fluid contaminant sensing system illustrated in FIG. 4—but assembled—with the section taken through associated Pogo-pin-style connections to the pair of quartz-crystal resonators, and through the locations of fasteners used to assemble the associated top and bottom blocks of the sensor cell.

The conductive paths 26.1, 28.1, 30.1 and 32.1 are interconnected to the associated resonator drive circuit 42, 42.1, 42.2 using spring-loaded contact-forming Pogo-pin-style connectors 64—illustrated in FIG. 6b—that provide for biasing an associated contact surface 66—also illustrated in FIG. 6b—against the surface of a corresponding conductive path 26.1, 28.1, 30.1 and 32.1 with a corresponding contact-forming bias force 68. An additional set of force-balancing Pogo-pin-style connectors 70 are provided that are co-linear with the corresponding associated contact-forming Pogo-pin-style connectors 64, but which act from an opposite side of the piezoelectric wafer 22 with corresponding equal, but opposite, force-balancing bias forces 72, so as to provide for preventing associated warping moments from being generated that would otherwise act to distort the piezoelectric wafer 22, for example, if only the contact-forming Pogo-pin-style connectors 64 were present.

When assembled in the fluid contaminant sensor cell 54, the first 26 and third 30 electrodes of the active 20.1 and reference 20.2 piezoelectric resonators are fluid-exposed electrodes during use thereof, whereas the remaining second 28 and fourth 32 electrodes are fluid-isolated electrodes that, for example, are exposed to air. Referring again to FIG. 2, in step (204), the fluid-exposed—i.e. top or outer—surfaces of the first electrode 26 of the active piezoelectric resonator 20.1 is coated—for example, by spin coating—with an adsorption material 34' so as to form the corresponding associated adsorption layer 34.1 on the fluid-exposed surfaces of the first electrode 26 of the active piezoelectric resonator 20.1.

In accordance with one set of embodiments, in step (206), the fluid-exposed—i.e. top or outer—surface of the third electrode 30 of the reference piezoelectric resonator 20.2 is coated—for example, by spin coating—with an adsorption material 34' so as to form the corresponding associated adsorption layer 34.2 on the fluid-exposed surface of the third electrode 30 of the reference piezoelectric resonator 20.2.

The adsorption material 34' comprises one or more types of chemical receptors that can be configured to bind to various types of target analytes 12, for example, an inorganic chemical, compound or element; an organic chemical; or a micro-organism. The adsorption material 34' may be configured either to selectively bind to an individual target analyte 12, for example, copper; or to non-selectively bind to a group of target analytes 12, for example, heavy-metal cations.

In accordance with a first aspect, the adsorption material 34' utilized in steps (204) and (206) of process (200) of FIG. 2 comprises a functionalized polymer that can be used without further modification or can be reacted to attach a variety of other functional groups. In accordance with one set of embodiments, the functionalized polymer is a polyamine, such as polyallylamine (PAH) or poly(L-lysine). Both of these polymers have primary amine groups which can bind anions at pH's where the amine groups are protonated. The primary amine groups can also be modified with appropriate reagents to attach covalently other binding groups. Anhydrides and NHS-esters (N-oxysuccinimide esters) are reagents frequently used to modify accessible amine groups in proteins and other amine-containing polymers. One useful modification is to react the amine groups with an anhydride or an NHS-ester of a polycarboxylic acid chelator such as EDTA (ethylenediaminetetraaceticacid). EDTA can bind many metal ions, especially multivalent ones. If greater affinity for metal ions is desired after coupling the chelating agent to the polyamine, an anhydride of diethylenetriaminepentaacetic acid is one possible alternative reagent to react with the polyamine.

For example, in one set of embodiments to non-selectively bind either lead ($Pb^{2+}$), cadmium ($Cd^{2+}$), or mercuric ion ($Hg^{2+}$) in the sample fluid 14, the polyamine adsorption material 34'—e.g. PAH—of each of the adsorption layers 34.1, 34.2 on the first 26 and third 30 electrodes is reacted with EDTA dianhydride. The associated adsorption layer 34.1 on the first electrode 26, —i.e. of the active piezoelectric resonator 20.1—can be refreshed with a solution of 100 mM HCl as the associated regeneration fluid 50—used in a refresh process described more fully hereinbelow—applied thereto in order to cleanse the adsorption layer 34.1 on the first electrode 26 of associated metal ions, so as to restore the active piezoelectric resonator 20.1 to, or near, its initial, virgin resonant frequency.

Following the formation of the adsorption layer 34.2 on the third 30 electrode of the reference piezoelectric resonator 20.2, in step (208), the chemical receptors thereof are blocked, or immobilized, so as to prevent any target analyte 12 in the sample fluid 14 from being adsorbed thereby during operation of the fluid contaminant sensing system 10. For example, if the target analyte 12 is lead ($Pb^2$), then the adsorption layer 34.2 on the third electrode 30 of the reference piezoelectric resonator 20.2 may be blocked, or immobilized, by saturating the chemical receptors of the associated EDTA groups with ($Pb^{2+}$) ions. As another example, if the target analyte 12 is cadmium ($Cd^{2+}$), then the adsorption layer 34.2 on the third electrode 30 of the reference piezoelectric resonator 20.2 may be blocked, or immobilized, by saturating the chemical receptors of the associated EDTA groups with $Cd^{2+}$ ions. As yet another example, if the target analyte 12 is mercuric ion ($Hg^{2+}$), then the adsorption layer 34.2 on the third electrode 30 of the reference piezoelectric resonator 20.2 may be blocked, or immobilized, by saturating the chemical receptors of the associated EDTA groups with $Hg^{2+}$ ions. In any of these cases, any one of the associated blocking substances 36', i.e. $Pb^{2+}$, $Cd^{2+}$ or $Hg^{2+}$ would be effective against blocking the adsorption of any of the remaining ions because the EDTA groups do not act as exchanger.

In accordance with an alternative, second aspect, the adsorption layer 34.1 on the first electrode 26 of the active piezoelectric resonator 20.1 is the same as described hereinabove for the first aspect but the adsorption layer 34.2 on the third electrode 30 of the reference piezoelectric resonator 20.2 is formed without reacting the polyamine adsorption material 34' with EDTA dianhydride. More particularly, the adsorption material 34' utilized in step (206) of process (200) of FIG. 2 on the third electrode 30 of the reference piezoelectric resonator 20.2 comprises a functionalized polymer that can be used without further modification or can be reacted to attach a variety of other functional groups. In accordance with one set of embodiments, the functionalized polymer is a polyamine, such as polyallylamine (PAH) or poly(L-lysine). Then, in n step (208), the chemical receptors of the adsorption layer 34.2 of the reference piezoelectric resonator 20.2 can be blocked, or immobilized, so as to provide for preventing adsorption thereon of metal ions generally, or the above-described $Pb^{2+}$, $Cd^{2+}$ or $Hg^{2+}$ ions in particular, by treating the third electrode 30 of the reference piezoelectric resonator 20.2—coated with PAH—with acetic acid anhydride, resulting in the adsorption layer 34.2 thereof comprising a polyamide where the amine groups have been reacted to form acetylamides, wherein the acetylamide groups on the resulting polymer (polymer-NH—C(=O)CH3) will have little or no affinity for free metal ions.

In accordance with an alternative third aspect to non-selectively bind arsenite, As(III), in the sample fluid 14, in steps (204) and (206) of process (200) of FIG. 2, the adsorption material 34' of each of the adsorption layers 34.1, 34.2 on the first 26 and third 30 electrodes comprises the above-described PAH, followed by reaction with lanthanum hydroxide (LaOH). The associated adsorption layer 34.1 on the first electrode 26, —i.e. of the active piezoelectric resonator 20.1—can be refreshed with a solution of 100 mM NaOH as the associated regeneration fluid 50—used in a regeneration process described more fully hereinbelow—applied thereto in order to cleanse the adsorption layer 34.1 on the first electrode 26 of associated arsenite, so as to restore the active piezoelectric resonator 20.1 to, or near, its initial, virgin resonant frequency. Following the formation of the adsorption layer 34.2 on the third 30 electrode of the reference piezoelectric resonator 20.2, in step (208), the chemical receptors thereof are blocked, or immobilized, by saturating the chemical receptors thereof with arsenite, As(III) ions.

In accordance with an alternative fourth aspect to selectively bind arsenite, As(III), in the sample fluid 14, in steps (204) and (206) of process (200) of FIG. 2, the adsorption material 34' of each of the adsorption layers 34.1, 34.2 on the first 26 and third 30 electrodes is multilayered, wherein the first layer—on top of the first 26 and third 30 electrodes—comprises PAH—poly(allylamine) hydrogel—which acts as a cation/anion exchanger or as a first receptor layer to bind further receptors, and a second layer—on top of the first layer—comprises one or more of a set of bis-thiol-containing compounds that will bind aqueous As(III) quantitatively, one example of which is benzenediamidoethanethiol, abbreviated BDET.

The candidate bis-thiol-containing compounds are unique by comparison to other thiol-containing compounds in that they do not oxidize to disulfide (—S—S—) under atmospheric or aqueous conditions. In addition to complete As removal in pH neutral water, BDET has been shown to bind As in the presence of competing elements such as Zn, Cd, and Pb, in gold mining effluent, and for the binding of As in soil. BDET is ideally suited for use as the recognition component of an As sensor. In use, BDET derivatized with a carboxylate group, BDET-COOH, will be used as the surface coating on a QCM sensor. Under ambient pH conditions BDET-COOH will bind selectively to As (III) The resonant frequency by the active piezoelectric resonator 20.1 will directly correspond to the As bound on the surface BDET layer. Thus, the concentration of As present in the water being monitored is quantitatively determined.

The associated adsorption layer 34.1 on the first electrode 26, —i.e. of the active piezoelectric resonator 20.1—can be refreshed with a solution of HCL having a pH less than or equal to 4 as the associated regeneration fluid 50—used in a regeneration process described more fully hereinbelow—applied thereto in order to remove the bound arsenic and regenerate the active form of BDET adsorption layer 34.1 on the first electrode 26, so as to restore the active piezoelectric resonator 20.1 to, or near, its initial, virgin resonant frequency. The acid solution is then neutralized and the As(III) ions are filtered in a small As sorbent column before the solution is discharged.

Following the formation of the adsorption layer 34.2 on the third 30 electrode of the reference piezoelectric resonator 20.2, in step (208), the chemical receptors thereof are blocked, or immobilized, by saturating the chemical receptors thereof with arsenite, As(III) ions.

When using a PAH/BDET adsorption material 34' to selectively bind arsenite, As(III), the fluid contaminant sensing system 10 would utilize a cation filter—for example, comprising a cation exchange column in sodium (Na) form, as described more fully hereinbelow—upstream of the active sensor 16 so as to provide for removing cations from the sample fluid 14 that might otherwise interfere with the measurement by becoming adsorbed on the adsorption layer 34.1 of the active piezoelectric resonator 20.1.

The bonding of BDET to soft metals and metalloids takes place through covalent bond formation between the elements and the two sulfur atoms of the ligand. Thus, there will be no interferences from the binding of anions such as arsenate (As(V)), phosphate, nitrate or others. However, 95% of selenite, $H_2SeO_3$ is bound by BDET at pH 5.5. However, selenite can be easily reduced to elemental selenium (E0=+0.74 V) prior to the active sensor 16 with a reduction column by which As(V) is reduced to As(III) by passing the As(V) through a column of zero valence iron (ZVI).

In waters that contain As(V), a column with a reducing agent such as particulate Fe can be inserted upstream in the sample flow. The As(V) (E0=+0.56 V) is reduced to As(III) which is detected by the sensor. When desired, there can be two sample streams and two sensors, with one having the reducing column and one not. The difference between the two will indicate the presence of As(V).

The only interferences possible with BDET are with soft metals such as Cd, Hg, or Pb. In waters that contain cations, a cation exchange resin column in the sodium form is inserted upstream in the sample flow (for example, using ⅛" (3 mm) tubing at a flow rate of about 0.1 mL/min). The cation resin exchanges any Cd, Hg or Pb with Na that will not bind to the sensor. BDET does not bind Na or other cations from Groups 1 and 2.

In accordance with an alternative fifth aspect to selectively bind hexachlorobenzene in the sample fluid 14, in steps (204) and (206) of process (200) of FIG. 2, the adsorption material 34' of each of the adsorption layers 34.1, 34.2 on the first 26 and third 30 electrodes are formed in accordance with the teachings of U.S. Pat. No. 6,890,486, "MIP/QCM sensors for high sensitivity-fast sensing of small molecules in solution", incorporated herein by reference, which discloses molecular imprinted polymers that provide for selectively binding organic molecules such as hexachlorobenzene. In the coating process, monomers are polymerized on the surface of both the active and reference electrodes. The target molecule, in this case hexaclorobenzene, is applied to the matrix, and acts as a template. The template is subsequently removed from the matrix of adsorption layer 34.1 on the first electrode 26, —i.e. of the active piezoelectric resonator 20.1—by passing a benzene solution thereover, leaving an imprint that is selective for the hexaclorobenzene target analyte 12. The associated adsorption layer 34.1 on the first electrode 26, —i.e. of the active piezoelectric resonator 20.1—can be refreshed with a benzene solvent as the associated regeneration fluid 50—used in a regeneration process described more fully hereinbelow—applied thereto, —for example, when the adsorption layer 34.1 on the first electrode 26 becomes ⅔ saturated—in order to cleanse the adsorption layer 34.1 on the first electrode 26 of associated hexaclorobenzene, so as to restore the active piezoelectric resonator 20.1 to, or near, its initial, virgin resonant frequency.

Following the formation of the adsorption layer 34.2 on the third 30 electrode of the reference piezoelectric resonator 20.2, in step (208), the above-described template is not removed from the adsorption layer 34.2 on the third 30 electrode so as to provide for the template to act as the blocking substance 36' of the associated blocking layer 36.

In accordance with an alternative sixth aspect to detect biological substances. Antibodies can easily be produced that are specific for a wide variety of substances both large and small, and accordingly may be used as an associated adsorption material 34' of the adsorption layer 34.1 on the first electrode 26 of the active piezoelectric resonator 20.1, and of the adsorption layer 34.2 (if used) on the third electrode 30 of the reference piezoelectric resonator 20.2. For example, if monitoring for bacterial contamination, an antibody against any of the proteins on the bacterial surface can be made and applied as the adsorption material 34' of the associated adsorption layers 34.1, 34.2.

For example, to create a sensor for *E. coli*, in steps (204) and (206) of process (200) of FIG. 2, the adsorption material 34' of each of the adsorption layers 34.1, 34.2 on the first 26 and third 30 electrodes is multilayered, wherein the first layer—on top of the first 26 and third 30 electrodes—comprises PAH—poly(allylamine) hydrogel —, and a second layer—on top of the first layer—comprises an antibody to *E. coli*.

The reagent used as the regeneration fluid 50 to refresh the associated adsorption layer 34.1 on the first electrode 26, —i.e. of the active piezoelectric resonator 20.1 —, so as to restore the active piezoelectric resonator 20.1 to, or near, its initial, virgin resonant frequency, will be different for different antibodies depending on the stability range thereof, which would generally be in the range of pH 4 to pH 10. The stability range is supplied by the laboratories that create the antibodies. Mild acid or mild base reagents are the usual choices.

Following the formation of the adsorption layer 34.2 on the third 30 electrode of the reference piezoelectric resonator 20.2, in step (208), the chemical receptors thereof are blocked, or immobilized, using an antigen—for example, and *E. coli* ghost—as the associated blocking substance 36'.

In accordance with a further alternative aspect, the adsorption layers 34.1, 34.2 may be formed in accordance with the teachings of U.S. Patent Application Publication No. US 2005/0196532 A1 to Waldrop, III et al. that was published on 8 Sep. 2005, which is incorporated by reference herein in its entirety.

Referring to FIGS. 4-6*b*, in step (210) of process (200) of FIG. 2, the piezoelectric wafer 22 incorporating the quartz-crystal microbalances (QCM) 56.1, 56.2 with coated first 26 and third 30 electrodes is assembled within top 74 and bottom 76 blocks of the fluid contaminant sensor cell 54, wherein the piezoelectric wafer 22 is sandwiched between two pairs 78, 80 of O-rings 78.1, 78.2 and 80.1, 80.2, respectively. For example, in one set of embodiments, the top 74 and bottom 76 blocks are constructed from a plastic material, for example, NORYL®.

More particularly, a lower side of a first O-ring 78.1 provides for sealing against the first surface 22' of the piezoelectric wafer 22 proximate to, and concentric with, the first surface portion 20.1' of the active piezoelectric resonator 20.1, and therefore concentric with the associated first electrode 26, and an upper side of the first O-ring 78.1 provides for sealing against a corresponding first O-ring groove 82.1 in the top block 74, so as to provide for defining a first cavity 38 of the active sensor 16, wherein the first cavity 38 is bounded by the coated fluid-exposed first electrode 26, the first O-ring 78.1, and a corresponding bottom surface portion 74.1 of the top block 74. Furthermore, the first O-ring 78.1 is shaped, e.g. circular, and the inside dimension, e.g. diameter, thereof is sized, so that when the fluid contaminant sensor cell 54 is assembled, the first O-ring 78.1 substantially adjoins the periphery of the first electrode 26.

An upper side of a second O-ring 78.2 provides for sealing against the second surface 22' of the piezoelectric wafer 22 proximate to, and concentric with, the second surface portion 20.1" of the active piezoelectric resonator 20.1, and therefore concentric with the associated second electrode 28, and a lower side of the second O-ring 78.2 provides for sealing against a corresponding second O-ring groove 82.2 in the bottom block 76, so as to provide for opposing and balancing the forces applied to the piezoelectric wafer 22 by the first O-ring 78.1 as necessary to seal the periphery of the first cavity 38, which therefore provides for enabling the piezoelectric wafer 22 to float between the first 78.1 and second 78.2 O-rings. Furthermore, the second O-ring 78.2 is shaped, e.g. circular, and the inside dimension, e.g. diameter, thereof is sized, so that when the fluid contaminant sensor cell 54 is assembled, the second O-ring 78.2 substantially adjoins the periphery of the second electrode 28.

A lower side of a third O-ring 80.1 provides for sealing against the first surface 22' of the piezoelectric wafer 22 proximate to, and concentric with, the third surface portion 20.2' of the reference piezoelectric resonator 20.2, and therefore concentric with the associated third electrode 30, and an upper second side of the third O-ring 80.1 provides for sealing against a corresponding third O-ring groove 82.3 in the top block 74, so as to provide for defining a second cavity 40 of the reference sensor 18, wherein the second cavity 40 is bounded by the coated fluid-exposed third electrode 30, the third O-ring 80.1, and a corresponding bottom surface portion 74.2 of the top block 74. Furthermore, the third O-ring 80.1 is shaped, e.g. circular, and the inside dimension, e.g. diameter, thereof is sized, so that when the fluid contaminant sensor cell 54 is assembled, the third O-ring 80.1 substantially adjoins the periphery of the third electrode 30.

An upper side of a fourth O-ring 80.2 provides for sealing against the second surface 22' of the piezoelectric wafer 22 proximate to, and concentric with, the fourth surface portion 20.2" of the reference piezoelectric resonator 20.2, and therefore concentric with the associated fourth electrode 32, and a lower second side of the fourth O-ring 80.2 provides for sealing against a corresponding fourth O-ring groove 82.4 in the bottom block 76, so as to provide for opposing and balancing the forces applied to the piezoelectric wafer 22 by the third O-ring 80.1 as necessary to seal the periphery of the second cavity 40, which therefore provides for enabling the piezoelectric wafer 22 to float between the third 80.1 and fourth 80.2 O-rings. Furthermore, the fourth O-ring 80.2 is shaped, e.g. circular, and the inside dimension, e.g. diameter, thereof is sized, so that when the fluid contaminant sensor cell 54 is assembled, the fourth O-ring 80.2 substantially adjoins the periphery of the fourth electrode 32.

The top 74 and bottom 76 blocks are keyed to one another, with a key protrusion 84 from the top block 74 that mates with a key recess 86 in the bottom block 76, so as to provide for maintaining the concentricity of the first 82.1 and second 82.2 O-ring grooves with respect to one another, and so as to provide for maintaining the concentricity of the third 82.3 and fourth 82.4 O-ring grooves with respect to one another, and which prevents the top block 84 from either translating or rotating relative to the bottom block 76.

The first cavity 38 incorporates a first inlet 38.1 and a first outlet 38.2, wherein the first inlet 38.1 is in fluid communication with a first inlet port 88 on a first side 90 of the top block 74, and the first outlet 38.2 is in fluid communication with a first outlet port 92 on a second side 94 of the top block 74, wherein the first 90 and second 94 sides of the top block 74 are adjacent to one another, and during operation of the fluid contaminant sensor cell 54, a fluid pumped into the first inlet port 88 flows into the first cavity 38 through the first inlet 38.1 thereof, through the first cavity 38, and, following interaction with the active piezoelectric resonator 20.1, is then discharged from the first cavity 38 via the first outlet 38.2 of the first cavity 38, to, and then out of, the first outlet port 92 of the top block 74. Similarly, the second cavity 40 incorporates a second inlet 40.1 and a second outlet 40.2, wherein the second inlet 40.1 is in fluid communication with a second inlet port 96 on a third side 98 of the top block 74, and the second outlet 40.2 is in fluid communication with a second outlet port 100 on a fourth side 102 of the top block 74, wherein the third 98 and fourth 102 sides of the top block 74 are adjacent to one another, and during operation of the fluid contaminant sensor cell 54, a fluid pumped into the second inlet port 96 flows into the second cavity 40 via the second inlet 40.1 thereof, through the first cavity 38, and, following interaction with the reference piezoelectric resonator 20.2, is then discharged from the second cavity 40 via the second outlet 40.2 of second cavity 40, to, and then out of, the second outlet port 100 of the top block 74. For example, in one set of embodiments, the first inlet 88 and outlet 92 ports, and the second inlet 96 and outlet 100 ports are tapped with female pipe threads so as to provide for connection thereto.

Figure 3A:
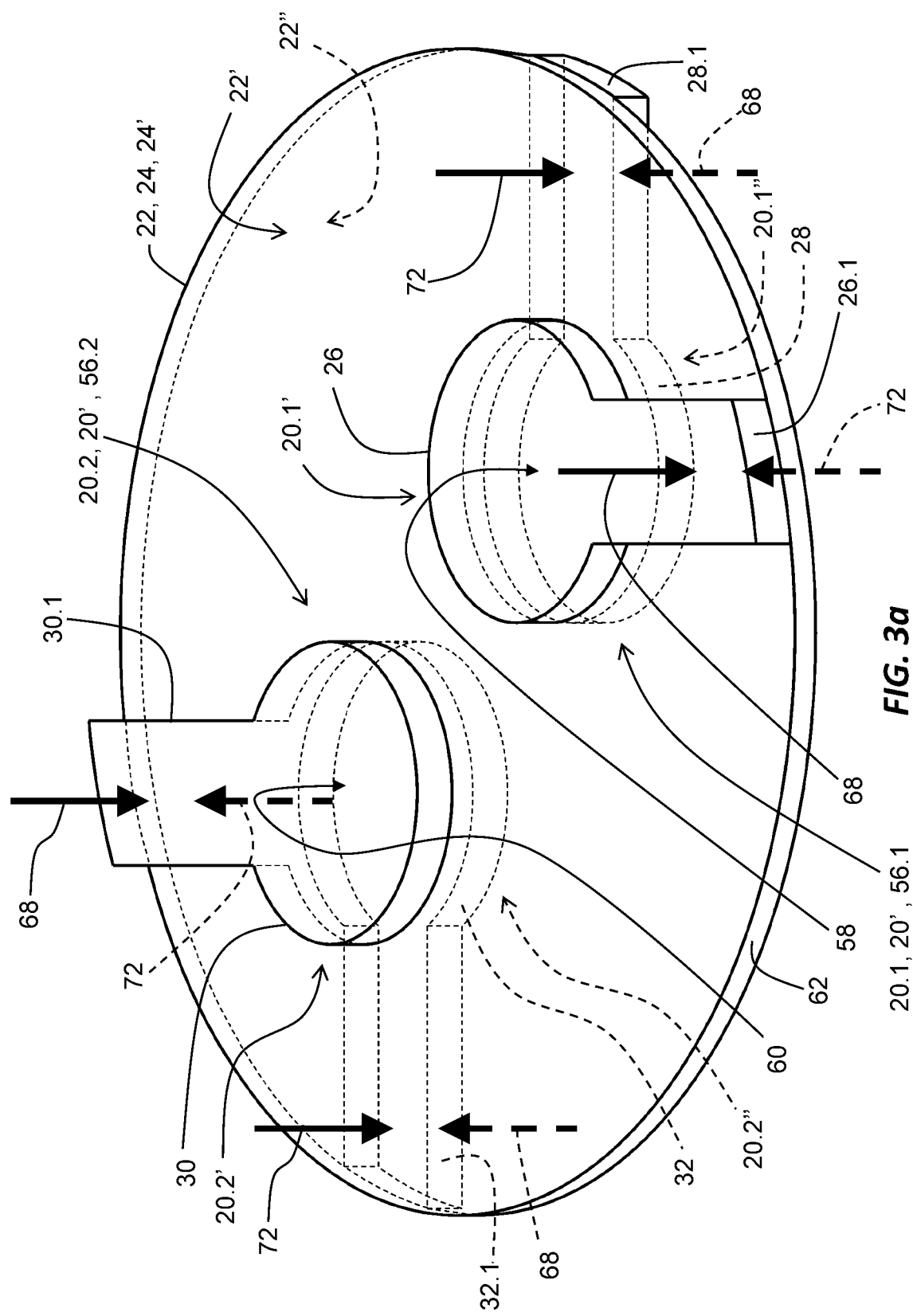
FIG. 3a illustrates a first embodiment of a quartz crystal incorporating a pair of quartz-crystal resonators, for used in a fluid contaminant sensing system.

Referring to FIGS. 3a and 6b, the top 74 and bottom 76 blocks together incorporate four pairs of Pogo-pin-style connectors 64, 70 that provide for axially engaging a peripheral rim 104 of the piezoelectric wafer 22—acting in directions that are substantially normal to the first 22' and second 22" surfaces of the piezoelectric wafer 22—at corresponding azimuthal locations of the conductive paths 26.1, 28.1, 30.1, 32.1 of the first 26 and second 28 electrodes and the third 30 and fourth 32 electrodes, respectively. Each pair of Pogo-pin-style connectors 64, 70 comprises a contact-forming Pogo-pin-style connector 64, a contact surface 66 of which engages one of the associated conductive paths 26.1, 28.1, 30.1, 32.1 at a location within the associated peripheral rim 104 of the piezoelectric wafer 22, as to apply a contact-forming bias force 68 to the associated first 22' or second 22" surfaces of the piezoelectric wafer 22 in a corresponding first axial direction so as to establish an electrical connection between the associated conductive path 26.1, 28.1, 30.1, 32.1 and an associated terminal 106' of the associated contact-forming Pogo-pin-style connector 64. Each pair of Pogo-pin-style connectors 64, 70 also comprises a remaining force-balancing Pogo-pin-style connector 70 that applies a force-balancing bias force 72 in an opposite direction from the associated contact-forming bias force 68 and acting upon an opposing surface 22', 22" of the piezoelectric wafer 22, so that at each azimuthal location of the pairs of Pogo-pin-style connectors 64, 70, the opposing contact-forming 68 and force-balancing 72 bias forces are balanced so as to enable the piezoelectric wafer 22 to otherwise axially float between the associated pairs 78, 80 of O-rings 78.1, 78.2 and 80.1, 80.2. Each Pogo-pin-style connector 64, 70 comprises a spring-biased pin portion 108 that is biased away from a corresponding hollow terminal portion 106 by an associated internal compression spring 110, and is inserted into the associated top 74 or bottom 76 block through a corresponding hole 112 that is aligned with the corresponding azimuthal location of the associated conductive path 26.1, 28.1, 30.1, 32.1 to which the contact surface 66 of the associated contact-forming Pogo-pin-style connector 64 engages.

The piezoelectric wafer 22 is located within a cylindrical well 114 in the top side 76.1 of the bottom block 76, and the piezoelectric wafer 22 is azimuthally located within the cylindrical well 112 by aligning a registration mark on the piezoelectric wafer 22 (not illustrated), with a corresponding registration mark on the periphery of the cylindrical well 112, which together provides for concentrically aligning the active 20.1 and reference 20.2 piezoelectric resonators with the corresponding O-ring groove 82.1, 82.2, 82.3, 82.4.

Figure 3B:
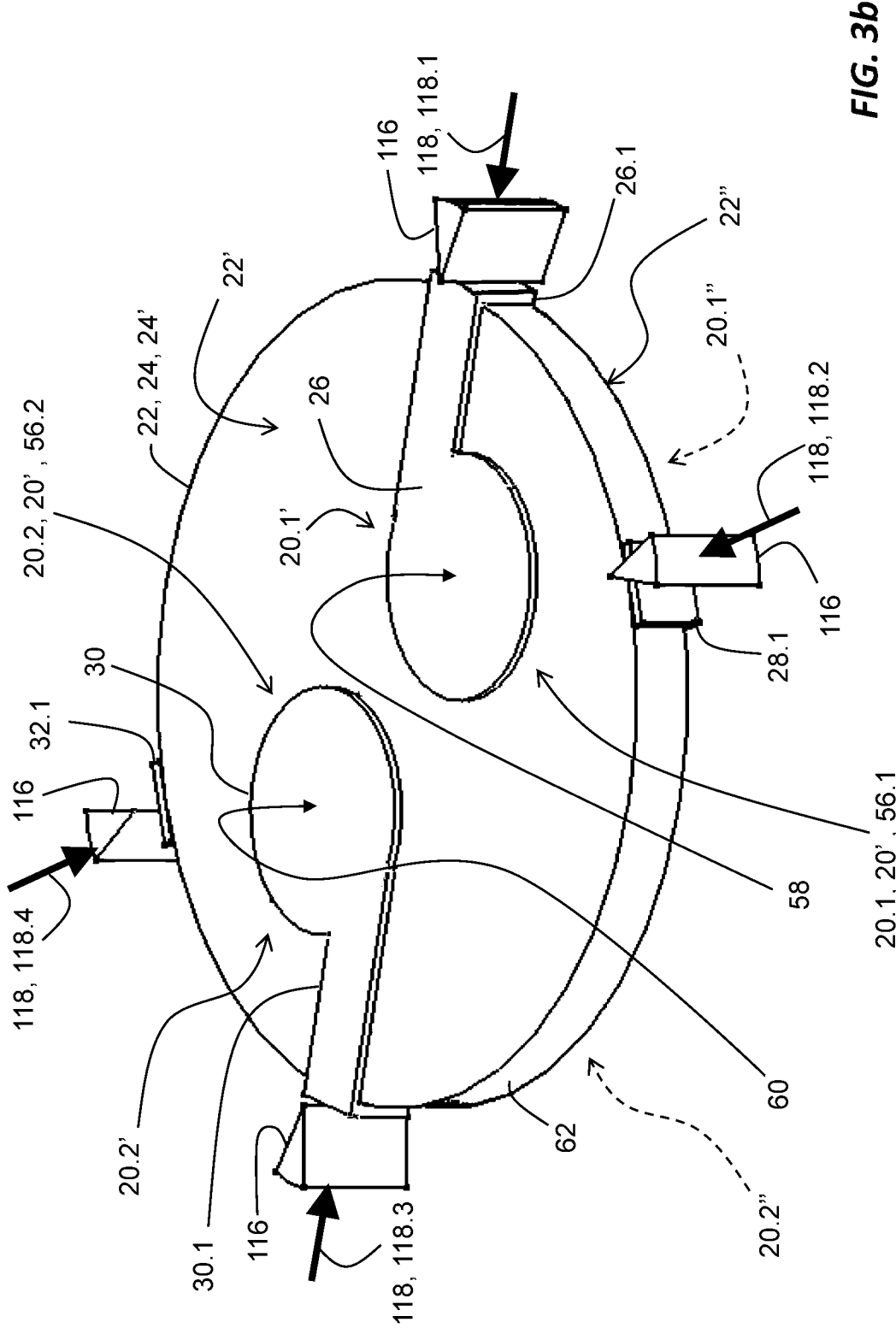
FIG. 3b illustrates a second embodiment of a quartz crystal incorporating a pair of quartz-crystal resonators, for used in a fluid contaminant sensing system.
Figure 4:
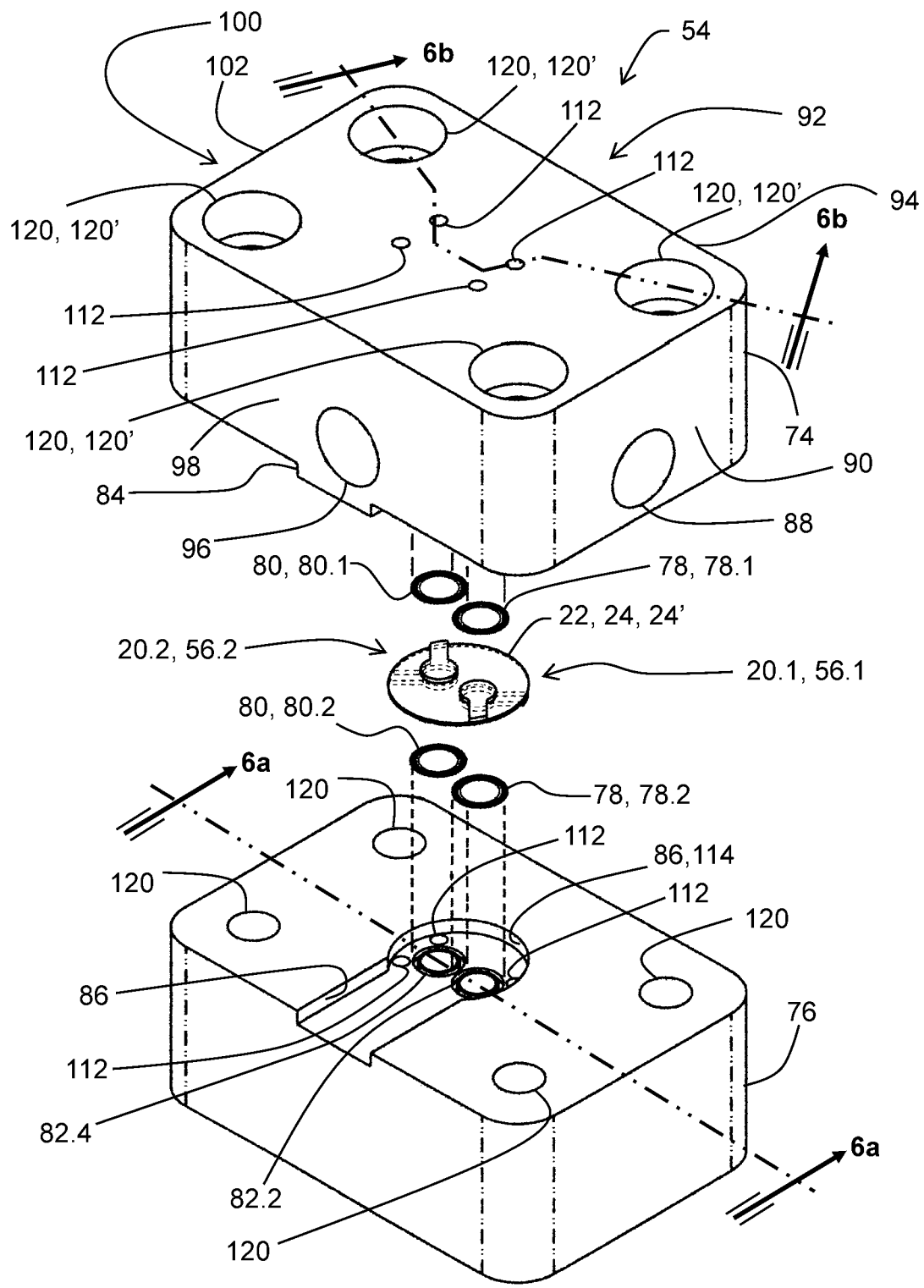
Figure 5:
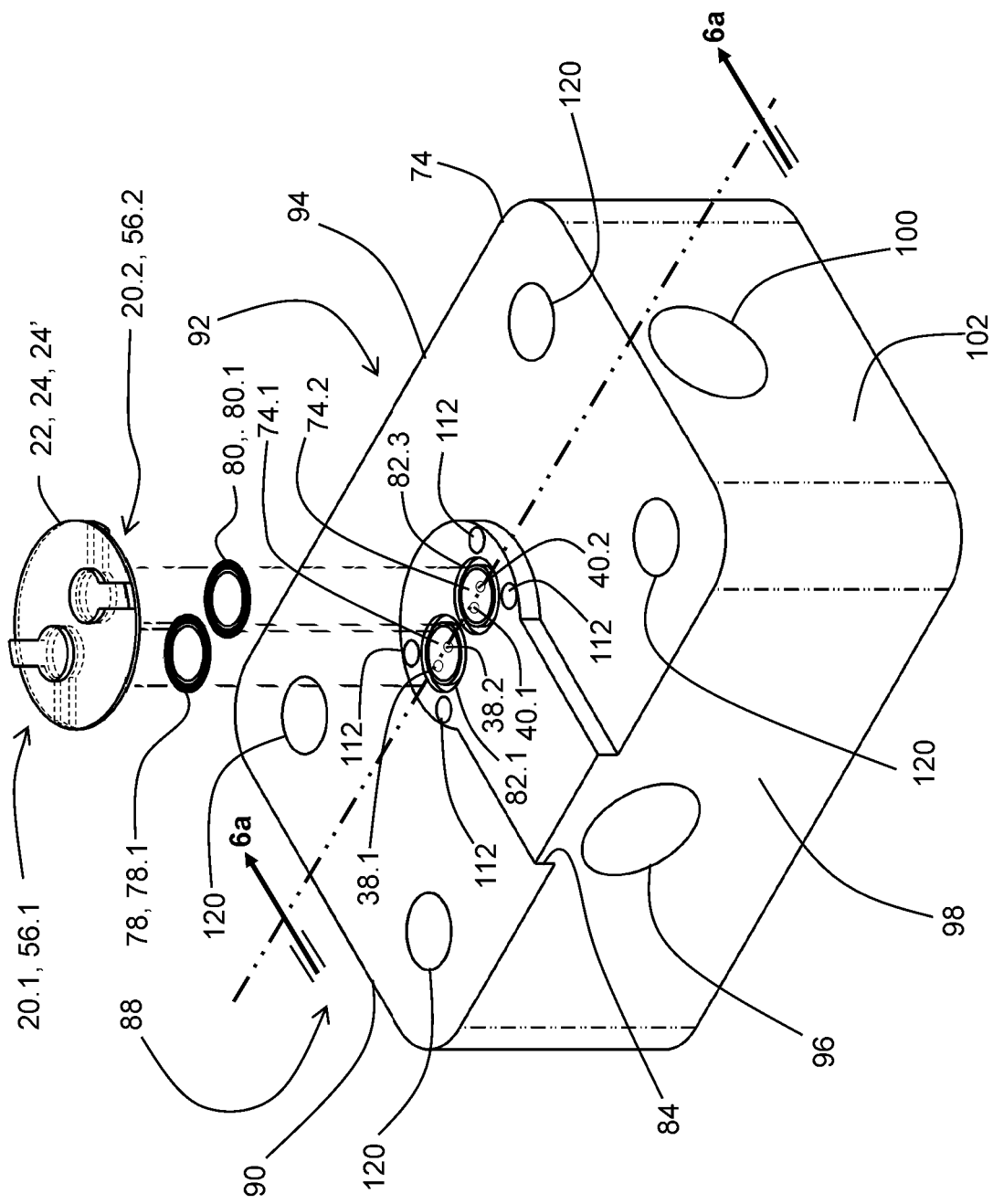
FIG. 5 illustrates and exploded view of a top portion of the sensor cell of a fluid contaminant sensing system illustrated in FIG. 4, with a view of the bottom side of an associated top housing portion.

Referring to FIG. 3b, in accordance with an alternative aspect for electrically contacting the conductive paths 26.1, 28.1, 30.1, 32.1 of the of the first 26 and second 28 electrodes and the third 30 and fourth 32 electrodes, respectively, each of the conductive paths 26.1, 28.1, 30.1, 32.1 is extended across the periphery 62 of the piezoelectric wafer 22, and the radially-outer surface of each is engaged by a corresponding radially-biased knife-edge conductor 116, by an associated radially-inward bias force 118, for example by a corresponding associated contact-forming Pogo-pin-style connector 64 (not illustrated), wherein the conductive paths 26.1, 28.1, 30.1, 32.1 are located at a corresponding two pairs of diametrically-opposed azimuthal locations, for example, with the peripheral locations of the conductive paths 26.1 and 30.1 associated with the first 26 and third 30 electrodes are diametrically opposed to one another so as to provide for radially balancing the associated first 118.1 and third 118.3 radially-inward bias forces, and with the peripheral locations of the conductive paths 28.1 and 32.1 associated with the second 28 and fourth 32 electrodes are diametrically opposed to one another so as to provide for radially balancing the associated second 118.2 and fourth 118.4 radially-inward bias forces.

The top 74 and bottom 76 blocks are held together with fasteners (not illustrated) through two sets of holes 120 in the top 74 and bottom 76 blocks, for example, counter-bored holes 120' in each of the top 74 and bottom 76 blocks that each cooperate with an associated machine screw and nut so that are each recessed below the top and bottom outer surfaces of the fluid contaminant sensor cell 54 when the fluid contaminant sensor cell 54 is assembled. Alternatively, one set of holes 118 in either the top 74 or bottom 76 blocks could be tapped, or the top 74 and bottom 76 blocks could be held together by some other means, for example, by clamping. Upon assembly of the fluid contaminant sensor cell 54, the pairs 78, 80 of O-rings 78.1, 78.2 and 80.1, 80.2 that sandwich the piezoelectric wafer 22 are compressed between the top 74 and bottom 76 blocks and the piezoelectric wafer 22 so as to seal the peripheries of the first 38 and second 40 cavities, so as to provide for any subsequently-contained fluid to interact primarily with the fluid-exposed-electrodes 26, 30 of the active 20.1 and reference 20.2 piezoelectric resonators, and not other portions of the associated piezoelectric wafer 22. Furthermore, upon assembly of the fluid contaminant sensor cell 54, the contact-forming Pogo-pin-style connectors 64 contact the corresponding conductive paths 26.1, 28.1, 30.1, 32.1 of the of the first 26 and second 28 electrodes and the third 30 and fourth 32 electrodes, so as to provide for external connection to the associated resonator drive circuit 42, 42.1, 42.2.

Although the above-described fluid contaminant sensor cell 54 incorporates a single piezoelectric wafer 22 incorporating active 20.1 and reference 20.2 piezoelectric resonators, it should be understood that separate piezoelectric wafers 22.1, 22.2 incorporating separate active 22.1 and reference 22.1 piezoelectric wafers could alternatively be incorporated in the fluid contaminant sensor cell 54, or separated fluid contaminant sensor cells 54—each constructed similarly to the above-described fluid contaminant sensor cell 54—could be used with separate piezoelectric wafers 22.1, 22.2, with one fluid contaminant sensor cell 54 incorporating the active piezoelectric resonator 20.1, and the other fluid contaminant sensor cell 54 incorporating the reference piezoelectric resonator 20.2.

Referring again to FIG. 2, in step (212) of process (200), the fluid contaminant sensor cell(s) 54 are incorporated in the fluid contaminant sensing system 10. More particularly, referring to FIGS. 7, 10, 13-16, 19 and 26, the second inlet port 96 of the fluid contaminant sensor cell 54, associated with the reference sensor 18, is operatively coupled through a first flow sensor 122 to the output of a first pump 124—for example, a controllable-flow-rate positive displacement pump—the input of which is operatively coupled to an outlet port 126.3 of a first controllable three-way valve 126 having first 126.1 and second 126.2 inlet ports, wherein the first inlet port 126.1 of the first controllable three-way valve 126 is operatively coupled to a source of fluid to be sensed 128, and the second inlet port 126.2 of the first controllable three-way valve 126 is operatively coupled to a source of a neutral fluid 52, for example, deionized water 52' (also referred to as "18 Megohm water"), wherein the neutral fluid 52, 52' is devoid of substances that might otherwise be adsorbed by the adsorption layer 34.1 of the active sensor 16. The second outlet port 100 of the fluid contaminant sensor cell 54, associated with the reference sensor 18, is operatively coupled to a sample discharge line or tank 132.

The first inlet port 88 of the fluid contaminant sensor cell 54, associated with the active sensor 16, is operatively coupled through a second flow sensor 134 to an outlet port 136.3 of a second controllable three-way valve 136 having first 136.1 and second 136.2 inlet ports, wherein the first inlet port 136.1 of the second controllable three-way valve 136 is operatively coupled to the output of the first pump 124, and the second inlet port 136.2 of the second controllable three-way valve 136 is operatively coupled to the output of a second pump 138—for example, a controllable-flow-rate positive displacement pump —, the input of which is operatively coupled to a source of regeneration fluid 50 that is used to refresh the adsorption layer 34.1 of the active piezoelectric resonator 20.1, as described more fully hereinbelow. The first outlet port 92 of the fluid contaminant sensor cell 54, associated with the active sensor 16, is operatively coupled to an inlet port 142.3 of a third controllable three-way valve 142 having first 142.1 and second 142.2 outlet ports, wherein a first outlet port 142.1 of the third controllable three-way valve 142 is operatively coupled to the sample discharge line or tank 132, and the second outlet port 142.2 of the third controllable three-way valve 142 is operatively coupled to a separate waste tank 144 for subsequent disposal.

The first 126, second 136 and third 142 controllable three-way valves are under control of a controller 46, the latter which together provide for controlling the operating states thereof. The controller 46, in cooperation with an associated memory 46.1, provides for controlling the operation of the associated active 16 and reference 18 sensors and for processing the outputs therefrom. In a first operating state 126' of the first controllable three-way valve 126, the first inlet port 126.1 thereof is operatively coupled to the outlet port 126.3 thereof, so as to provide for the first pump 124—under control of the controller 46—to receive and pump the fluid to be sensed 128 both to the first inlet port 136.1 of the second controllable three-way valve 136, and through the first flow sensor 122 to the reference sensor 18. In a second operating state 126" of the first controllable three-way valve 126, the second inlet port 126.2 thereof is operatively coupled to the outlet port 126.3 thereof, so as to provide for the first pump 124 to receive and pump the neutral fluid 52, 52' both to the first inlet port 136.1 of the second controllable three-way valve 136, and through the first flow sensor 122 to the reference sensor 18.

In a first operating state 136' of the second controllable three-way valve 136, the first inlet port 136.1 thereof is operatively coupled to the outlet port 136.3 thereof, so as to provide for the either the fluid to be sensed 128 or the neutral fluid 52, 52'—depending upon the operating state 126', 126" of the first controllable three-way valve 126—to be pumped by the first pump 124 through the second flow sensor 134 and into the first inlet port 88 of the fluid contaminant sensor cell 54, associated with the active sensor 16. In a second operating state 136" of the second controllable three-way valve 136, the second inlet port 136.2 thereof is operatively coupled to the outlet port 136.3 thereof, so as to provide for the regeneration fluid 50 to be pumped by the second pump 138—under control of the controller 46—through the second flow sensor 134 and into the first inlet port 88 of the fluid contaminant sensor cell 54, associated with the active sensor 16.

In a first operating state 142' of the third controllable three-way valve 142, the first outlet port 142.1 thereof is operatively coupled to the inlet port 142.3 thereof, so as to provide for discharging the fluid from the first outlet port 92 of the fluid contaminant sensor cell 54 to the sample discharge line or tank 132. In a second operating state 142" of the third controllable three-way valve 142, the second outlet port 142.2 thereof is operatively coupled to the inlet port 142.3 thereof, so as to provide for discharging the fluid from the first outlet port 92 of the fluid contaminant sensor cell 54 to the waste tank 144 for subsequent disposal, for example, so as to provide for safely disposing a potentially hazardous regeneration fluid 50.

The actuation and flow rate of the second pump 138, and at least the actuation of the first pump 124, are under control of the controller 46. For example, in one set of embodiments, the first 124 and second 138 pumps are each implemented as an adjustable-flow-rate diaphragm pump, for example, an MP-6 micro pump manufactured by Bartels Mikrotechnik.

The first pump 124 provides for a known and controllable flow rate of the sample fluid 14 through the active sensor 16 so as to provide for determining therefrom the total amount of sample fluid 14 pumped therethrough within a given period of time. The concentration of target analyte 12 in the sample fluid 14 can then be calculated from the ratio of the mass or moles of target analyte 12 measured by the active sensor 16, divided by the total amount of sample fluid 14 inferred from the period of time over which the sample fluid 14 was pumped through the active sensor 16 given the known flow rate of the first pump 124.

The second pump 138 provides for pumping the regeneration fluid 50 through the active sensor 16 at a known and controllable flow rate, wherein the flow rate can be adjusted so that the flow rate of the regeneration fluid 50 through the active sensor 16 is the same as the flow rate of the neutral fluid 52 through the reference sensor 18 during a below-described process to refresh the adsorption layer 34.1 of the active sensor 16.

The fluid contaminant sensing system 10 further incorporates a temperature sensor 146 that provides for sensing the temperature of the fluid pumped by the first pump 124—for example, discharged therefrom—to the active 16 or reference 18 sensors, and which is operatively coupled to the controller 46 so as to communicate a signal responsive to that temperature to the controller 46. For example, in one set of embodiments, the temperature sensor 146 comprises a Dallas Temperature sensor DS18B20. The first 122 and second 134 flow sensors are also operatively coupled to the controller 46 so as to provide for communication associated flow rate signals $Q_R$, $Q_A$ thereto, wherein the first flow sensor 122 communicates a measure of the flow rate $Q_R$ through the reference sensor 18 to the controller 46, and second flow sensor 134 communicates a measure of the flow rate $Q_A$ through the active sensor 16.

Figure 8A:
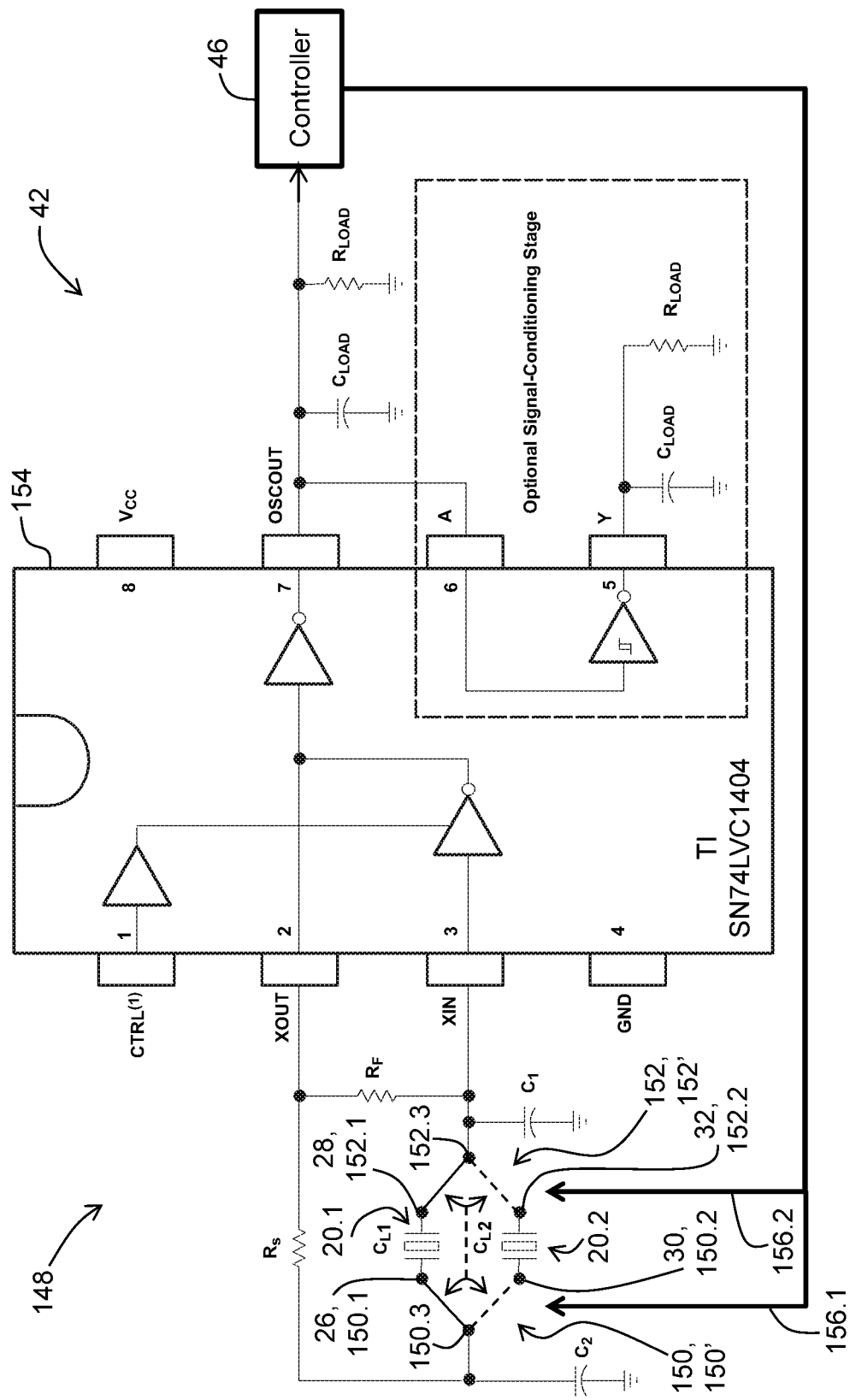
FIG. 8a illustrates a first embodiment of a resonator drive circuit in cooperation with an associated controller in accordance with the block diagram illustrated in FIG. 7.

The active 20.1 and reference 20.2 piezoelectric resonators are used in an associated at least one resonator drive circuit 42, 42.1, 42.2 to inherently control the resonant frequency of an associated at least one oscillator 148, 148.1, 148.2 to be the resonant frequency of the associated active 20.1 and reference 20.2 piezoelectric resonator. Referring also to FIG. 8*a*, in accordance with a first set of embodiments, the resonator drive circuit 42 comprises a single associated oscillator 148 that is alternately, and mutually-exclusively, switched during alternating first periods of time to the active piezoelectric resonator 20.1, and then during alternating second periods of time to the reference piezoelectric resonator 20.2, The active 20.1 and reference 20.2 piezoelectric resonators are resonated during alternating, mutually-exclusive periods of time so as to mitigate against injection locking that might otherwise occur if both the active 20.1 and reference 20.2 piezoelectric resonators associated with the same piezoelectric wafer 22 were resonated simultaneously, wherein injection locking refers to the phenomenon that can occur when a first oscillator is disturbed by a second oscillator operating at a nearby frequency, wherein when the coupling therebetween is strong enough and the frequencies near enough, the second oscillator can capture the first oscillator, causing both to oscillate at substantially the same frequency.

For example, as illustrated in FIG. 8*a*, in one embodiment, the first electrode 26 of the active piezoelectric resonator 20.1 is operatively coupled to a first switch contact 150.1 of a first single-pole-double-throw (SPDT) switch 150, and the second electrode 28 of the active piezoelectric resonator 20.1 is operatively coupled to a first switch contact 152.1 of a second single-pole-double-throw (SPDT) switch 152. Similarly the third electrode 30 of the reference piezoelectric resonator 20.2 is operatively coupled to a second switch contact 150.2 of the first single-pole-double-throw (SPST) switch 150, and the fourth electrode 32 of the reference piezoelectric resonator 20.2 is operatively coupled to a second switch contact 152.2 of the second single-pole-double-throw (SPST) switch 152, wherein the pole 150.3 of the first single-pole-double-throw (SPST) switch 150 is operatively coupled to the XIN terminal of a Texas Instruments SN74LVC1404 Oscillator Driver for Crystal Oscillator or Ceramic Resonator 154, and the pole 152.3 of the second single-pole-double-throw (SPST) switch 152 is operatively coupled to a junction between a first terminal of capacitor $C_2$ and a first terminal of resistor $R_S$, wherein the second terminal of resistor $R_S$ is operatively coupled to the XOUT terminal of the SN74LVC1404 154, and the second terminal of capacitor $C_2$ is operatively coupled to ground, with resistor $R_F$ operatively coupled between the XOUT and XIN terminals of the SN74LVC1404 154. The OSCOUT terminal of the SN74LVC1404 154, or an optionally signal-conditioned version thereof, is operatively coupled to the controller 46 so as to provide for measuring the associated resonant frequency of whichever of the active 20.1 or reference 20.2 piezoelectric resonators are operatively coupled to the SN74LVC1404 154 by the first 150 and second 152 single-pole-double-throw (SPST) switches at any given time, in accordance with the following published Data Sheet by Texas Instruments: "SN74LVC1404 Oscillator Driver for Crystal Oscillator or Ceramic Resonator", SCE469E—August 2003—Revised June 2014, 2016, 28 pages, downloadable from http://www.ti.com/lit/ds/symlink/sn74lvc1404.pdf, which is incorporated herein by reference in its entirety. For example, in one embodiment, the first 150 and second 152 single-pole-double-throw (SPST) switches are each implement with an ADG736 CMOS Dual SPDT (Single Pole Double Throw) switch 150', 152', which are toggled by corresponding digital output signals 156.1, 156.2 from the controller 46.

Alternatively, the second 28 and fourth 30 electrodes of the active 20.1 and reference 20.2 piezoelectric resonators may be interconnected, or utilize a common electrode—i.e. where the second 28 and fourth 32 electrodes are different portions of an underlying continuous electrode, —either within the fluid contaminant sensor cell 54, or external thereto, with the junction therebetween, or the common electrode, connected to the XIN terminal of the SN74LVC1404 154, and the remaining first 26 and third 30 electrodes connected to first single-pole-double-throw (SPST) switch 150 as described hereinabove, the latter of which is used exclusively to alternate between the active 20.1 and reference 20.2 piezoelectric resonators under control of the controller 46, as described hereinabove.

Yet further alternatively, either single-pole-double-throw (SPDT) switch 150, 152 could be implemented with a corresponding pair of single-pole-single-throw (SPST) switches.

Figure 8B:
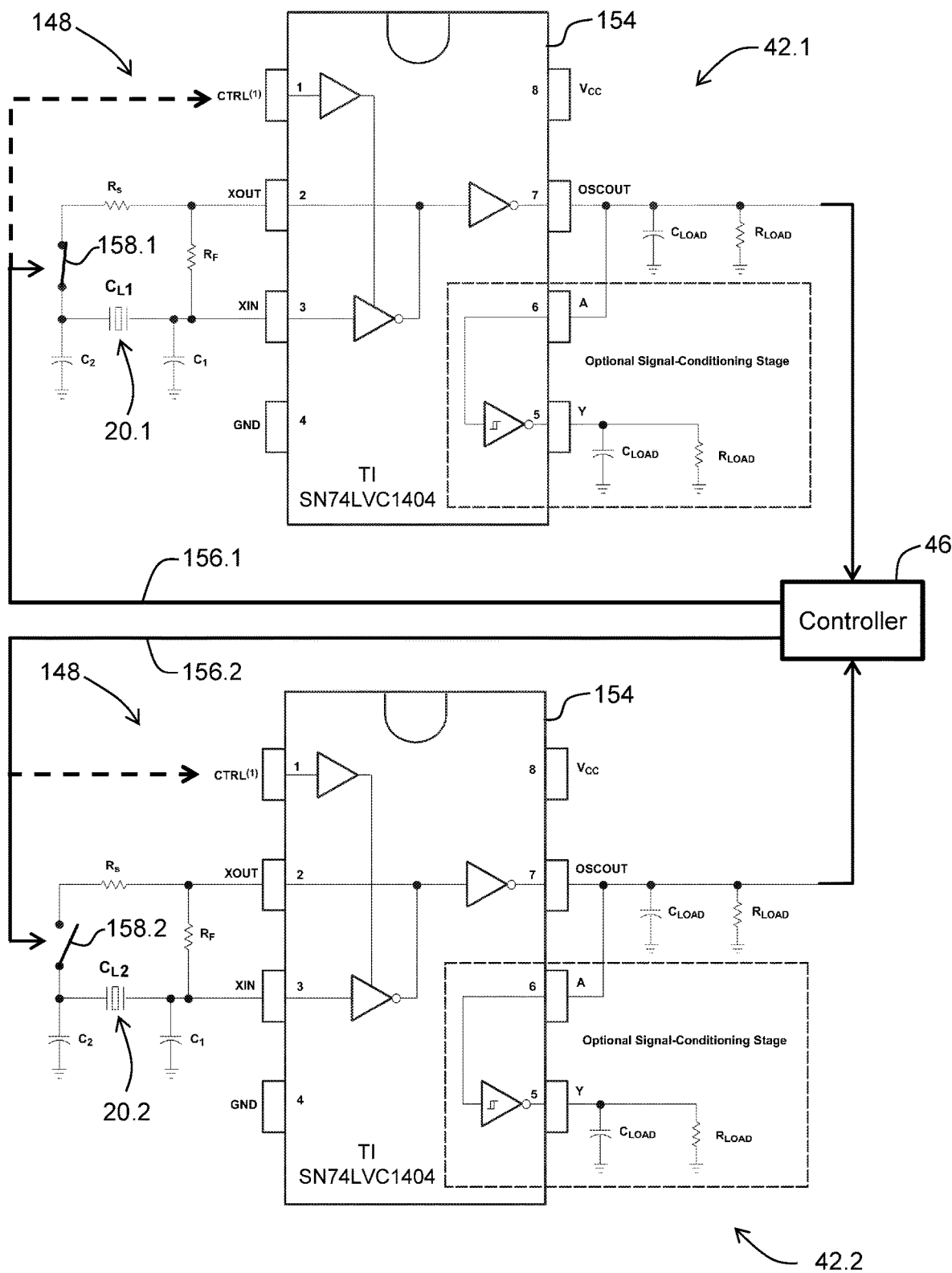
FIG. 8b illustrates an alternative, second embodiment of a resonator drive circuit in cooperation with an associated controller, for use in either sequentially or simultaneously driving the active and reference sensors of a fluid contaminant sensing system.

Yet further alternatively, referring to FIG. 8*b*, each of the active 20.1 and reference 20.2 piezoelectric resonators could be connected to a corresponding associated resonator drive circuit 42.1, 42.2, each of which is configured the same as for the resonator drive circuit 42 of FIG. 8*a*, except the that the associated active 20.1 and reference 20.2 piezoelectric resonators are each connected directly to the corresponding associated resonator drive circuit 42.1, 42.2, and the particular active 20.1 and reference 20.2 piezoelectric resonator is activated either using a controllable single-pole-single-throw (SPST) switch 158.1, 158.2 between the first terminal of capacitor $C_2$, and the first terminal of resistor $R_S$, or by operatively coupling a corresponding digital output signal 156.1, 156.2 directly to the CTRL terminal of the corresponding SN74LVC1404 154, without need if the corresponding single-pole-single-throw (SPST) switch 158.1, 158.2. If the active 26 and reference 18 sensors are implemented with separate active 22.1 and reference 22.1 piezoelectric wafers that are mechanically isolated from one another, the associated active 20.1 and reference 20.2 piezoelectric resonators may be resonated simultaneously, thereby precluding the need the above-described single-pole-single-throw (SPST) switches 158.1, 158.2, so as to provide for simultaneously measuring the associated resonant frequencies thereof.

Unless in cooperation with active 26 and reference 18 sensors implemented with separate active 22.1 and reference 22.1 piezoelectric wafers that are mechanically isolated from one another, the resonator drive circuit 42, 42.1, 42.2 and associated first 150 and second 152 single-pole-double-throw (SPDT) switches, or single-pole-single-throw (SPST) switches 158.1, 158.2, are operated in one of two operating states 42', 42". In the first operating state 42' of the resonator drive circuit 42, 42.1, 42.2, the pole 150.3 of the first single-pole-double-throw (SPDT) switch 150 is operatively coupled to the first switch contact 150.1 thereof, and the pole 152.3 of the second single-pole-double-throw (SPDT) switch 152 is operatively coupled to the first switch contact 152.1 thereof; or the first single-pole-single-throw (SPST) switch 158.1 is closed (or the associated resonator drive circuit 42.1 is activated), and the second single-pole-single-throw (SPST) switch 158.2 is open (or the associated resonator drive circuit 42.2 is deactivated); depending upon the configuration of the resonator drive circuit 42, 42.1, 42.2, so as to provide for the resonator drive circuit 42, 42.1, 42.2 to drive and oscillate the active piezoelectric resonator 20.1 at its resonant frequency. Similarly, in the second operating state 42" of the resonator drive circuit 42, 42.1, 42.2, the pole 150.3 of the first single-pole-double-throw (SPDT) switch 150 is operatively coupled to the second switch contact 150.2 thereof, and the pole 152.3 of the second single-pole-double-throw (SPDT) switch 152 is operatively coupled to the second switch contact 152.2 thereof; or the first single-pole-single-throw (SPST) switch 158.1 is open (or the associated resonator drive circuit 42.1 is deactivated), and the second single-pole-single-throw (SPST) switch 158.2 is closed (or the associated resonator drive circuit 42.2 is activated); depending upon the configuration of the resonator drive circuit 42, 42.1, 42.2, so as to provide for the resonator drive circuit 42, 42.1, 42.2 to drive and oscillate the reference piezoelectric resonator 20.2 at its resonant frequency.

Yet further alternatively, the resonator drive circuit(s) 42, 42.1, 42.2, associated switches 150, 152, 158.1, 158.2, and an associated frequency counter can be implemented with an associated application specific integrated circuit (ASIC).

Yet further alternatively, the active 20.1 and reference 20.2 piezoelectric resonators could each be driven in accordance with the teachings of U.S. Pat. No. 6,169,459 for an active-bridge oscillator, which is incorporated by reference herein in its entirety.

In accordance with one set of embodiments, the fluid contaminant sensing system 10 is implemented as what is referred to as a monitor comprising a monitor base unit that cooperates with one or more fluid contaminant sensor cells 54, with each of a plurality of fluid contaminant sensor cells 54 configured to sense a different target analyte 12. The monitor base unit comprises at least one plug-in receptacle for an associated fluid contaminant sensor cells 54; a power supply (not illustrated); and the associated hardware illustrated in FIGS. 7, 10, 13-16, 19 and 26 including the above-described controller 46; resonator drive circuit(s) 42; 42.1, 42.2; associated switches 148, 152, 158.1, 158.2; associated pumps 124, 138; associated controllable three-way valves 126, 136, 142; associated flow sensors 122, 134; temperature sensor 146; source of neutral fluid 52; source of regeneration fluid 50; waste tank 144; and additional hardware for preconditioning and pH control described hereinbelow.

For example, in one set of embodiments, the controller 46 comprises a single-board computer, for example, including, but not limited to, an Arduino or Raspberry Pi microcomputer. For example, in one embodiment, the controller 46 is implemented with a Teensy 3.2 USB Development Board.

The controller 46 may incorporate one or more associated communication buses or ports operating in accordance with one or more associated communication interfaces, for example, inter alia, USB, i2c, SPI, RS232 or RS485, for communicating with the other electronic or electronically-controlled components of the fluid contaminant sensing system 10, so as to provide for the associated monitor to incorporate a modular architecture. In one set of embodiments, the controller 46 comprises a flash-based microcontroller containing routines for reading from the sensor interface and sensor buses, either storing the associated sensor measurement(s) for local processing or display, or transmitting the associated sensor measurement(s) to a remote display, storage or control system 160 for subsequent use. For example, the associated sensor measurement(s) may be transmitted to the remote display, storage or control system 160 using either a cabled (e.g. wired or fiber optic) or wireless connection, either directly or via a network interface, for example, via an Ethernet connection or the Internet; or using a portable or removable storage device, for example, that might incorporate a USB interface to communication with the controller 46.

Figure 9:
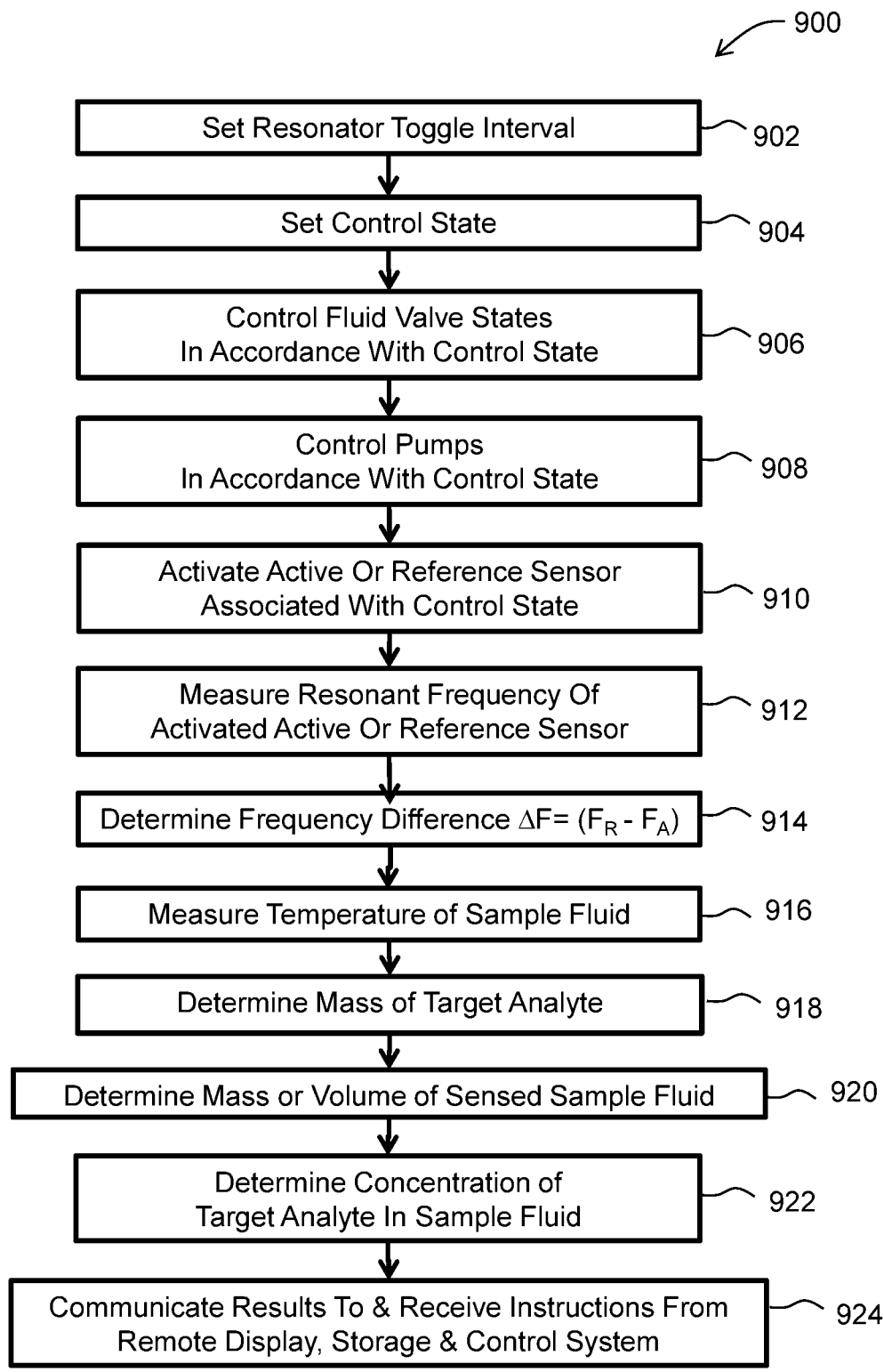
FIG. 9 illustrates a flow chart of an associated monitor control process.

Referring to FIG. 9, in accordance with one embodiment of the controller 46 implemented with a Teensy 3.2 USB Development Board, the controller 46 provides for operating a monitor control process (900) to control the fluid contaminant sensing system 10.

In step (902) of the monitor control process (900), the controller 46 sets the toggle interval, i.e. the period of time over which one of the active 20.1 and reference 20.2 piezoelectric resonators, whichever is activated, remains activated before the other of the active 20.1 and reference 20.2 piezoelectric resonators is activated, in an alternating fashion. For example, in one embodiment, the toggle interval is about 4 seconds. The resonant frequencies can be measured by counting the cycles of oscillation of the associated oscillator 148, in which case, a relatively longer toggle interval would provide for counting more cycles, which provides for a relatively higher resolution. For example, at least a one second toggle interval would provide for a 1 Hz resolution of a 10 MHz signal, with some additional time needed in the toggle interval to allow for stabilization. A lower frequency would require a greater amount of time for the same resolution, and vice versa. In accordance with a first embodiment, the toggling between the active 20.1 and reference 20.2 piezoelectric resonators is under direct, i.e. software, control of the controller 46, using a digital output signal therefrom. In accordance with a second embodiment, the toggling between the active 20.1 and reference 20.2 piezoelectric resonators may alternatively be facilitated with an Analog Devices ADG752 analog switch In accordance with a third embodiment, the toggling between the active 20.1 and reference 20.2 piezoelectric resonators is controlled by the above-described application specific integrated circuit (ASIC).

Figure 7:
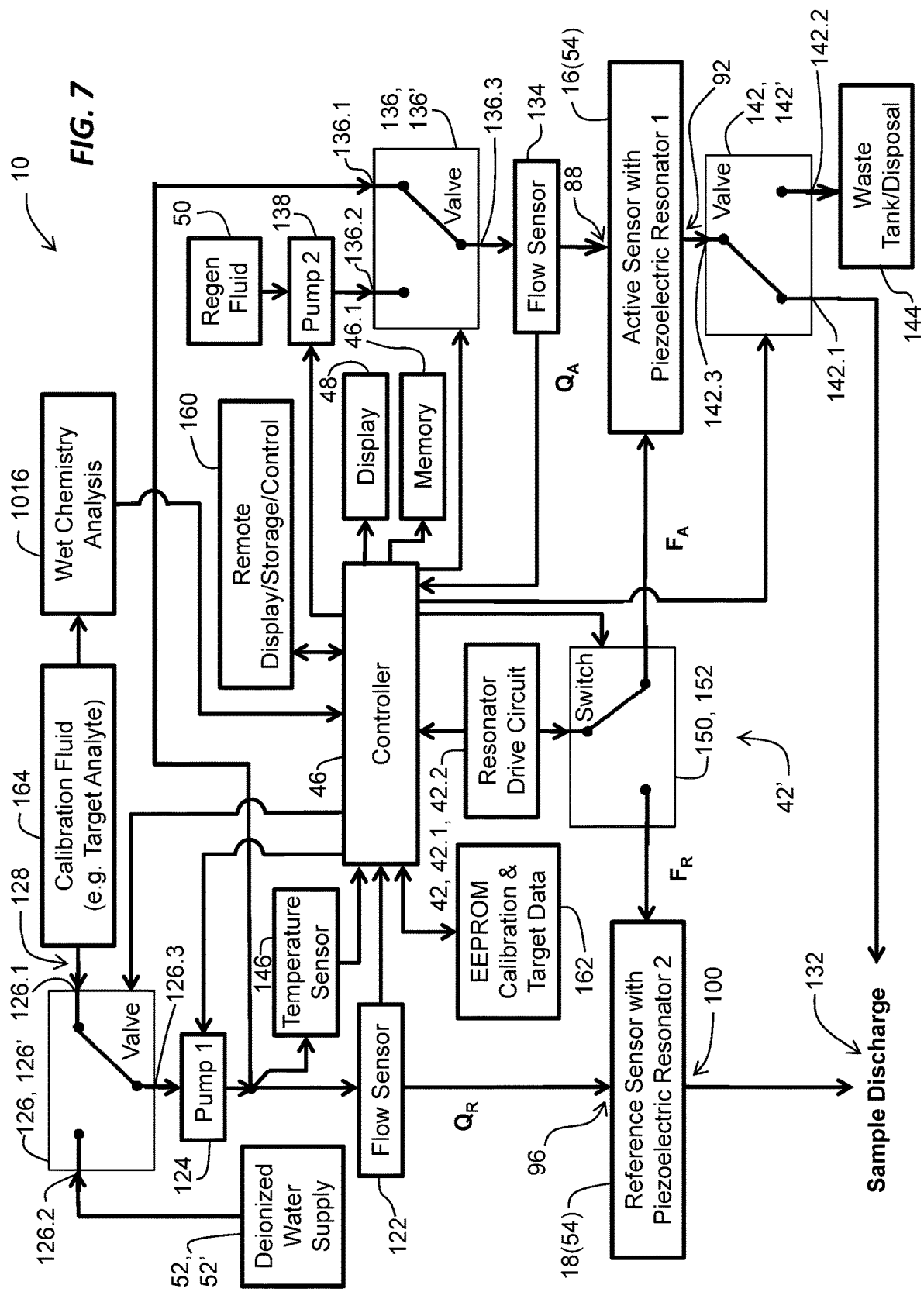
FIG. 7 illustrates a block diagram of a fluid contaminant sensing system during an associated sensor calibration process, with the associated active sensor being driven by an associated resonator drive circuit.
Figure 11:
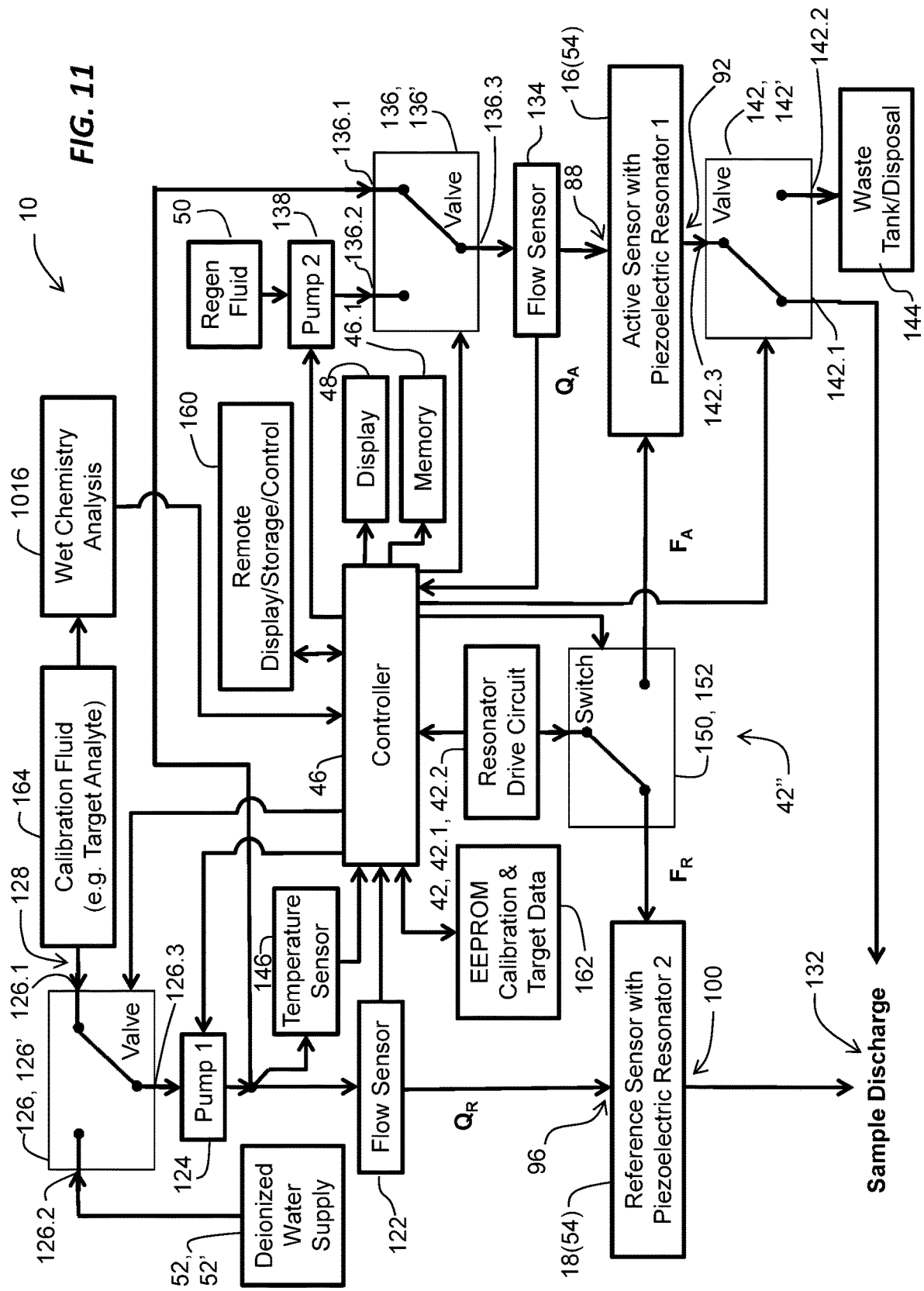
FIG. 11 illustrates a block diagram of a fluid contaminant sensing system during an associated sensor calibration process corresponding to FIG. 7, but with the associated reference sensor being driven by the associated resonator drive circuit.
Figure 22:
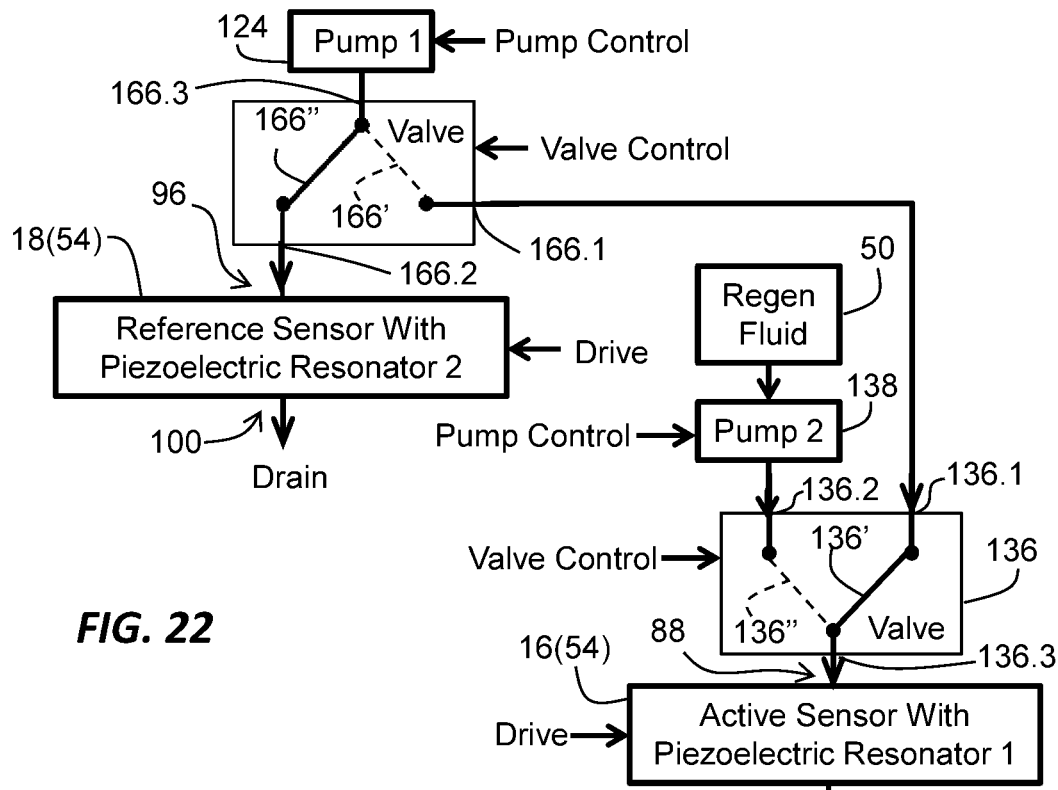
FIG. 22 illustrates a first alternative topology for supplying fluid to the active and reference sensors.
Figure 23:
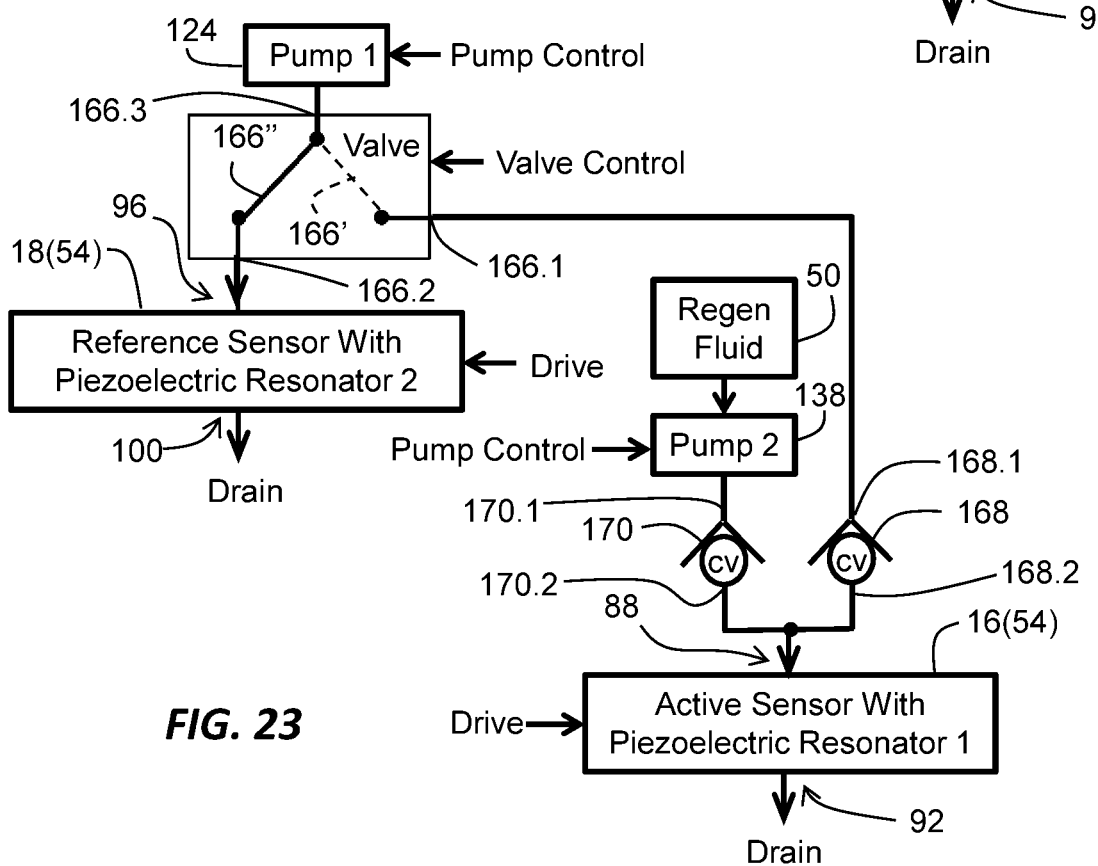
FIG. 23 illustrates a second alternative topology for supplying fluid to the active and reference sensors.
Figure 25:
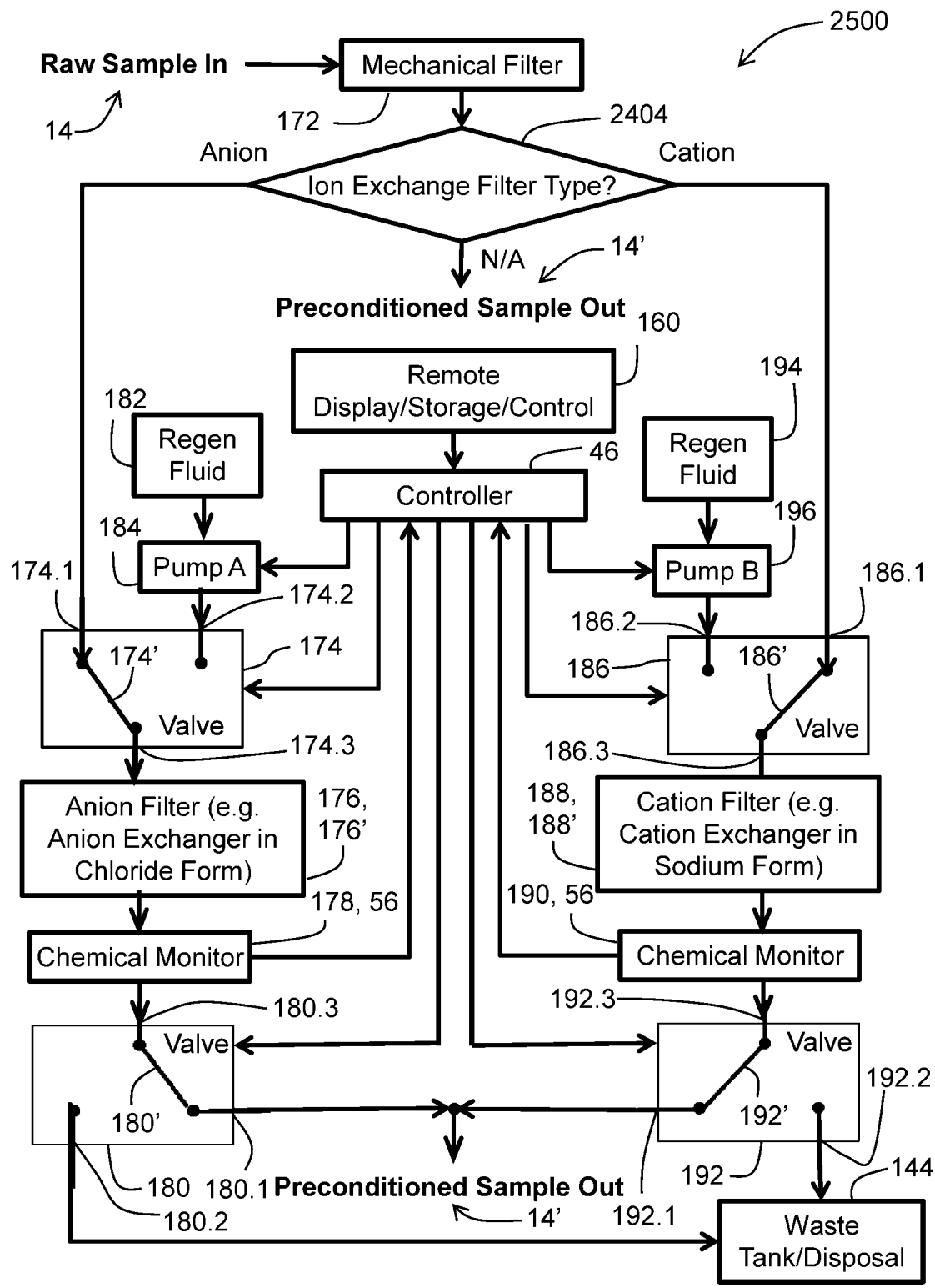
FIG. 25 illustrates a block diagram of the preconditioner illustrated in FIGS. 20 and 21, during operation of the associated continuous sensing process illustrated in FIG. 19.
Figure 26:
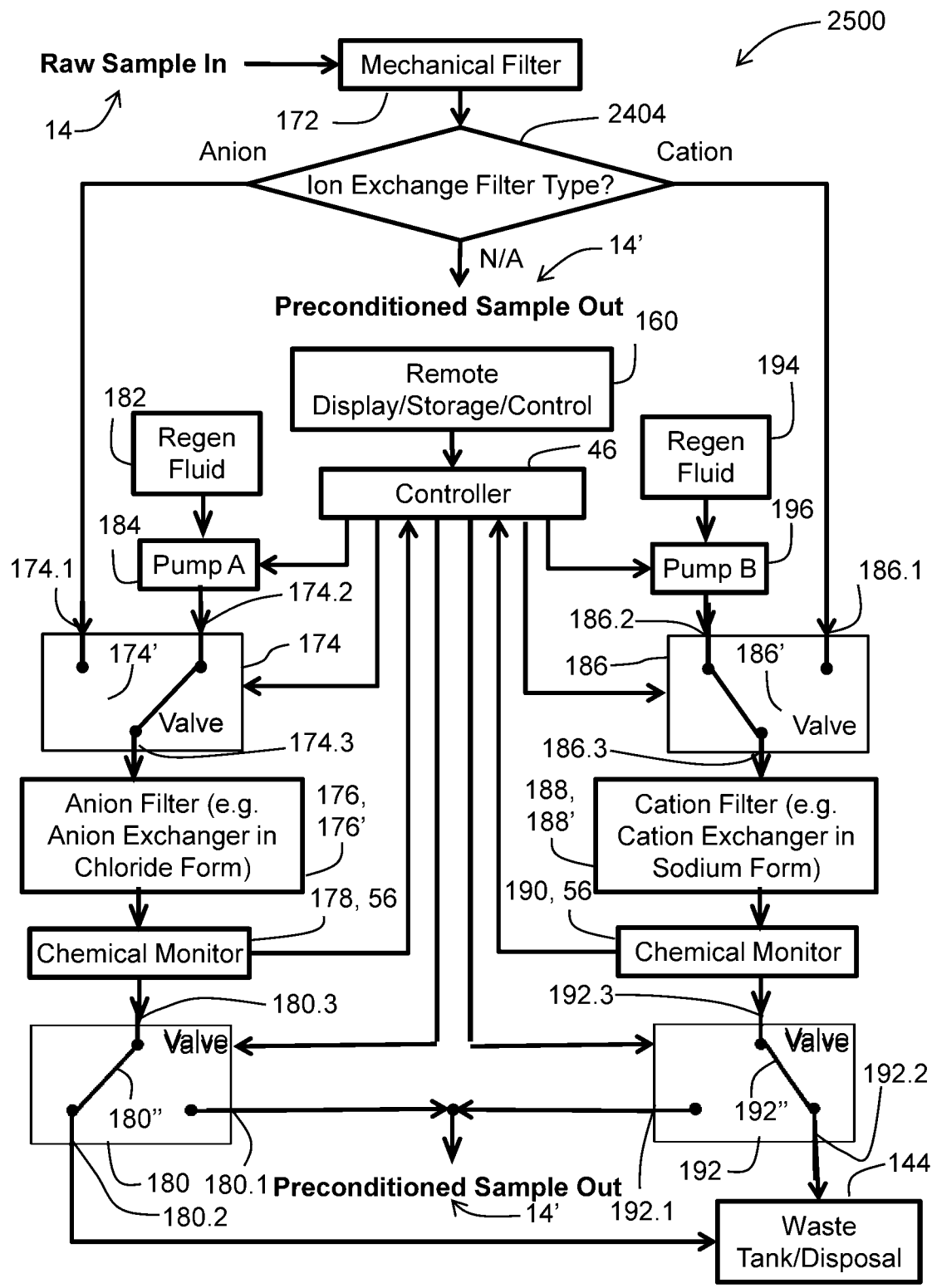
FIG. 26 illustrates a block diagram of the preconditioner illustrated in FIG. 25, during an associated process for refreshing an associated anion filter, or during an associated process for refreshing an associated cation filter.

In step (904) of the monitor control process (900), the controller 46 sets the associated control state of the associated first 126, second 136 and third 142 controllable three-way valves, the first 124 and second 138 pumps, and the first 150 and second 152 single-pole-double-throw (SPDT) switches, or single-pole-single-throw (SPST) switches 158.1, 158.2 depending upon the embodiment, and also controls the associated sequencing of the control states of, and depending upon, the associated calibration, sensing, refresh, preconditioning or pH control process. For example, FIGS. 7 and 11 illustrate control states associated with an associated calibration process; FIGS. 14-17 illustrate control states associated with an associated sensor refresh process; FIGS. 20 and 27-29 illustrate control states associated with an associated sensing process; FIGS. 22 and 23 illustrate control states associated with an associated preconditioning process; and FIGS. 25 and 26 illustrate control states associated with an associated pH control process.

In step (906) of the monitor control process (900), the first 126, second 136 and third 142 controllable three-way valves are controlled, i.e. set to the associated operating state, in accordance with the associated control state, as described more fully hereinbelow.

In step (908) of the monitor control process (900), the activations, and possibly the flow rates, of the first 124 and second 138 pumps are controlled in accordance with the associated control state, as described more fully hereinbelow.

In step (910) of the monitor control process (900), depending upon the toggling state of the active 20.1 and reference 20.2 piezoelectric resonators, either the active 20.1 of reference 20.2 piezoelectric resonators—mutually exclusively if using a shared, single piezoelectric wafer 22—are activated so as to resonate the associated active 20.1 or reference 20.2 piezoelectric resonator. For example, in one set of embodiments, for a shared resonator drive circuit 42, the above described first 150 and second 152 single-pole-double-throw (SPDT) switches are switched to provide for switching either the first 26 and second 28 electrodes, or the third 30 and fourth 32 electrodes, to the resonator drive circuit 42 responsive to a toggle signal from the ARM processor of the Teensy 3.2 USB Development Board, depending upon the state—i.e. 0 or 1 of an associated I/O pin—of the toggle signal, wherein the toggle signal is held at a particular state for the above-describe toggle interval before switching to the other state for the same toggle interval, and then repeating the toggling process to repetitively alternate between activation of the active 20.1 and reference 20.2 piezoelectric resonators, wherein the associated toggle interval of the toggle signal from the ARM is programmable or controllable.

Then, in step (912) of the monitor control process (900), the resulting resonant frequency of the activated active 20.1 or reference 20.2 piezoelectric resonator is measured. For example, in one set of embodiments, the output from the oscillator 148, 148.1, 148.2 is operatively coupled to the ARM chip embedded on the Teensy 3.2 USB Development Board, which in turn measures the associated frequency, for example, by measuring the period of time associated with a predetermined number of cycles of the oscillator output signal (for example, using associated Arduino software installed on the Teensy 3.2 USB Development Board). For example, for Frequency counting there is an in-built function in the software "FreqCount.read" which automatically counts the number of peaks of the signal in one second (Counts/sec). This number (Frequency) is placed in a variable and displayed. The frequency counter determines the frequency of each of the active 20.1 and reference 20.2 piezoelectric resonators. Alternatively, the resonant frequencies of the active 20.1 and reference 20.2 piezoelectric resonators may be measured with a commercially-available frequency counter, for example, a Hewlett Packard HP 5386A Frequency Counter.

In step (914) of the monitor control process (900), the frequency difference between the resonant frequencies of the active 20.1 and reference 20.2 piezoelectric resonators, so as to provide for determining the mass or moles of the target analyte 12 with inherent compensation for the effects of the temperature, density and viscosity of the sample fluid 14.

In step (916) of the monitor control process (900), the controller 46 provides for measuring the temperature of the sample fluid 14 is measured with an associated temperature sensor 146, for use in normalizing the associated liquid volume of the sample fluid 14 that has flowed through the active sensor 16, when calculating the concentration of the target analyte 12 in the sample fluid 14. For example, in one set of embodiments, a Dallas Temperature sensor DS18B20 inputs the temperature signal to the ARM chip embedded on the Teensy 3.2 USB Development Board, or a similar microcontroller, for example, that would be associated with each fluid contaminant sensor cell 54. For example, the fluid contaminant sensing system 10 would also incorporate a relatively more powerful single board computer, for example, a Raspberry pi, provides for communicating with the individual microcomputers associated with each fluid contaminant sensor cell 54, and provides for handling associated data processing for the control and reporting functions, external communications, and the user interface. As used herein, the term controller 46 is not limited to a single computer or processor, but is intended to represent one or more computers or processors as necessary to carry out the associated functionality, regardless of the particular data processing, control and communications architecture.

In step (918) of the monitor control process (900), the mass or moles of the target analyte 12 adsorbed by the adsorption layer 34.1 of the first electrode 26 of the active sensor 16 is determined responsive to the frequency difference from step (916), and responsive to associated calibration data, for example, either stored in the memory 46.1 of the controller 46, or stored on an associated EEPROM 162 that is operatively coupled to the controller 46. In accordance with one set of embodiments, the EEPROM 162 is incorporated in or with the fluid contaminant sensor cell 54, so as to provide for the inherently linking the associated calibration data with the fluid contaminant sensor cell 54 to which that calibration applies. For example, the calibration data includes a table or parameters of a mathematical model that provides for defining a functional relationship of the mass or moles of the target analyte 12 adsorbed by the adsorption layer 34.1 of the first electrode 26 of the active sensor 16 as a function of either the associated resulting resonant frequency, or the associated frequency difference with respect to the corresponding resonant frequency of the associated reference sensor 18 when exposed to the same calibration fluid, as described more fully hereinbelow. The calibration data includes an identification of the target analyte 12 to which the calibration table or mathematical-model parameters is associated.

In step (920) of the monitor control process (900), the controller 46 provides for determining the total amount, i.e. moles, mass or volume, of the sensed sample fluid 14 associated with the mass of the target analyte 12 adsorbed by the adsorption layer 34.1 of the first electrode 26 of the active sensor 16, responsive to either the known flow rate of the first pump 124, and the total period of time over which the sample fluid 14 flowed at that flow rate through the first cavity 38 of the active sensor 16, or responsive to a direct measurement of the flow rate using the second flow sensor 134, wherein in either case, the flow rate is corrected to a standard temperature using the temperature measurement from the temperature sensor 146 that was measured in step (916). For example, the concentration might be expressed as parts-per-billion, parts-per-million, or as weight-per-volume, for example, micrograms or nanograms per liter.

In step (922) of the monitor control process (900), the controller 46 provides for determining the concentration of the target analyte 12 as a ratio of the total mass or moles of the target analyte 12 from step (918), divided by the total amount, i.e. moles, mass or volume, of the sensed sample fluid 14 from step (920).

In step (924) of the monitor control process (900), the controller 46 provides for communicating with a remote display, storage or control system 160, so as to provide for transmitting data from the fluid contaminant sensing system 10—for example, measurements and/or associated calculated values, or warning or error messages—thereto, and so as to provide for receiving commands therefrom, for example, to enter a specific control state. For example, the individual microcomputers—which provide for relatively low-level functions, including managing sensor data, pump control, sensor calibration data, switch and valve control, and resonant drive control, preconditioning control, pH measurement, pH control, and provide a generic interface such as Ethernet or USB—would transfer sensor data to the associated single board computer for relatively higher level processing including data aggregation and relatively long-term analyses.

Referring again to FIG. 2, in step (214) of process (200), and referring to FIGS. 10, 7, 11 and 12, the fluid contaminant sensing system 10 is calibrated prior to first use by first preparing a predetermined volume of calibration fluid 164 comprising a predetermined concentration of the target analyte 12 in a neutral fluid 52, e.g. ultra-pure deionized water 52', pumping the calibration fluid 164 through the first 38 and second 40 cavities of the active 16 and reference 18 sensors, measuring over time the associated resonant frequencies of the active 20.1 and reference 20.2 piezoelectric resonators, calculating the corresponding associated frequency differences, and associating these frequency differences with the corresponding mass of target analyte 12 adsorbed by the adsorption layer 34.1 on the first electrode 26 of the active sensor 16. For example, in one set of embodiments, the concentration of the target analyte 12 in the calibration fluid 164 is set to a level corresponding to an upper bound of a range of concentrations over which relatively accurate measurements from the fluid contaminant sensing system 10 are desired, for example, and upper bound of a government-established threshold for the target analyte 12 in the sample fluid 14. For example, in accordance with one embodiment, if the fluid contaminant sensor cell 54 was adapted for sensing selenite as the target analyte 12, and the upper threshold value of selenite in the sample fluid 14 was 50 ppb, then the calibration fluid 164 would comprise a solution of 50 ppb selenite in deionized water 52'.

Figure 10:
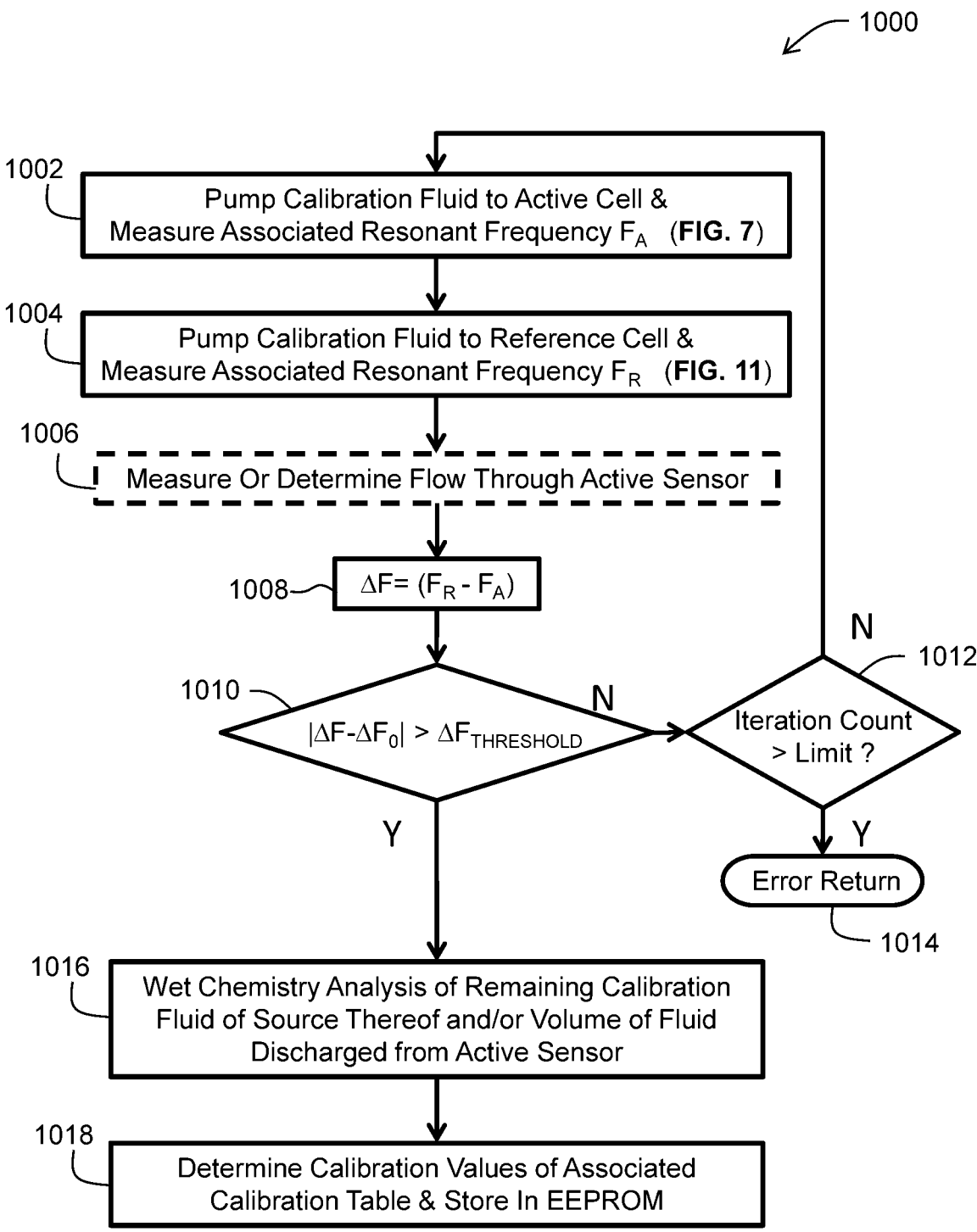
FIG. 10 illustrates a flow chart of an associated sensor calibration process.

Referring to FIGS. 10 and 7, the associated calibration process (1000) commences in step (1002) by using the using the first pump 124 to pump the calibration fluid 164 through the first cavity 38 of the active sensor 16, with the associated first 126, second 136 and third 142 controllable three-way valves each in its corresponding first operating state 126', 136', 142', and measuring the resonant frequency of the active piezoelectric resonator 20.1 with the resonator drive circuit 42, 42.1, 42.2 operating in the first operating state 42' thereof. The flow rate of the first pump 124 is sufficiently slow—for example, about 0.5 ml/minute—so as to provide for sufficient residence time within the first cavity 38 for nearly all of the target analyte 12 therein to become adsorbed by the adsorption layer 34.1 on the first electrode 26 of the active sensor 16, i.e. so that the associated capture ratio of the target analyte 12 ions or species to the associated chemical receptor binding sights of the associated adsorption material 34' is at least nearly 100%.

Then, referring to FIGS. 10 and 11, in step (1004), the calibration fluid 164 is pumped by the first pump 124 through the second cavity 40 of the reference sensor 18, without changing the operating states 126', 136', 142' of the first 126, second 136 and third 142 controllable three-way valves, but with the resonator drive circuit 42, 42.1, 42.2 operating in the second operating state 42" so as to provide for measuring the resonant frequency of the reference piezoelectric resonator 20.2. Then, optionally in step (1006), the total flow of the calibration fluid 164 is determined either from 1) a direct measurement from the second flow sensor 134 of the flow rate through the first cavity 38 over an associated period of time; 2) an inference of the flow rate through the first cavity 38 through the first cavity 38 given a predetermined rate of flow of the first pump 124 assuming a given distribution of flow from the first pump 124 to the first 38 and second 40 cavities or from a determination of the distribution of flow using flow rate measurements from the first 122 and second 134 flow sensors; or 3) of the flow rate through the first cavity 38 through the first cavity 38 given a predetermined rate of flow of the first pump 124 if the fluid contaminant sensing system 10 is configured in accordance with alternative topologies of FIG. 22 or 23, described hereinbelow.

Then, in step (1008), a frequency difference $\Delta F$ is determined as the difference between the resonant frequencies $F_R$ and $F_A$ of the active 20.1 and reference 20.2 piezoelectric resonators, respectively. If, in step (1010), the magnitude of the difference between the frequency difference $\Delta F$ and a corresponding initial frequency difference $\Delta F_0$—determined prior to commencement of the calibration process (1000)—does not exceed a frequency difference threshold $\Delta F_{THRESHOLD}$, and if, in step (1012), an iteration count does not exceed a limit, then the calibration process (1000) repeats, beginning with step (1002). For example, in one set of embodiments, the frequency difference threshold $\Delta F_{THRESHOLD}$ is set so that the adsorption layer 34.1 on the first electrode 26 of the active sensor 16 becomes about ⅔ saturated with target analyte 12—as reflected by a corresponding saturation frequency difference $\Delta F_{SATURATION}$, so as to provide for a corresponding effective operating range (EOR) of the active sensor 16. Otherwise, from step (1012), if the iteration limit is exceeded, then, then the calibration process (1000) terminates with an error in step (1014).

Figure 12:
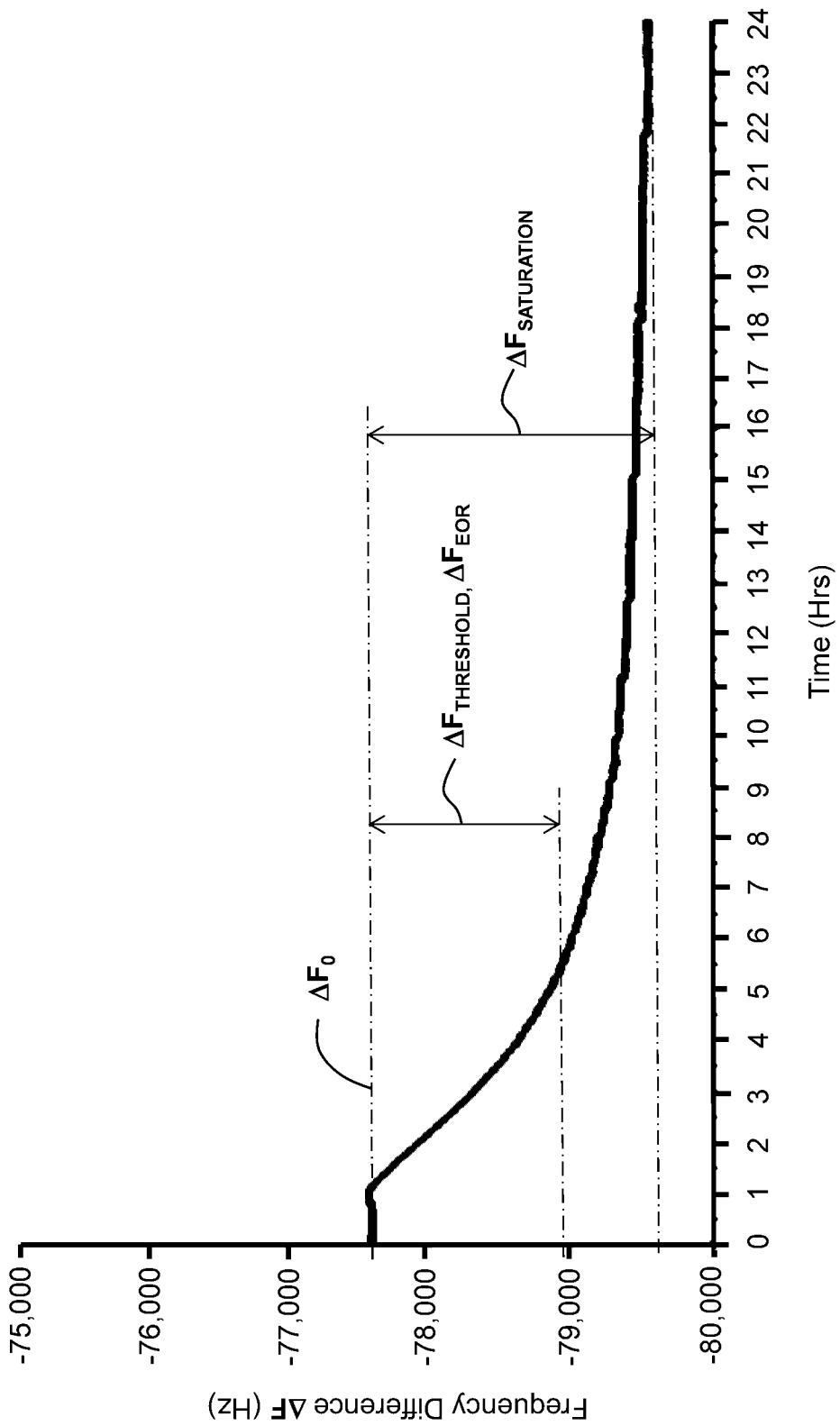
FIG. 12 illustrates an example of an output of the fluid contaminant sensing system during the associated sensor calibration process.
Figure 13A:
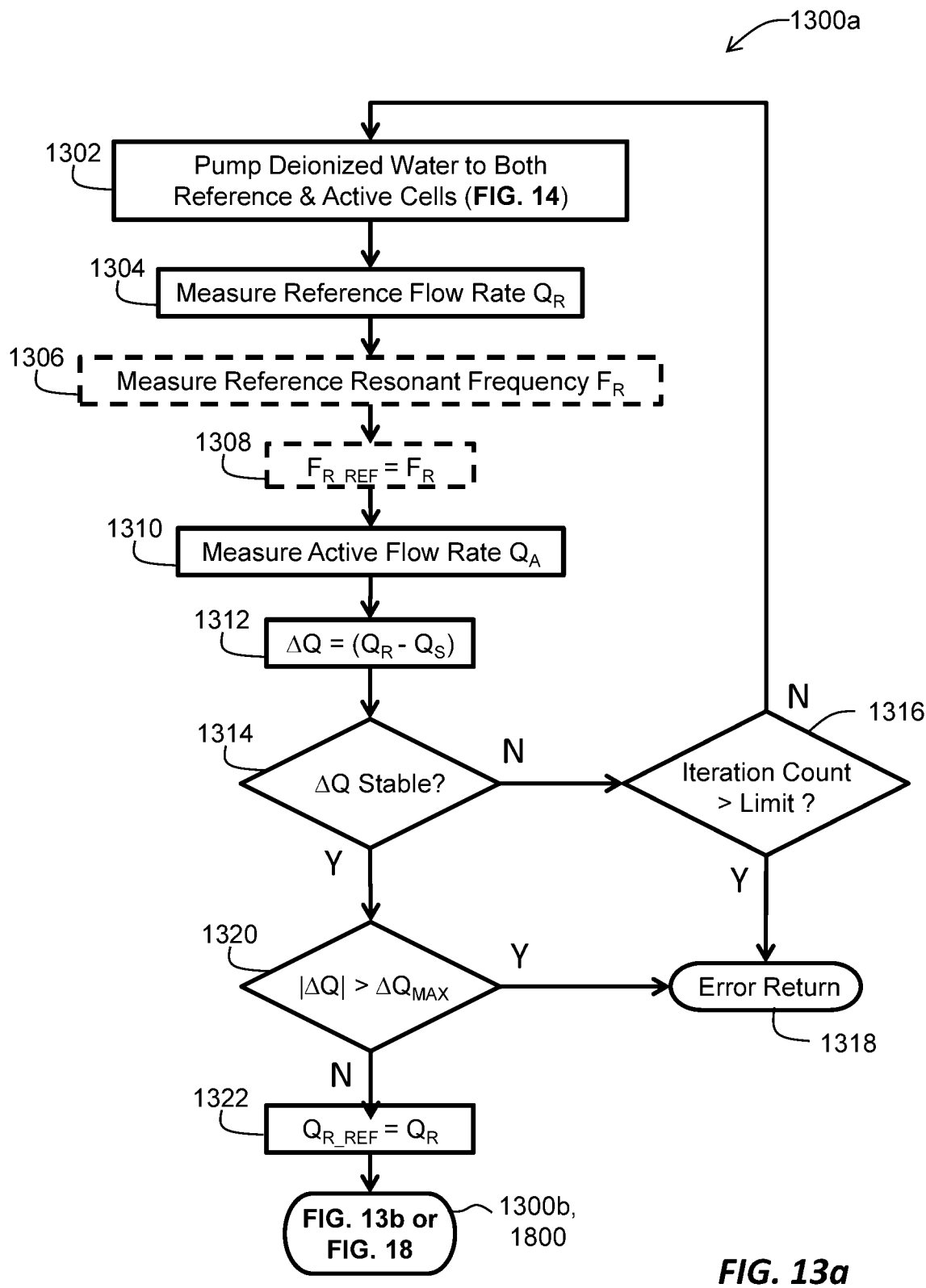
FIG. 13a illustrates a flow chart of a first phase of a process for refreshing the active sensor of a fluid contaminant sensing system.
Figure 13B:
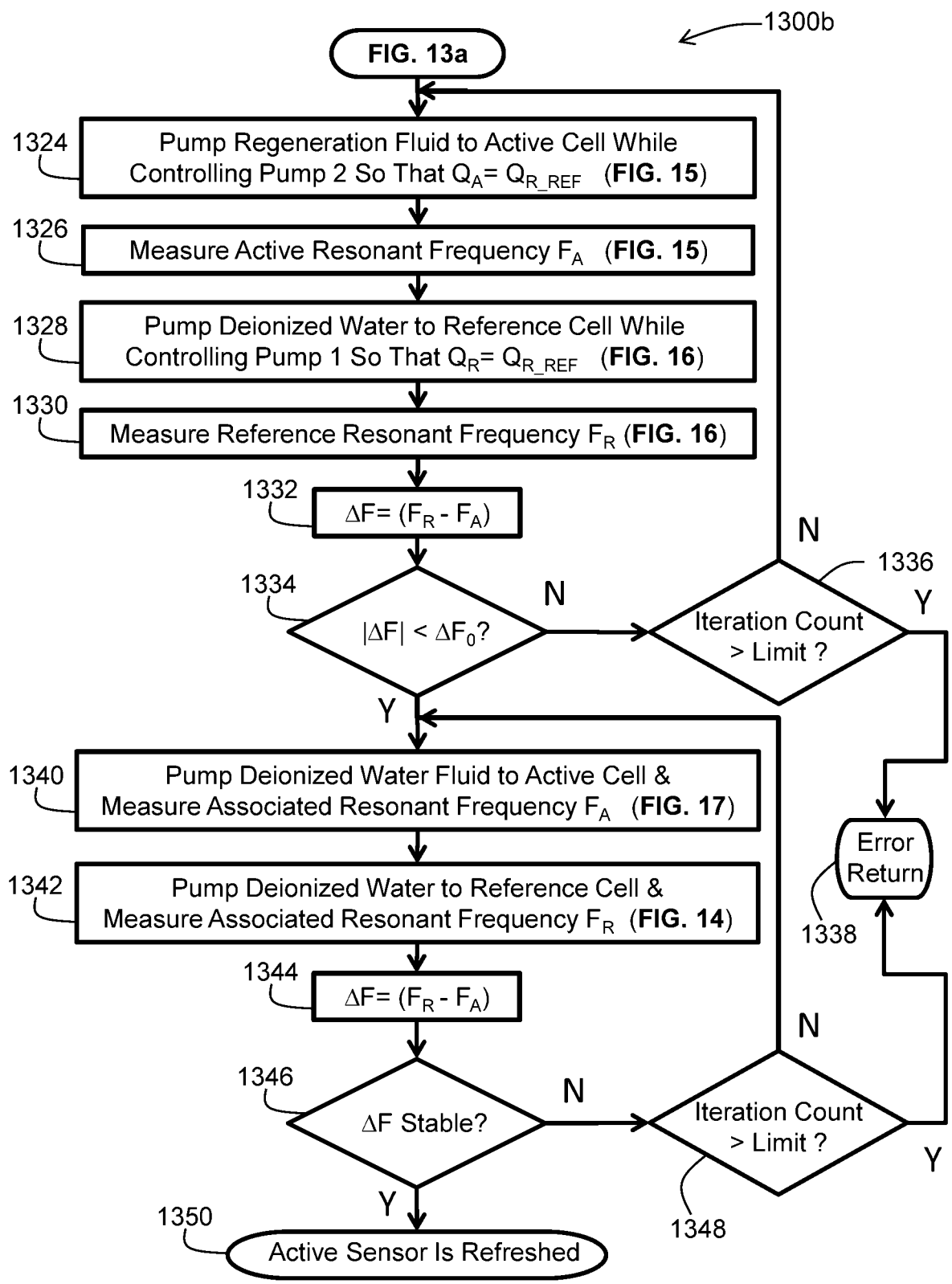
FIG. 13b illustrates a flow chart of a second phase of the process for refreshing the active sensor of a fluid contaminant sensing system.
Figure 14:
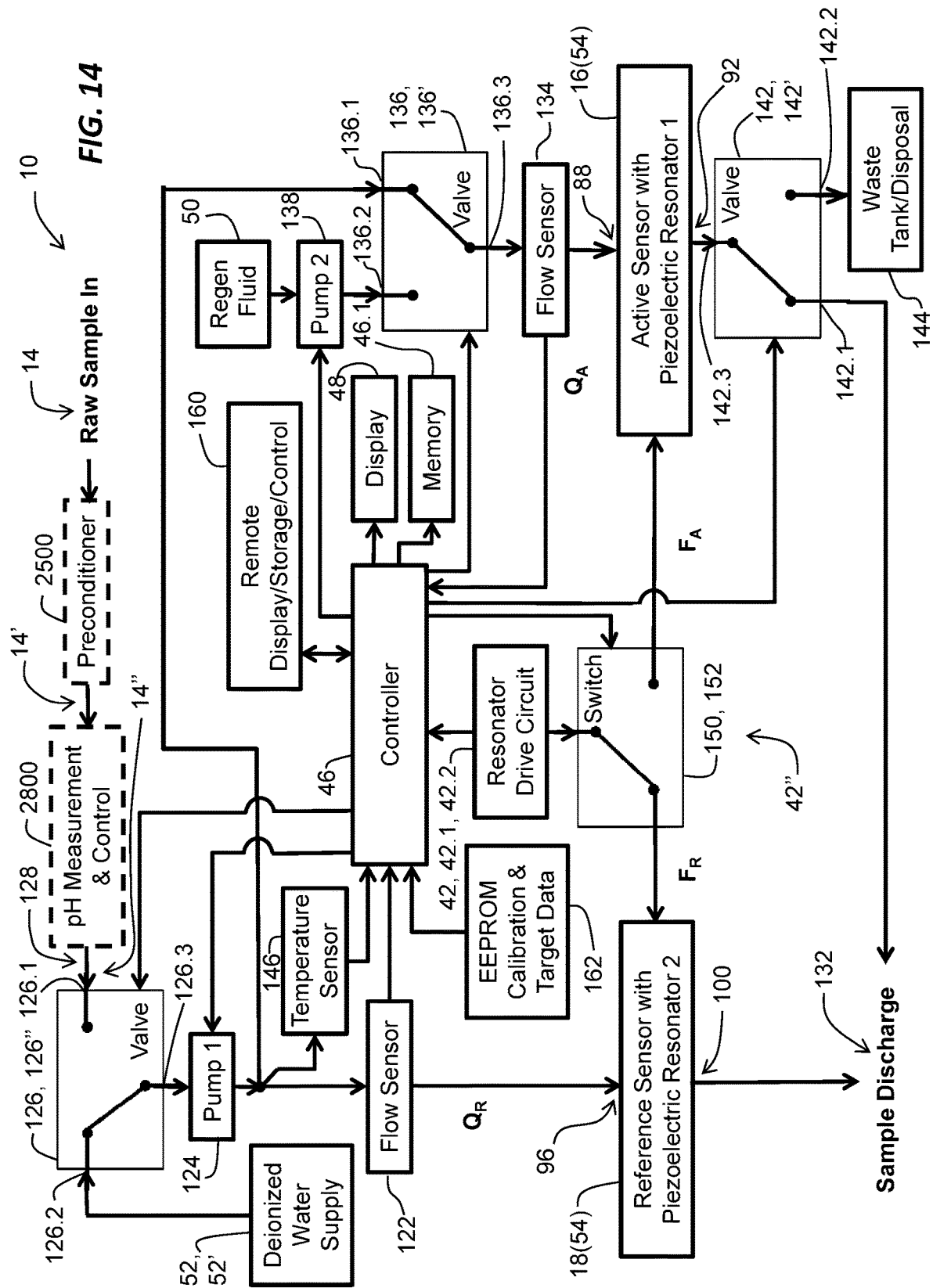
FIG. 14 illustrates a block diagram of a fluid contaminant sensing system during the associated process for refreshing the active sensor illustrated in FIGS. 13a and 13b, with the associated reference sensor being driven by the associated resonator drive circuit, with the reference sensor being used to sense an associated neutral fluid, and with the neutral fluid being pumped through the associated active sensor.

For example, FIG. 12 illustrates a typical response over time of an active sensor 16 to a calibration fluid 164 flowing therethrough, which is in particular for an active sensor 16 configured to sense phosphate in response to 0.01 mM (millimolar) phosphate (0.31 Mg/L as P) added at t=1 hour after the active sensor 16 was stabilized with 0.01 mM Tris (i.e. Trizma® (TRIS base)), wherein the pH of both solutions was approximately 5, wherein the indicated frequency difference ΔF is determined by subtracting a nominal 10 MHz from the actual measured frequency of the active piezoelectric resonator 20.1. Although the nominal resonant frequency of the piezoelectric resonator 20.1 is 10 MHz prior to coating with the associated adsorption layer 34.1, FIG. 12 also illustrates the effect of the mass of the virgin adsorption layer 34.1 in reducing the initial resonant frequency of the active piezoelectric resonator 20.1 prior to exposure to, and resulting adsorption of, target analyte 12.

Otherwise, from step (1010), if the difference between the frequency difference ΔF and the corresponding initial frequency difference $\Delta F_0$ exceeds the frequency difference threshold $\Delta F_{THRESHOLD}$, then, in step (1016), in accordance with one aspect, the remaining calibration fluid 164 that was not pumped by the first pump 124 is analyzed to determine the amount of target analyte 12 remaining therein, so as to provide for determining therefrom the amount of target analyte 12 that had been pumped by the first pump 124, which can then be used to determine the amount of target analyte 12 that had been pumped through the active sensor 16 given the above-described measure of the amount of calibration fluid 164 that had been pumped through the active sensor 16. For example, the amount of target analyte 12 remaining in the source container of calibration fluid 164 when commencing step (1016) can be measured using ICP-OES (Inductively Coupled Plasma Optical Emission Spectroscopy) or a similar apparatus.

Alternatively, or additionally, the volume of the calibration fluid 164 (albeit, sans target analyte 12) discharged from the active sensor 16 can be measured, so as to provide for determining the amount of target analyte 12 that had been adsorbed by the adsorption layer 34.1 on the first electrode 26 of the active sensor 16, given the known concentration of the target analyte 12 in the calibration fluid 164 and assuming a particular capture ratio.

Then, in step (1018), given either an associated measurement of the volume of calibration fluid 164 that had been pumped through the active sensor 16, for each corresponding measurement of frequency difference ΔF during the calibration process (1000); or assuming a linear relationship between the frequency difference ΔF and the associated amount of target analyte 12 adsorbed by the adsorption layer 34.1 on the first electrode 26 of the active sensor 16, together with the total mass of target analyte 12 adsorbed during the calibration process (1000); the amount of adsorbed target analyte 12—in molar and/or mass units—is determined for each corresponding value of frequency difference Δf', and the resulting data is stored as an associated calibration table in the EEPROM 162, over the a range of frequency differences ΔF covering at least the effective operating range (EOR).

Referring again to FIG. 2, in step (216) of process (200), following calibration of the active sensor 16 in step (214), the adsorption layer 34.1 on the first electrode 26 of the active sensor 16 is refreshed in step (216) with a regeneration fluid 50 so as to provide for cleansing the adsorption layer 34.1 on the first electrode 26 of target analyte 12, so as to restore the active piezoelectric resonator 20.1 to, or near, its initial, virgin resonant frequency. More particularly, referring to FIGS. 13a and 14, a first phase refresh process (1300a) provides for determining the flow rate $Q_R$ through the reference sensor 18 to be subsequently used to set the flow rate of the regeneration fluid 50 when refreshing the active sensor 16. In step (1302) thereof, with the first controllable three-way valve 126 in its second operating state 126", and the second 136 and third 142 controllable three-way valves in their first operating state 136', 142', a neutral fluid 52, for example, deionized water 52', is pumped by the first pump 124 to, and through, the active 16 and reference 18 sensors, and while doing so, in step (1304), the flow rate $Q_R$ through the reference sensor 18 is measured with the first flow sensor 122. Then optionally, in step (1306), the resonant frequency $F_R$ of the reference piezoelectric resonator 20.2 is measured, and, in step (1308), this valued is stored as $F_{R\_REF}$ for subsequent use. Then, in step (1310), the flow rate $Q_A$ through the active sensor 16 is measured with the second flow sensor 134, and, in step (1312), a flow rate difference ΔQ is determined as amount by which the flow rate $Q_R$ through the reference sensor 18 exceeds the flow rate $Q_A$ through the active sensor 16. If, in step (1314), the value of the flow rate difference ΔQ has not stabilized over time, or if more than two iterations of steps (1302) through (1312) have not yet been completed, then, in step (1316), if an iteration count is less than an associated limit, then the first phase refresh process (1300a) repeats, beginning with step (1302). Otherwise, from step (1316), if the associated iteration count limit has been exceeded, the first phase refresh process (1300a) terminates in step (1318) with an error as a result of an unstable flow rate.

Otherwise, from step (1314), if the value of the flow rate difference ΔQ has stabilized over time, so that the flow rate difference ΔQ does not vary by more than an associated threshold from one iteration to the next, then, in step (1320), if the absolute magnitude of the flow rate difference ΔQ is greater than a threshold $\Delta Q_{MAX}$, then the first phase refresh process (1300a) terminates in step (1318) with an error as a result of the difference between the flow rates $Q_A$, $Q_R$ through the active 16 and reference 18 sensors being greater than a correctable amount. Otherwise, from step (1320), in step (1322), the value of the flow rate $Q_R$ through the reference sensor 18 is stored as $Q_{R\_REF}$ for subsequent use.

FIGS. 13b and 14-17, a second phase refresh process (1300b) provides for cleansing the adsorption layer 34.1 on the first electrode 26 of associated target analyte 12 adsorbed thereto by pumping an associated regeneration fluid 50 through the associated active sensor 16 and across the associated adsorption layer 34.1. More particularly, following step (1322) of the first phase refresh process (1300a), in step (1324), referring to FIG. 15, with each of the first 126, second 136 and third 142 controllable three-way valves in their second operating state 126", 136", 142", the regeneration fluid 50 is pumped by the second pump 138 through the active sensor 16 while sensing the flow rate $Q_A$ thereof with the second flow sensor 134, the latter of which is used as feedback to control the flow rate of the second pump 138 so as to regulate the value of the flow rate $Q_A$ through the active sensor 16 to the previously-determined value $Q_{R\_REF}$ from step (1322). Then, in step (1326), with the resonator drive circuit 42, 42.1, 42.2 operating in its first operating state 42', the resonant frequency $F_A$ of the active piezoelectric resonator 20.1 is measured by the controller 46. Then, in step (1328), referring to FIG. 16, with the operating states 126", 136", 142" of the first 126, second 136 and third 142 controllable three-way valves unchanged, a neutral fluid 52, for example, deionized water 52', is pumped by the first pump 124 to, and through, the reference sensor 18, while sensing the flow rate $Q_R$ thereof with the first flow sensor 122, the latter of which is used as feedback to control the flow rate of the first pump 124 so as to regulate the value of the flow rate $Q_R$ through the reference sensor 18 to the previously-determined value $Q_{R\_REF}$ from step (1322), so that, accordingly, the flow rate $Q_R$ of the neutral fluid 52, 52' through the reference sensor 18 is the same as the flow rate $Q_A$ of the regeneration fluid 50 through the active sensor 16. Then, in step (1330), with the resonator drive circuit 42, 42.1, 42.2 operating in its second operating state 42", the resonant frequency $F_R$ of the reference piezoelectric resonator 20.2 is measured by the controller 46.

Then, in step (1332), a frequency difference ΔF is determined as amount by which the resonant frequency $F_R$ of the reference piezoelectric resonator 20.2 exceeds the resonant frequency $F_A$ of the active piezoelectric resonator 20.1. Then, in step (1334), if the absolute magnitude of the frequency difference 1F is not less than a corresponding threshold frequency difference $ΔF_0$, then, in step (1336), if an iteration count is less than an associated limit, then the second phase refresh process (1300b) repeats, beginning with step (1324). Otherwise, from step (1336), if the associated iteration count limit has been exceeded, the second phase refresh process (1300b) terminates in step (1338) with an error as a result of an inability to sufficiently cleanse the active sensor 16 of target analyte 12.

Figure 17:
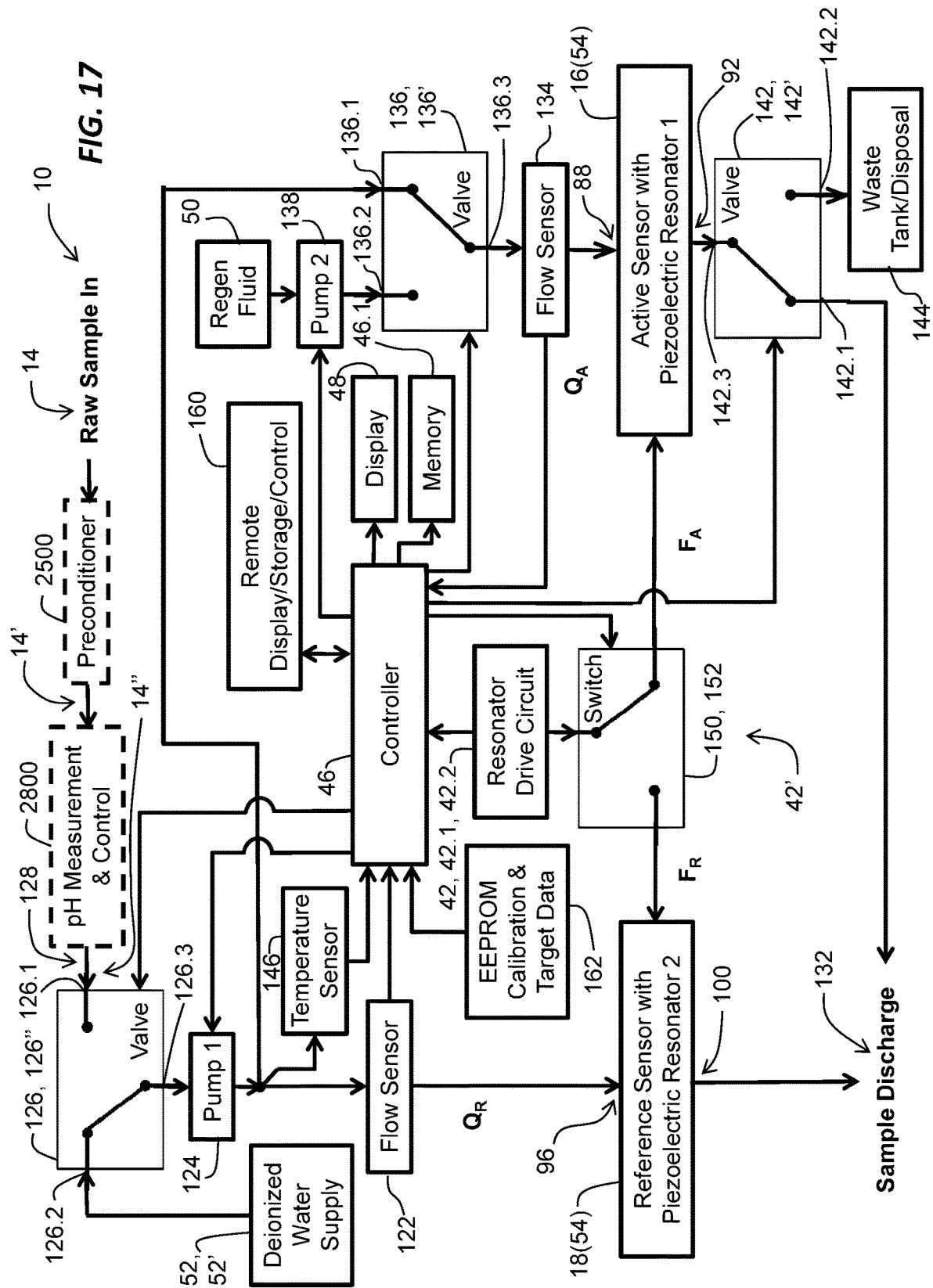
FIG. 17 illustrates a block diagram of the fluid contaminant sensing system during the associated process for refreshing the active sensor, with the associated active sensor being driven by the associated resonator drive circuit, and with the active sensor being used to sense the neutral fluid.

Otherwise, from step (1334), if the absolute magnitude of the frequency difference ΔF is less than the corresponding threshold frequency difference $ΔF_0$, —indicating that the active sensor 16 has been sufficiently cleansed of target analyte 12, —then, in step (1340), referring to FIG. 17, with the first controllable three-way valve 126 in its second operating state 126", and the second 136 and third 142 controllable three-way valves in their first operating state 136', 142', the neutral fluid 52, 52', is pumped by the first pump 124 to, and through, the active 16 and reference 18 sensors, and with the resonator drive circuit 42, 42.1, 42.2 operating in its first operating state 42', the resonant frequency $F_A$ of the active piezoelectric resonator 20.1 is measured by the controller 46. Then in step (1342), referring again to FIG. 14, with the operating states 126", 136', 142' of the first 126, second 136 and third 142 controllable three-way valves unchanged, but with the resonator drive circuit 42, 42.1, 42.2 operating in its second operating state 42', the resonant frequency $F_R$ of the reference piezoelectric resonator 20.2 is measured by the controller 46. Then, in step (1344), a frequency difference ΔF is determined as amount by which the resonant frequency $F_R$ of the reference piezoelectric resonator 20.2 exceeds the resonant frequency $F_A$ of the active piezoelectric resonator 20.1.

If, in step (1346), the value of the frequency difference ΔF has not stabilized over time, or if more than two iterations of steps (1340) through (1344) have not yet been completed, then, in step (1348), if an iteration count is less than an associated limit, then the second phase refresh process (1300b) repeats, beginning with step (1340). Otherwise, from step (1348), if the associated iteration count limit has been exceeded, the second phase refresh process (1300b) terminates in step (1338) with an error because the active sensor 16 is not sufficiently stable. Otherwise, from step (1346), if the value of the frequency difference ΔF has stabilized over time, so that the frequency difference ΔF does not vary by more than an associated threshold from one iteration to the next, then, in step (1350), the second phase refresh process (1300b) terminates without error, with the active sensor 16 refreshed.

Figure 18:
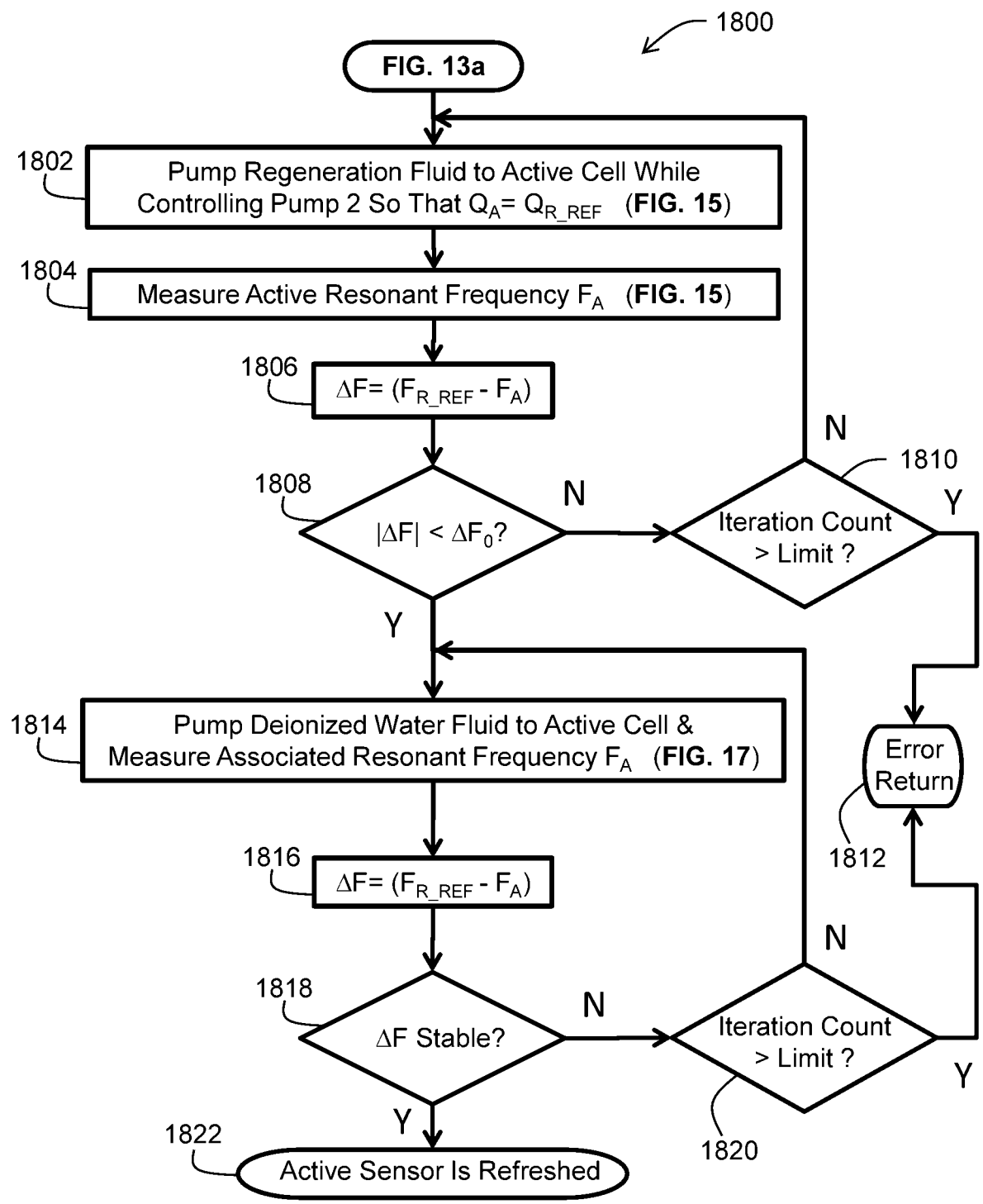
FIG. 18 illustrates a flow chart of an alternative second portion of the process for refreshing the active sensor of a fluid contaminant sensing system.

Referring to FIG. 18, an alternative second phase refresh process (1800) also provides for cleansing the adsorption layer 34.1 on the first electrode 26 of associated target analyte 12 adsorbed thereto by pumping an associated regeneration fluid 50 through the associated active sensor 16 and across the associated adsorption layer 34.1.

Figure 15:
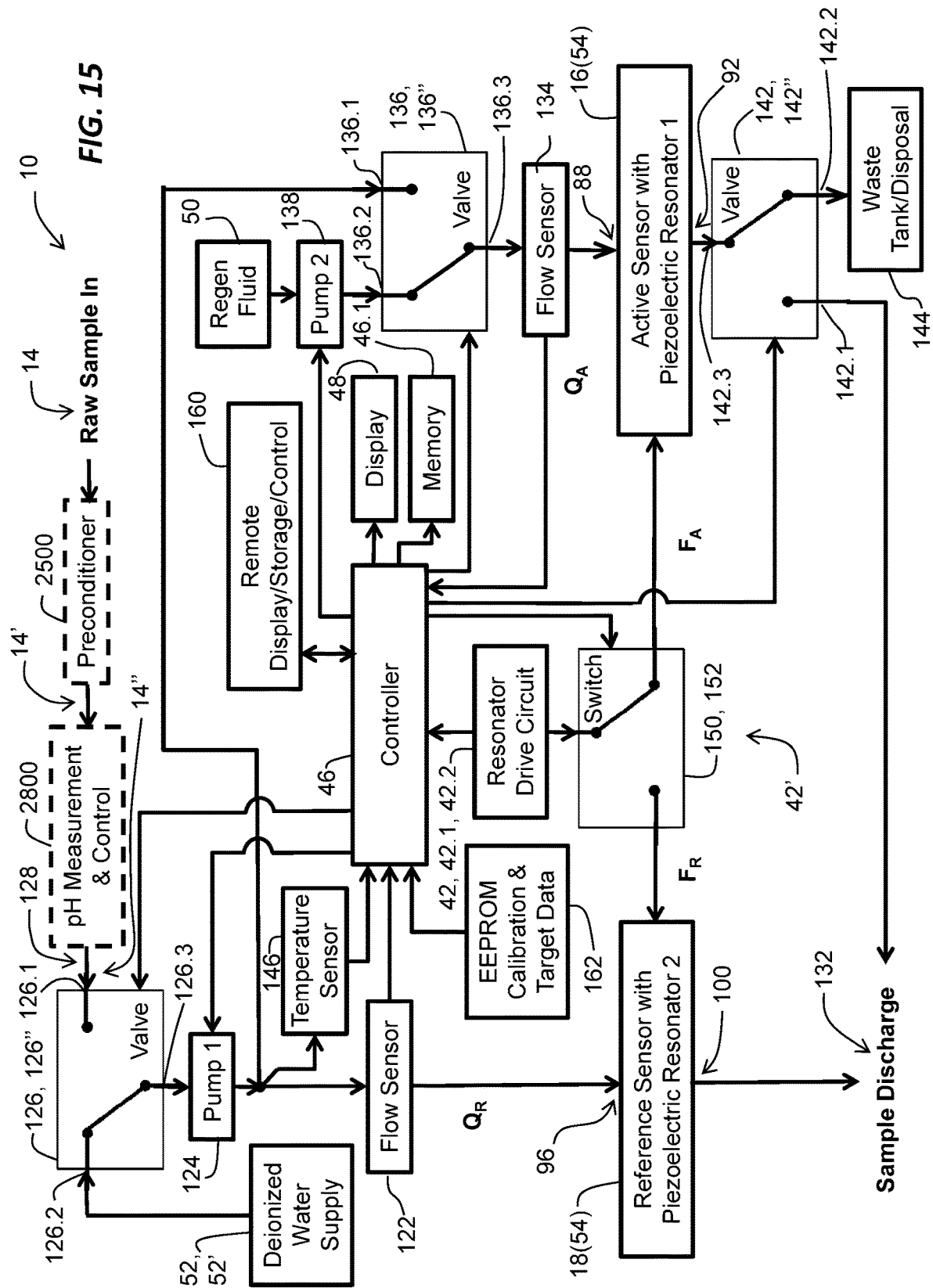
FIG. 15 illustrates a block diagram of the fluid contaminant sensing system during the associated process for refreshing the active sensor corresponding to FIG. 14, but with the associated active sensor being driven by the associated resonator drive circuit, and with the active sensor being refreshed by and used to sense an associated regeneration fluid.
Figure 16:
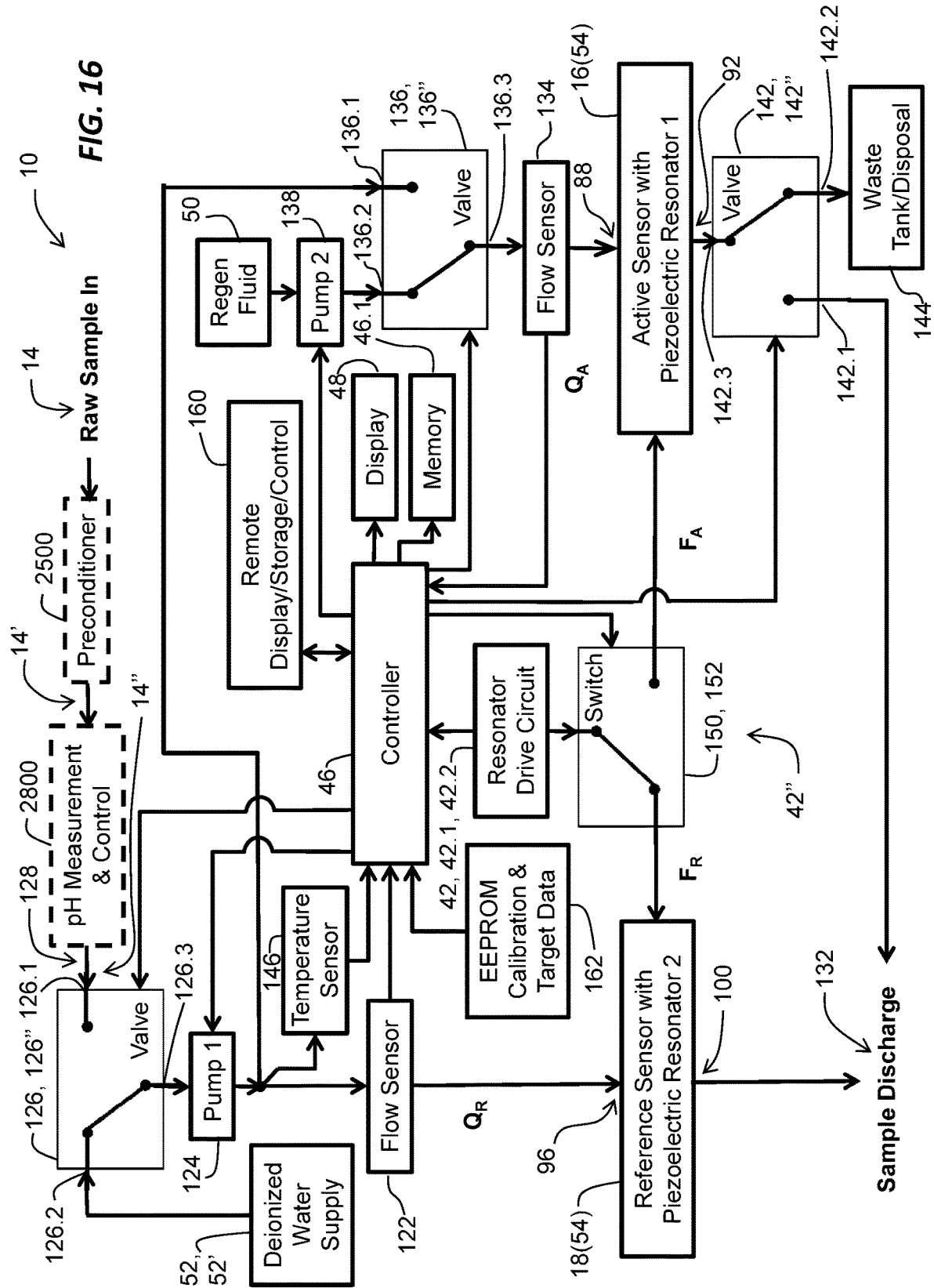
FIG. 16 illustrates a block diagram of the fluid contaminant sensing system during the associated process for refreshing the active sensor corresponding to FIG. 15, but with the associated reference sensor being driven by the associated resonator drive circuit, and with the reference sensor being used to sense the neutral fluid.

More particularly, following step (1322) of the first phase refresh process (1300a), in step (1802), referring to FIG. 15, with each of the first 126, second 136 and third 142 controllable three-way valves in their second operating state 126", 136", 142", the regeneration fluid 50 is pumped by the second pump 138 through the active sensor 16 while sensing the flow rate $Q_A$ thereof with the second flow sensor 134, the latter of which is used as feedback to control the flow rate of the second pump 138 so as to regulate the value of the flow rate $Q_A$ through the active sensor 16 to the previously-determined value $Q_R$ REF from step (1322). Then, in step (1804), with the resonator drive circuit 42, 42.1, 42.2 operating in its first operating state 42', the resonant frequency $F_A$ of the active piezoelectric resonator 20.1 is measured by the controller 46.

Then, in step (1806), a frequency difference ΔF is determined as amount by which the stored resonant frequency $F_{R\_REF}$ of the reference piezoelectric resonator 20.2—stored in step (1322)—exceeds the resonant frequency $F_A$ of the active piezoelectric resonator 20.1.

Then, in step (1808), if the absolute magnitude of the frequency difference ΔF is not less than a corresponding threshold frequency difference $ΔF_0$, then, in step (1810), if an iteration count is less than an associated limit, then the alternative second phase refresh process (1800) repeats, beginning with step (1802). Otherwise, from step (1810), if an iteration count is less than an associated limit, the second phase refresh process (1300b) terminates in step (1812) with an error as a result of an inability to sufficiently cleanse the active sensor 16 of target analyte 12.

Otherwise, from step (1808), if the absolute magnitude of the frequency difference ΔF is less than the corresponding threshold frequency difference $ΔF_0$, —indicating that the active sensor 16 has been sufficiently cleansed of target analyte 12, —then, in step (1814), referring to FIG. 17, with the first controllable three-way valve 126 in its second operating state 126", and the second 136 and third 142 controllable three-way valves in their first operating state 136', 142', the neutral fluid 52, 52', is pumped by the first pump 124 to, and through, the active 16 and reference 18 sensors, and with the resonator drive circuit 42, 42.1, 42.2 operating in its first operating state 42', the resonant frequency $F_A$ of the active piezoelectric resonator 20.1 is measured by the controller 46. Then, in step (1816), a frequency difference ΔF is determined as amount by which the stored resonant frequency $F_{R\_REF}$ of the reference piezoelectric resonator 20.2 exceeds the resonant frequency $F_A$ of the active piezoelectric resonator 20.1.

If, in step (1818), the value of the frequency difference ΔF has not stabilized over time, or if more than two iterations of steps (1814) and (1816) have not yet been completed, then, in step (1820), if an iteration count is less than an associated limit, then the alternative second phase refresh process (1800) repeats, beginning with step (1814). Otherwise, from step (1820), if the associated iteration count limit has been exceeded, the alternative second phase refresh process (1800) terminates in step (1812) with an error because the active sensor 16 is not sufficiently stable. Otherwise, from step (1818), if the value of the frequency difference ΔF has stabilized over time, so that the frequency difference ΔF does not vary by more than an associated threshold from one iteration to the next, then, in step (1822), the alternative second phase refresh process (1800) terminates without error, with the active sensor 16 refreshed.

Referring again to FIG. 2, following the refresh of the active sensor 16 in step (214), —with the active piezoelectric resonator 20.1 restored to, or near, its initial, virgin resonant frequency, —in step (218), the fluid contaminant sensing system 10 is ready for continuous operation in accordance with a continuous sensing process (1900), which commences in step (1902) with the initialization of variables $V_{SAMPLE}$ and $M_{TARGET}$ that respectively contain the total volume of the sample fluid 14 that had been pumped through the active sensor 16, and the total mass of the target analyte 12 in that total volume of the sample fluid 14, sensed by the active sensor 16, both of which are relative to commencement of the continuous sensing process (1900). In step (1904), a sensing cycle starting time t0 is initialized to the current time t, so as to provide for determining the duration of the associated sensing cycle of steps (1906) through (1922) prior to step (1924), following the regeneration of the active sensor 16 by the associated refresh processes (1300a) and (1300b or 1800).

Then, in step (1906), the sample fluid 14 is optionally preconditioned—for example, by a below-describe preconditioning process (2400)—to mechanically filter the sample fluid 14, and to possibly remove either cations or anions therefrom depending upon the nature of the associated adsorption material 34' of the adsorption layer 34.1 on the first electrode 26 of the active sensor 16, for example, so as to provide for removing gross contamination, biofouling, organic molecules, cations or anions that might otherwise interfere with the active 16 or reference 18 sensors. Then, in step (1908), the pH of the raw or optionally preconditioned sample fluid 14 is optionally monitored and controlled—for example, by a below-describe pH control process (2700)—for example, so as to provide for adsorption of the target analyte 12 by the adsorption material 34' of the adsorption layer 34.1 on the first electrode 26 of the active sensor 16, depending upon the particular target analyte 12.

Figure 20:
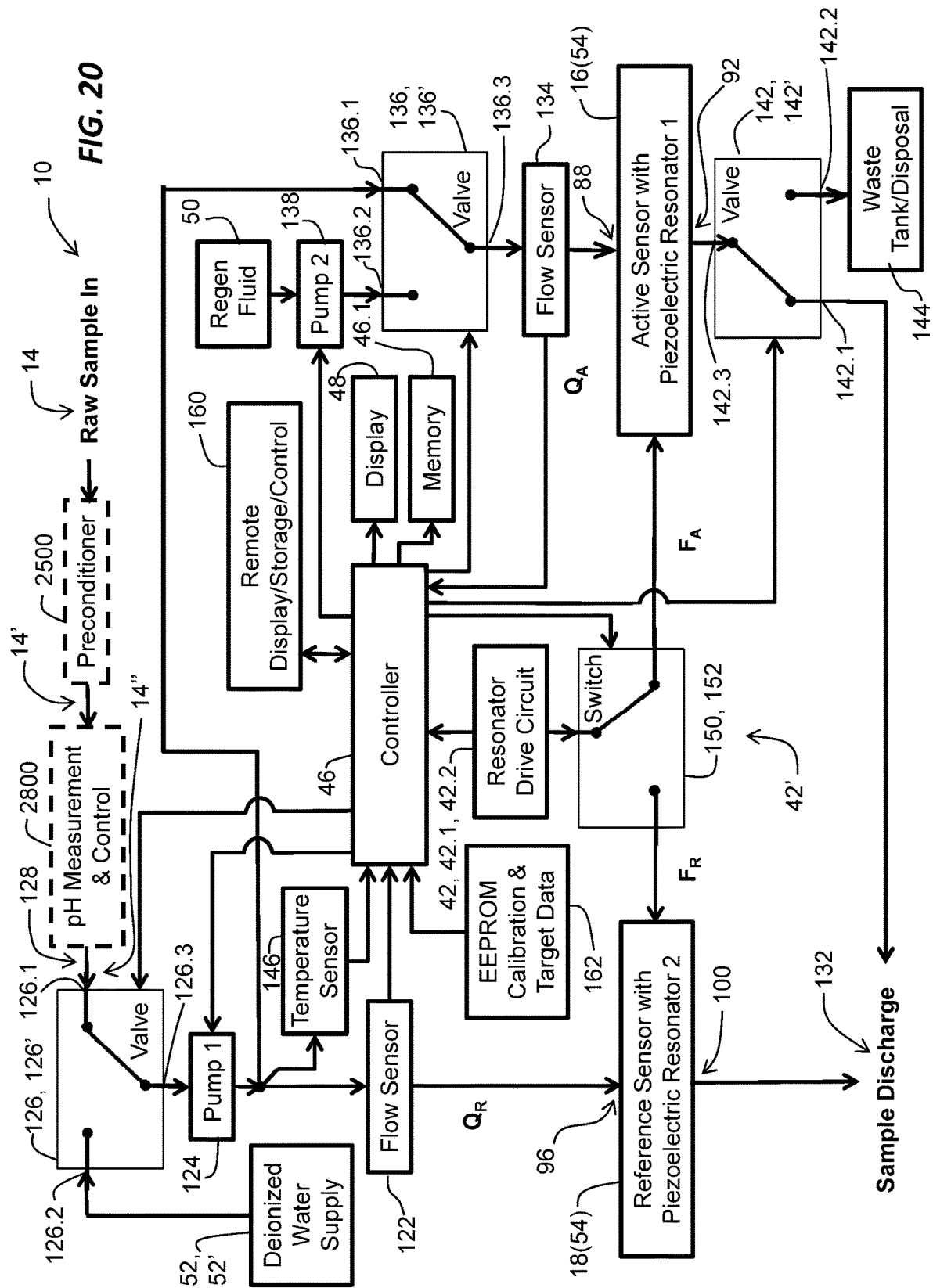
FIG. 20 illustrates a block diagram of a fluid contaminant sensing system during the associated continuous sensing process illustrated in FIG. 19, with the associated active sensor being driven by the associated resonator drive circuit.

Then, referring to FIG. 20, in step (1910), the first pump 124 is activated to pump the sample fluid 14 through the first cavity 38 of the active sensor 16, with the associated first 126, second 136 and third 142 controllable three-way valves each in its corresponding first operating state 126', 136', 142', and measuring the resonant frequency of the active piezoelectric resonator 20.1 with the resonator drive circuit 42, 42.1, 42.2 operating in the first operating state 42' thereof. The flow rate of the first pump 124 is sufficiently slow—for example, about 0.5 ml/minute—so as to provide for sufficient residence time within the first cavity 38 for nearly all of the target analyte 12 therein to become adsorbed by the adsorption layer 34.1 on the first electrode 26 of the active sensor 16, i.e. so that the associated capture ratio of the target analyte 12 ions or species to the associated chemical receptor binding sights of the associated adsorption material 34' is at least nearly 100%.

Figure 21:
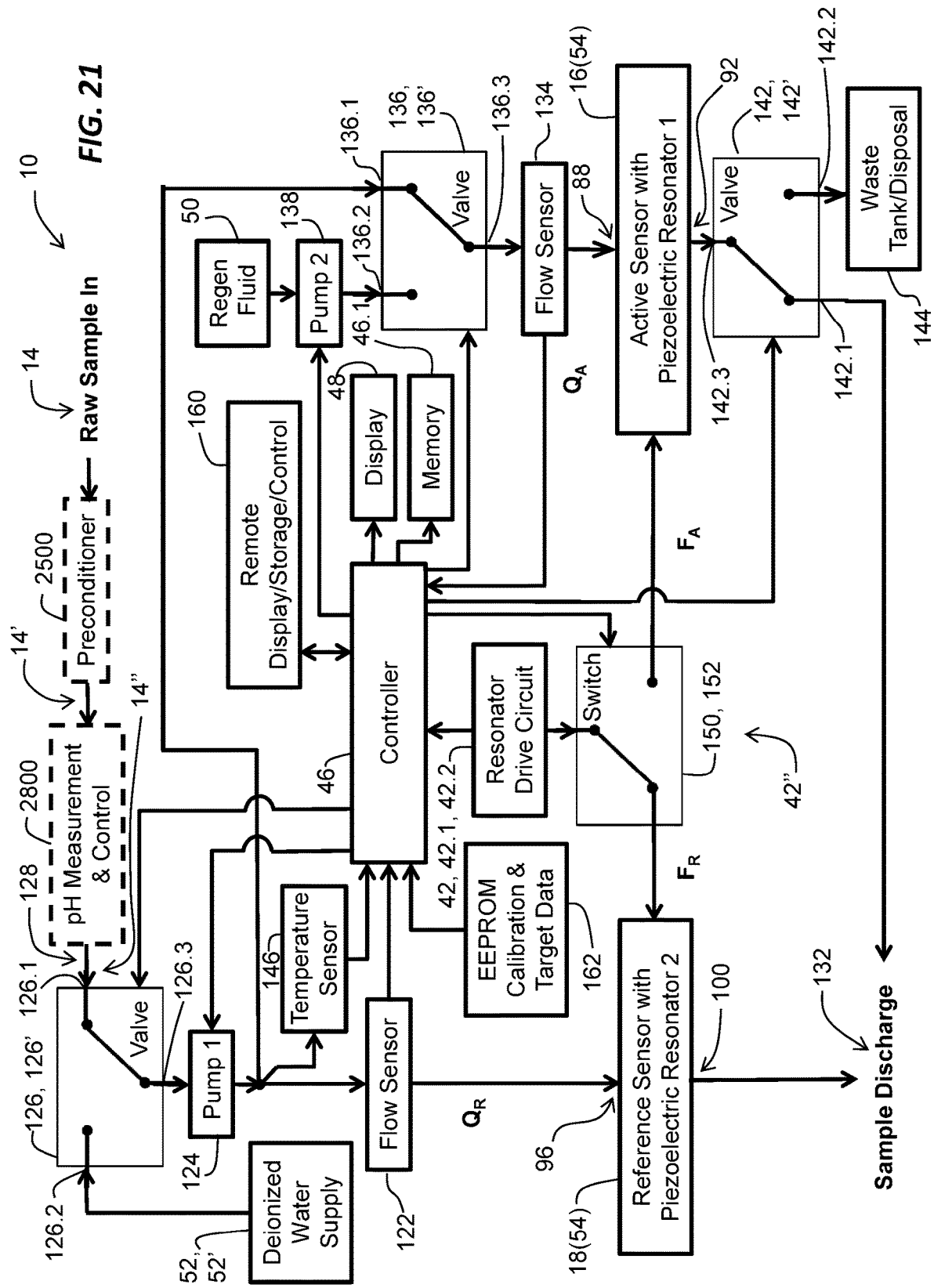
FIG. 21 illustrates a block diagram of a fluid contaminant sensing system during the associated continuous sensing process illustrated in FIG. 19, corresponding to FIG. 20, but with the associated reference sensor being driven by the associated resonator drive circuit.

Then, referring to FIG. 21, in step (1912), the sample fluid 14 is also pumped by the first pump 124 through the second cavity 40 of the reference sensor 18, without changing the operating states 126', 136', 142' of the first 126, second 136 and third 142 controllable three-way valves, but with the resonator drive circuit 42, 42.1, 42.2 operating in the second operating state 42" so as to provide for measuring the resonant frequency of the reference piezoelectric resonator 20.2.

Then, in step (1914), a frequency difference $\Delta F$ is determined as the difference between the resonant frequencies $F_R$ and $F_A$ of the active 20.1 and reference 20.2 piezoelectric resonators, respectively. Then, in step (1916), the mass of the target analyte 12 adsorbed by the adsorption layer 34.1 on the first electrode 26 of the active sensor 16 is determined responsive to the difference between the frequency difference $\Delta F$ of step (1914) and a corresponding initial frequency difference $\Delta F_0$ that is stored after refreshing the active sensor 16, using the calibration data stored on the EEPROM 162.

Then, in step (1918), the total flow of the sample fluid 14 is determined either from 1) a direct measurement from the second flow sensor 134 of the flow rate through the first cavity 38 over an associated period of time; 2) an inference of the flow rate through the first cavity 38 through the first cavity 38 given a predetermined rate of flow of the first pump 124 assuming a given distribution of flow from the first pump 124 to the first 38 and second 40 cavities or from a determination of the distribution of flow using flow rate measurements from the first 122 and second 134 flow sensors; or 3) of the flow rate through the first cavity 38 through the first cavity 38 given a predetermined rate of flow of the first pump 124 if the fluid contaminant sensing system 10 is configured in accordance with alternative topologies of FIG. 22 or 23, described hereinbelow.

The, in step (1920), the total volume of sample $\Delta V_{SAMPLE}$ that has been pumped through the active sensor 16 since commencement of the most recent sensing cycle is determined responsive to the flow that was measured or determined in step (1918), which is either explicitly or implicitly responsive to the duration of time ($t-t_0$) of the most recent sensing cycle.

Then, in step (1922), the current measurements form the fluid contaminant sensing system 10 are either stored, displayed on a local display 48, or transmitted to a remote display, storage or control system 160.

Then, in step (1924), if the magnitude of the difference between frequency difference $\Delta F$ from step (1914) and a corresponding initial frequency difference $\Delta F_0$ does not exceed a threshold frequency difference $\Delta F_{EOR}$ associated with the effective operating range (EOR) of the active sensor 16, then the particular sensing cycle continues by repeating the continuous sensing process (1900) beginning with step (1906).

Otherwise, from step (1924), in step (1926), the active sensor 16 is regenerated in accordance with the associated refresh processes (1300a) and (1300b or 1800), after which, in step (1926), the values of the total volume $V_{SAMPLE}$ of the sample fluid 14 that had been pumped through the active sensor 16, and the total mass $M_{TARGET}$ of the target analyte 12 in that total volume of the sample fluid 14, are updated to include the corresponding amounts $\Delta V_{SAMPLE}$, $\Delta M_{TARGET}$ had been sensed in the most recent sensing cycle, after which a new sensing cycle commences by repeating the continuous sensing process (1900) beginning with step (1904).

Referring to FIGS. 22 and 23, the topology of the plumbing of the fluid contaminant sensing system 10 may be modified with the addition of a fourth controllable three-way valve 166, an inlet port 166.3 of which is operatively coupled to the output of the first pump 124, a first outlet port 166.1 of which is operatively coupled, either directly or indirectly, to the first inlet port 88 of the active sensor 16, a second outlet port 166.2 of which is operatively coupled to the second inlet port 96 of the reference sensor 18. In a first operating state 166' of the third controllable three-way valve 166, the first outlet port 166.1 thereof is operatively coupled to the inlet port 166.3 thereof, so as to provide for exclusively discharging the fluid from the first pump 124 to the first inlet port 88 of the active sensor 16. In a second operating state 166" of the third controllable three-way valve 166, the second outlet port 166.2 thereof is operatively coupled to the inlet port 166.3 thereof, so as to provide for exclusively discharging the fluid from the first pump 124 to the second inlet port 96 of the reference sensor 18. Accordingly, with the fourth controllable three-way valve 166 in the first 166' or second 166" operating states, respectively, the corresponding flow rates through the active 16 and reference 18 sensors, respectively will be the same as the predetermined flow rate of the positive displacement first pump 124, so as to provide for determining the flow rate $Q_A$ without using an associated second flow sensor 134.

More particularly, referring to FIG. 22, in accordance with a first alternative topology for suppling fluid to the active 16 and reference 18 sensors, the first outlet port 166.1 of the fourth controllable three-way valve 166 is operatively coupled to the first inlet port 136.1 of the second controllable three-way valve 136, the latter of which otherwise functions as described hereinabove.

Referring to FIG. 23, in accordance with a second alternative topology for suppling fluid to the active 16 and reference 18 sensors, the first outlet port 166.1 of the fourth controllable three-way valve 166 is operatively coupled to an inlet 168.1 of a first check valve 168, the outlet 168.2 of which is operatively coupled to the first inlet port 88 of the active sensor 16, wherein the first check valve 168 provides for flow from the inlet 168.1 thereof to the outlet 168.2 thereof, but not in a reverse direction. Furthermore, the outlet of the second pump 138 is operatively coupled to an inlet 170.1 of a second check valve 170, the outlet 170.2 of which is operatively coupled to the first inlet port 88 of the active sensor 16, wherein the second check valve 170 provides for flow from the inlet 170.1 thereof to the outlet 170.2 thereof, but not in a reverse direction. Accordingly, when the second pump 138 is in operation, the first check valve 168 prevents a backflow of regeneration fluid 50 upstream thereof, and the second check valve 170 prevents a backflow of sample fluid 14 upstream thereof. In an alternative embodiment, the first check valve 168 could possibly be eliminated if the fourth controllable three-way valve 166 was operated in the second operating state 166" whenever the second pump 138 is activated.

Figure 19:
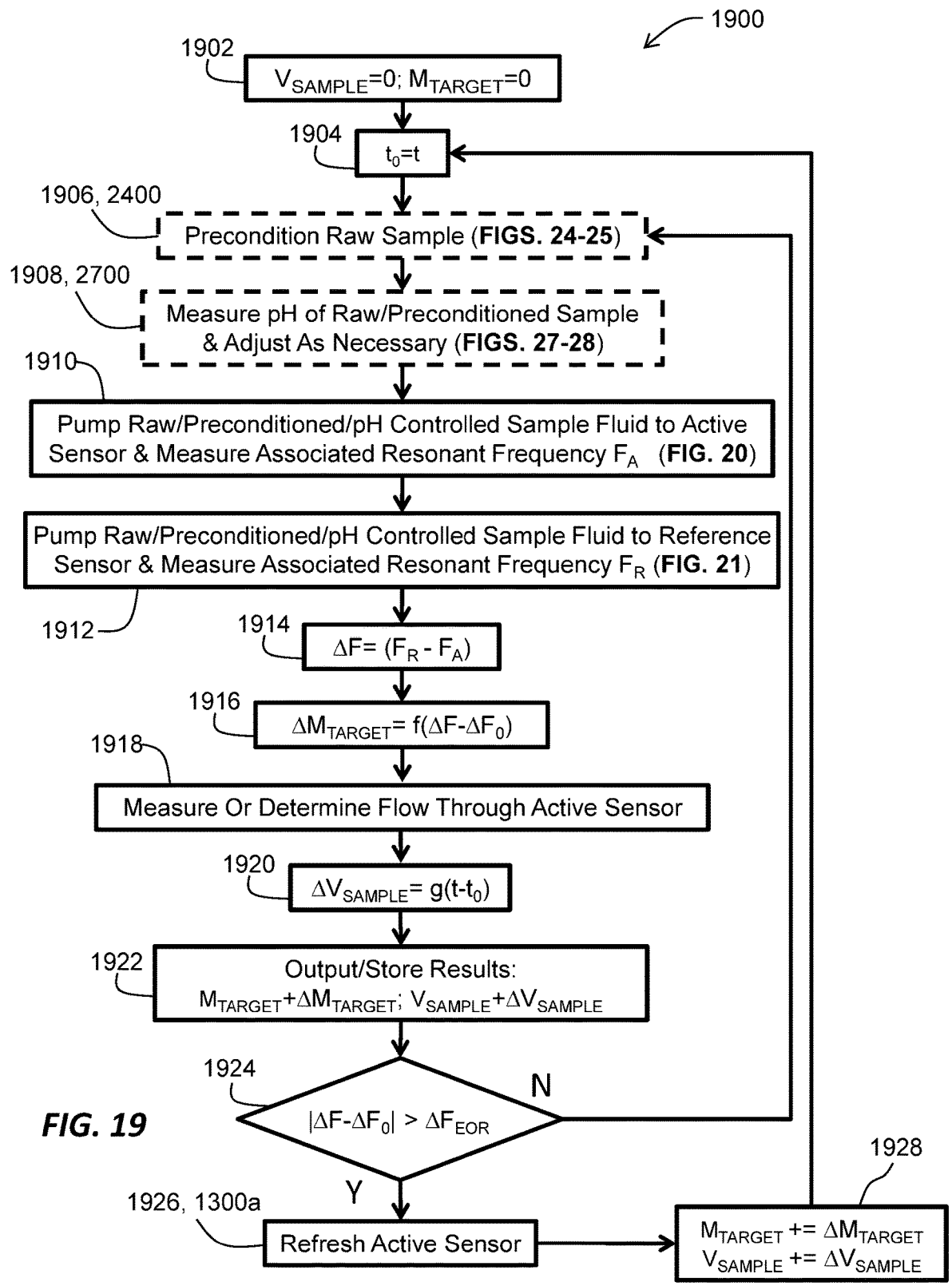
FIG. 19 illustrates a flow chart of an associated continuous sensing process.
Figure 24:
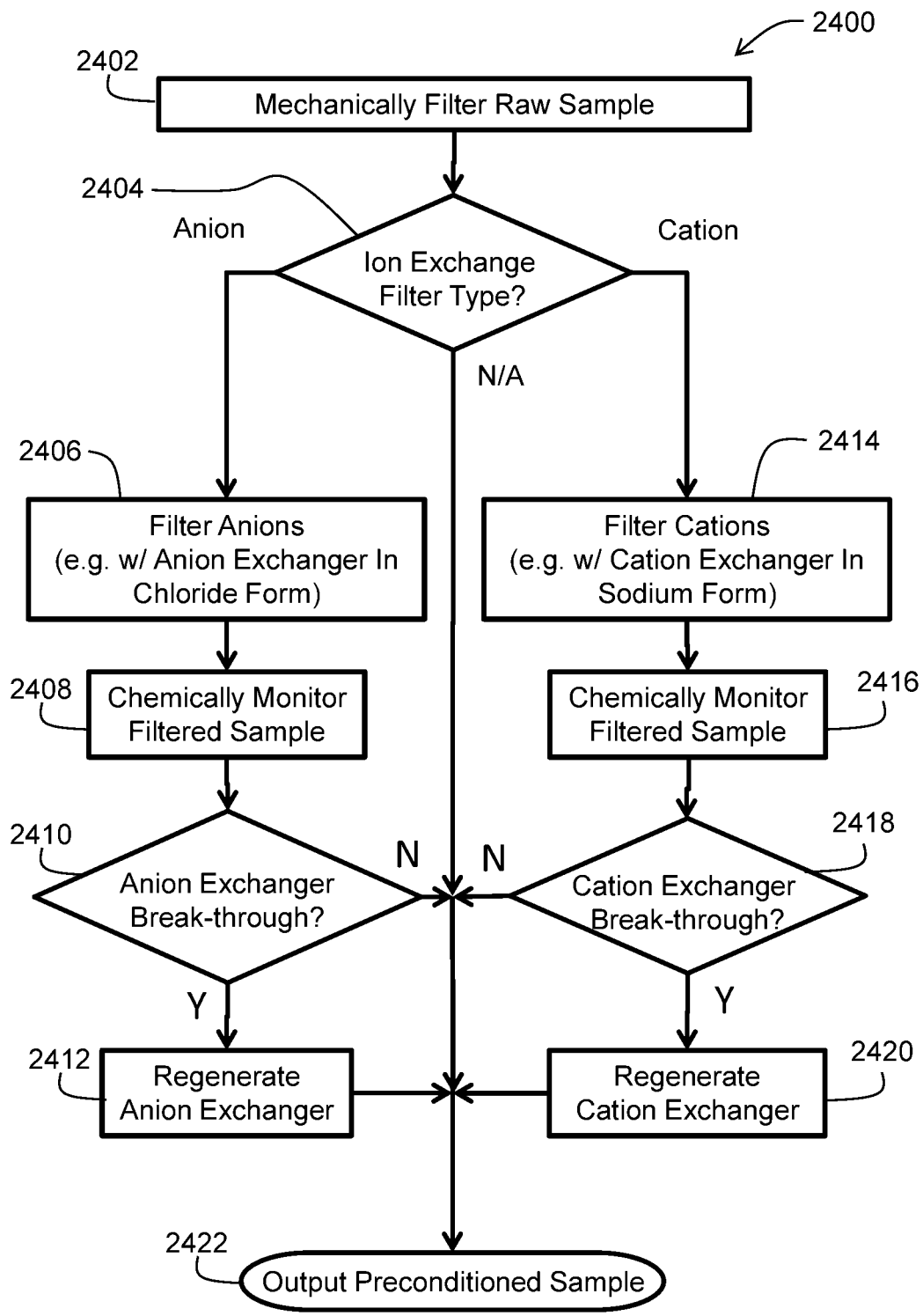
FIG. 24 illustrates a flow chart of a preconditioning process of a preconditioner of the associated fluid contaminant sensing system, and associated process, illustrated in FIGS. 19-21.

Referring to FIG. 24, in accordance with optional step (1906) of the continuous sensing process (1900) illustrated in FIG. 19, and with reference to FIGS. 20 and 21, a preconditioning process (2400) provides for removing chemical interferences, including non-target ions, molecules, microorganisms, or other substances from the raw sample fluid 14, which might otherwise bind to the adsorption material 34' of the adsorption layer 34.1 on the first electrode 26 of the active sensor 16, and thereby adversely increase the mass, and decrease the resonant frequency, thereof, which could lead to a false indication of the presence of a corresponding amount of target analyte 12 in the sample fluid 14, but while leaving the target analyte 12 intact so as to not interfere with the detection thereof by the active sensor 16, for example, in situations for which the adsorption material 34' is not selective for the target analyte 12. For example, in some applications, such as a post-treatment monitor at the back end of a treatment column, the column itself may remove the potential interferences, so as to preclude the need for otherwise preconditioning the sample fluid 14. Otherwise, a selective receptor will obviate the need for upstream removal of potentially competing chemical interferences. In applications for which there is a potential response from chemical interferences, these may be removed upstream from the sample flow by the preconditioning process (2400), which is a hierarchical process that considers gross contamination, biofouling, organic molecules, cations and anions. Means for removing these may be configured into separation modules that are positioned upstream from the monitor Referring also to FIG. 25, the preconditioning process (2400) is implemented with a preconditioner 2500—also referred to as a separations module—that receives the raw sample fluid 14 prior to subsequent processing by the fluid contaminant sensing system 10. Beginning with step (2402) of the preconditioning process (2400), the raw sample fluid 14 is mechanically filtered by an associated mechanical filter 172, which removes gross contamination and biofouling from the raw sample fluid 14. The preconditioner 2500 would typically be used—depending upon the type of target analyte 12—to filter either anions or cations, but not both for any one type of fluid contaminant sensor cell 54, i.e. for any particular type of adsorption material 34'.

Accordingly, following step (2402), in step (2404), if anions are to be filtered, then, in step (2406), the discharge from the mechanical filter 172 is passed through a first controllable three-way valve 174 (controlled by the controller 46) in a first operating state 174' to an anion filter 176, for example, an anion exchange filter 176' (also referred to as an anion column) in chloride form, the output of which is discharged through a first chemical monitor 178, and through a second controllable three-way valve 180 (controlled also by the controller 46) in a first operating state 180', and then discharged from the preconditioner 2500 as the associated preconditioned sample fluid 14'.

In step (2408), the first chemical monitor 178 provides for detecting if there has been a breakthrough from the anion filter 176 of anions from the sample fluid 14 that have been captured by the anion filter 176. More particularly, in one embodiment, the first chemical monitor 180 comprises a quartz-crystal microbalance (QCM) 56 configured as an active piezoelectric resonator 20.1, with the associated adsorption material 34' of the adsorption layer 34.1 configured as an anion exchanger that is doped, or saturated, with an anion of lower selectivity than the anion to be removed by the anion filter 176, 176'. For example, if As(III) is the cation that may interfere, then the associated adsorption material 34' of the adsorption layer 34.1 could be doped, or saturated, with chloride, Cl. If As(III) breaks through the anion filter 176, 176', then the As(III) will displace the Cl on the adsorption layer 34.1 of the associated first electrode 26 of the active piezoelectric resonator 20.1, and the resultant frequency response, i.e. lowered resonant frequency, will indicate the breakthrough.

If, in step (2410), a break-through has been detected by the first chemical monitor 178, then in step (2412), referring also to FIG. 26, the anion filter 176, 176' is then refreshed by passing a salt solution [NaCl]—as a first regeneration fluid 182—through the anion filter 176, 176', wherein, with the first 174 and second 180 controllable three-way valves each in a corresponding, respective second operating state 174", 180", the first regeneration fluid 182 is pumped by a first pump (Pump A) 184 through the anion filter 176, 176'. This refresh process will also refresh the adsorption layer 34.1 of the active piezoelectric resonator 20.1 of the first chemical monitor 178, by displacing the bound As(III) with Cl, wherein the frequency difference of the first chemical monitor 178 will the indicate when the associated refresh process is complete.

Similarly, following step (2402), in step (2404), if cations are to be filtered, then, in step (2414), the discharge from the mechanical filter 172 is passed through a third controllable three-way valve 186 (controlled by the controller 46) in a first operating state 186' to an anion filter 176, for example, an cation exchange filter 188' (also referred to as an cation column) in sodium form, the output of which is discharged through a second chemical monitor 190, and through a second controllable three-way valve 192 (controlled also by the controller 46) in a first operating state 192', and then discharged from the preconditioner 2500 as the associated preconditioned sample fluid 14'.

In step (2416), the second chemical monitor 190 provides for detecting if there has been a breakthrough from the cation filter 188 of anions from the sample fluid 14 that have been captured by the cation filter 188. More particularly, in one embodiment, the first chemical monitor 192 comprises a quartz-crystal microbalance (QCM) 56 configured as an active piezoelectric resonator 20.1, with the associated adsorption material 34' of the adsorption layer 34.1 configured as a cation exchanger that is doped, or saturated, with an cation of lower selectivity than the cation to be removed by the cation filter 188, 188', for example, in accordance with the following table of selectivity:

| Species | Cation | Selectivity Coefficient |
|---|---|---|
| hydrogen | $H^+$ | 1.0 |
| sodium | $Na^+$ | 2.0 |
| iron | $Fe^{2+}$ | 2.9 |
| zinc | $Zn^{2+}$ | 3.0 |
| cadmium | $Cd^{2+}$ | 3.95 |
| calcium | $Ca^{2+}$ | 5.8 |
| strontium | $Sr^{2+}$ | 8.1 |
| copper | $Cu^{2+}$ | 14.5 |
| mercury | $Hg^{2+}$ | 14.0 |
| lead | $Pb^{2+}$ | 14.5 |

For example, if Hg is the cation that may interfere, then the associated adsorption material 34' of the adsorption layer 34.1 could be doped, or saturated, with, for example, sodium, Na. If Hg breaks through the cation filter 188, 188', then the Hg will displace the Na on the adsorption layer 34.1 of the associated first electrode 26 of the active piezoelectric resonator 20.1, and the resultant frequency response, i.e. lowered resonant frequency, will indicate the breakthrough.

If, in step (2418), a break-through has been detected by the second chemical monitor 190, then in step (2420), referring also to FIG. 26, the cation filter 188, 188' is then refreshed by passing a salt solution [NaCl]—as a second regeneration fluid 194—through the cation filter 188, 188', wherein, with the first 186 and second 192 controllable three-way valves each in a corresponding, respective second operating state 186", 192", the second regeneration fluid 194 is pumped by a second pump (Pump B) 196 through the cation filter 188, 188'. This refresh process will also refresh the adsorption layer 34.1 of the active piezoelectric resonator 20.1 of the second chemical monitor 190, by displacing the bound Hg with Na, wherein the frequency difference of the second chemical monitor 190 will the indicate when the associated refresh process is complete.

A relatively high concentration of NaCl will displace Hg or As(III) despite the fact that Na is far below Hg on the selectivity sequence. If Hg is >8× more preferred than Na, they will reach chemical equilibrium when the concentration of Na is 8× that of Hg.

Otherwise, from step (2404), if neither anions or cations are to be filtered, then, in step (2422), the mechanically filtered sample fluid 14 is discharged from the preconditioner 2500 as the associated preconditioned sample fluid 14'.

The preconditioner 2500 may also include a granular activated carbon column—for example, in silver form to inhibit growth of bacteria—to remove organic molecules, upstream of the anion 176, 176' or cation filters.

Figure 27:
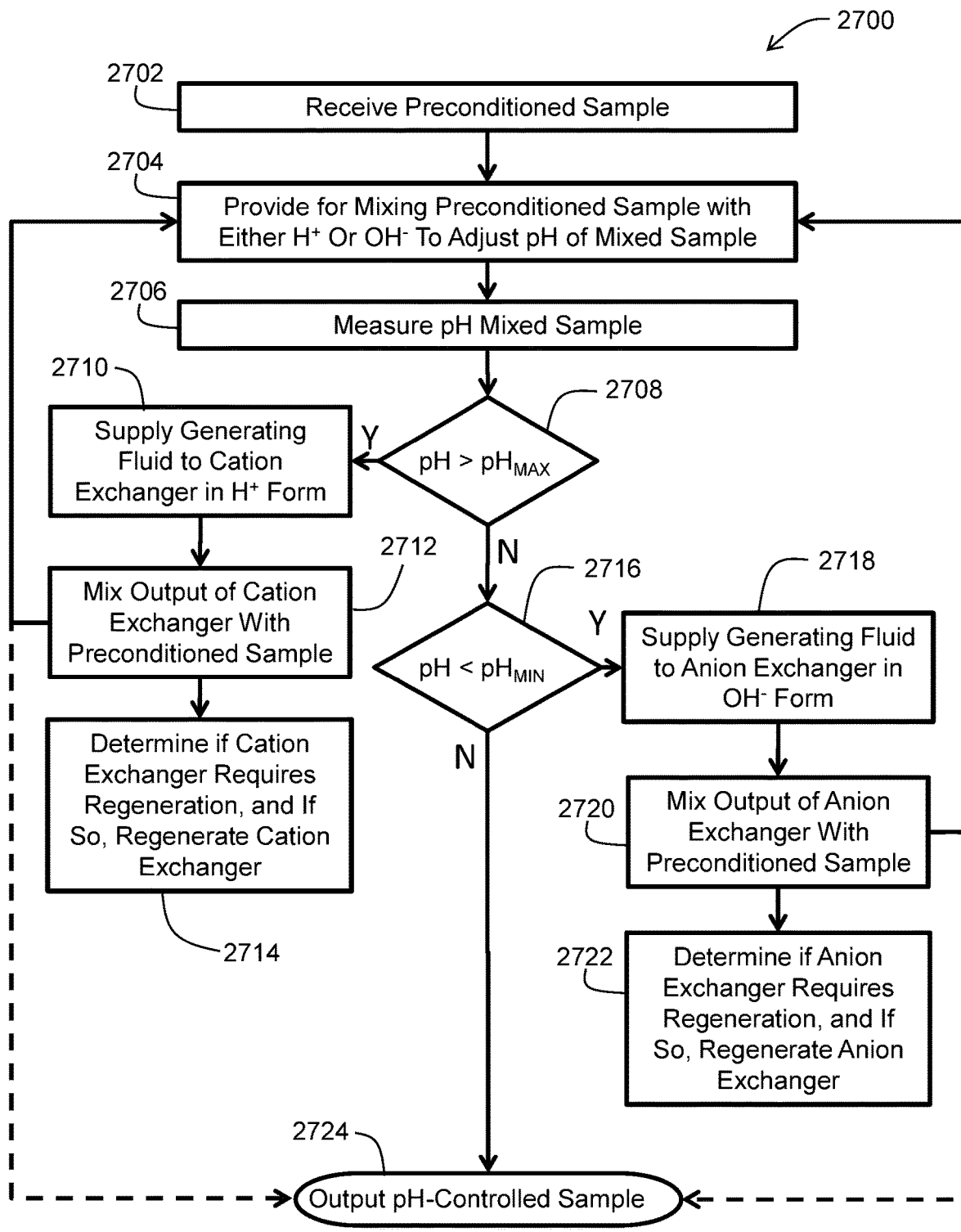
FIG. 27 illustrates a flow chart of a pH measurement and control process of an associated pH measurement and control system of the associated fluid contaminant sensing system, and associated process, illustrated in FIGS. 19-21.
Figure 28:
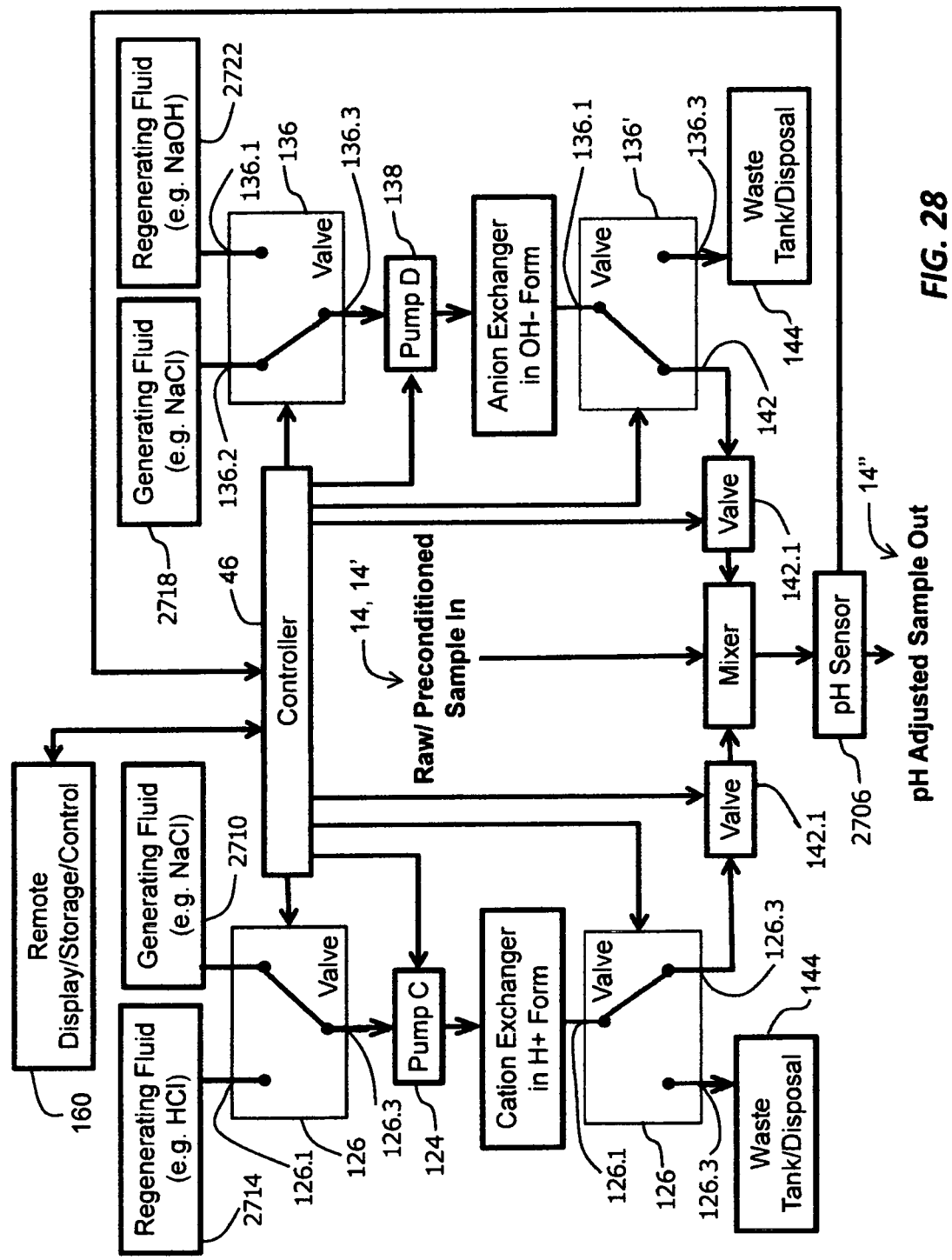
FIG. 28 illustrates block diagram of the pH measurement and control system illustrated in FIGS. 20 and 21, during operation of the associated continuous sensing process illustrated in FIG. 19.
Figure 29:
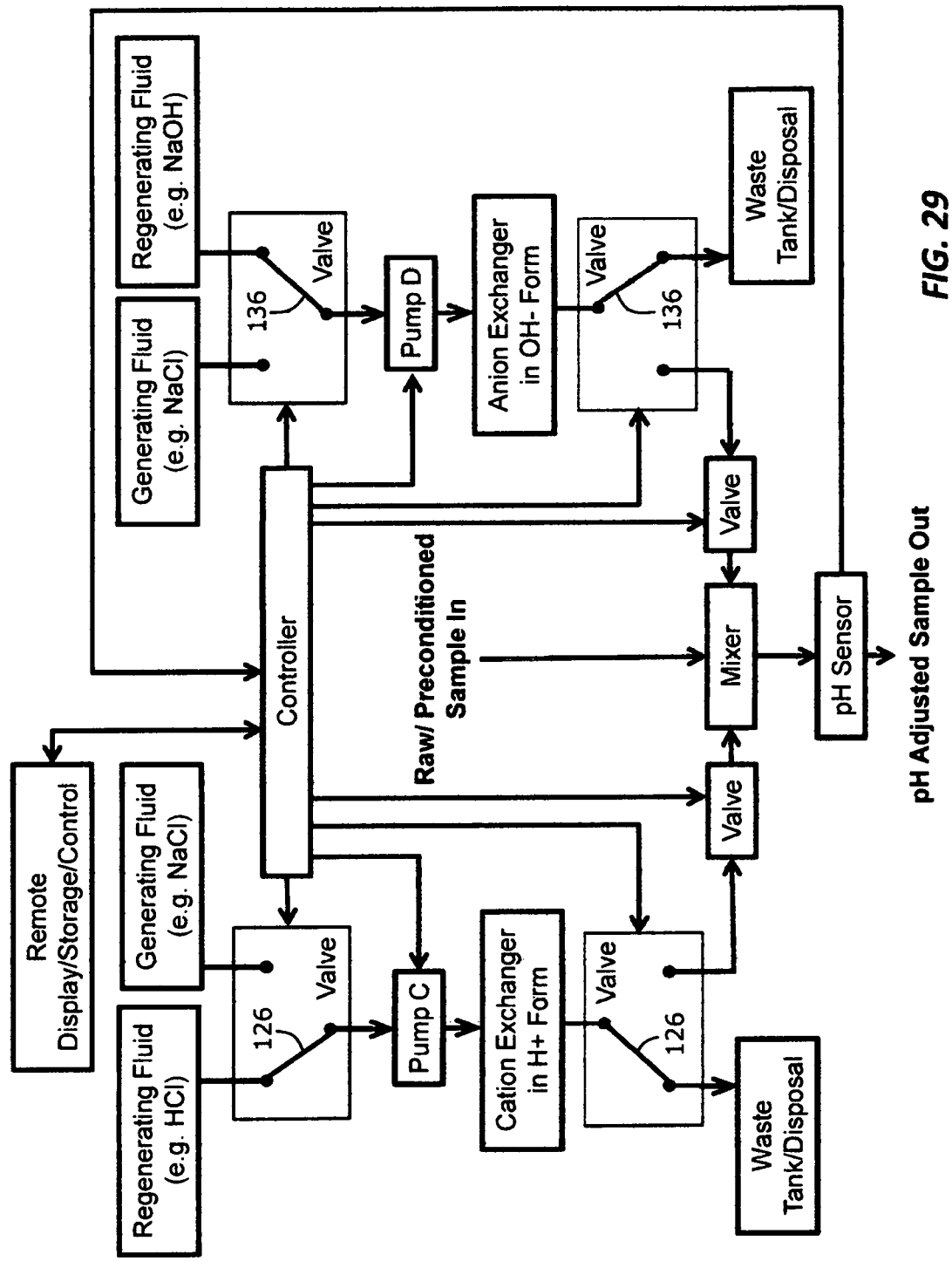
FIG. 29 illustrates a block diagram of the pH measurement and control system illustrated in FIG. 28, during an associated process for refreshing an associated anion exchanger, or during an associated process for refreshing an associated cation exchanger.

FIG. 27 illustrates a flow chart of a pH measurement and control process of an associated pH measurement and control system of the associated fluid contaminant sensing system, and associated process, illustrated in FIGS. 19-21;

FIG. 28 illustrates block diagram of the pH measurement and control system illustrated in FIGS. 20 and 21, during operation of the associated continuous sensing process illustrated in FIG. 19;

FIG. 29 illustrates a block diagram of the pH measurement and control system illustrated in FIG. 28, during an associated process for refreshing an associated anion exchanger, or during an associated process for refreshing an associated cation exchanger;

In one set of embodiments, the fluid contaminant sensing system 10 is configured to operate in a default pH range of 6.5-8.5, which is consistent with US tap water. Configuration in this sense means that the receptors will are designed to capture the targets in that range, and the separations will perform in that range. In monitor applications such as some industrial applications with pH's of the sample flow outside the default range, then the receptors and separations are designed accordingly.

In the event that the pH of the sample flow changes and moves out of the targeted range, then the associated pH control system adjust the pH of the sample flow and restore it to the target range.

As shown in FIGS. 27-20, in one embodiment, pH adjustment columns are employed to either raise or lower pH.

A continuous flow pH measurement device is employed upstream from the monitor. For pH measurement, from Cole Parmer, a Honeywell Directline pH Transmitter Electronics Module, EW56611-60 using a pH electrode EW-56611-62 can be employed.

In one embodiment, pH adjustment columns are employed to either raise or lower pH. The columns are connected to tubing that feeds into the sensor sample flow line. In one embodiment, the adjustment columns are a cation exchanger in the $H^+$ form and an anion exchanger in the $OH^-$ form.

The pH measurements readings are recorded in the CCM. When the pH readings are outside the sensor range, the CCM will trigger microvalves preceding the upstream cation or anion columns as described below.

When the pH measurement device indicates the pH is higher than desired for a particular sensor, a solution of NaCl is passed through the cation column, releasing $H^+$ ions into the sample flow, lowering the pH. The cation column is regenerated by passing HCl through the column and directing the effluent to a disposal container.

When the upstream pH measurement device indicates the pH is lower than desired for a particular sensor, a solution of NaCl is passed through the anion column, releasing $OH^-$ ions into the sample flow, increasing the pH. The anion exchanger is regenerated by passing NaOH through the column and directing the effluent to a disposal container.

Figure 30:
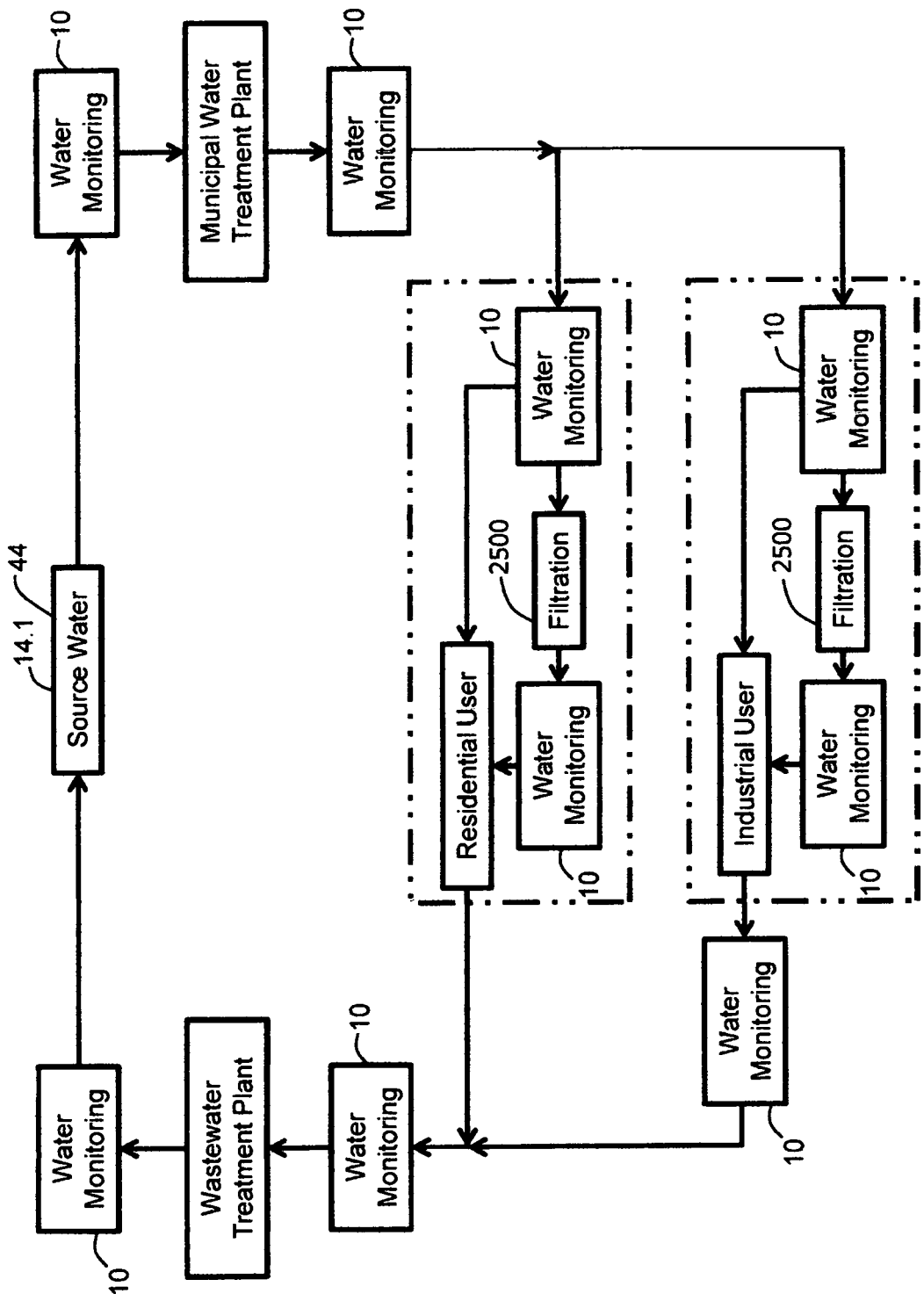
FIG. 30 illustrates block diagram of a water cycle illustrating prospective applications for the fluid contaminant sensing system to monitor the associated water system at various stages of the water cycle.

FIG. 30 illustrates block diagram of a water cycle illustrating prospective applications for the fluid contaminant sensing system to monitor the associated water system at various stages of the water cycle.

Accordingly, depending upon the configuration, and the particular type of adsorption material 34' used on the third electrode 30 of the associated reference piezoelectric resonator 20.2, the fluid contaminant sensing system 10 can provide for sensing target ions, molecules, inorganic or organic chemicals or microorganisms, in environments ranging from ultra-pure water systems to befouled waters. The fluid contaminant sensing system 10 provides for substantially unattended continuous flow sensing, or for use as a portable sampler and sensor, The results of the fluid contaminant sensing system 10 can be displayed locally, or transmitted to a location that is remote in relation to the associated sample fluid 14 and the fluid contaminant sensor cell 54 and associated physical hardware.

Notwithstanding that the above-illustrated embodiments incorporate quartz-crystal piezoelectric resonators 20, it should be understood that other types of piezoelectric material may also be used, including, but not limited to lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, dipotassium tartrate, or PZT (lead zirconate titanate). An oscillator crystal can be also manufactured by depositing the resonator material on the silicon chip surface. Crystals of gallium phosphate, langasite, langanite and langanate are about 10 times more pullable than the corresponding quartz crystals, and are used in some VCXO (voltage controlled crystal oscillators) oscillators. Other VCXO materials that could be used include AIPO4, GaPO4, langasite La3Ga5NbO14 Lanthanum gallium niobate and langanite and langatate. In addition to its piezoelectric effect and the ability to operate as a controlled frequency resonator based upon its physical dimensions, the piezoelectric resonators 20 also provide sufficient strength to contain the fluid within the associated first 38 or second 40 cavity of the fluid contaminant sensor cell 54.

Notwithstanding that the third electrode 30 of the reference piezoelectric resonator 20.2 in the above-illustrated embodiments incorporate an adsorption layer 34.2 of adsorption material 34' for which the associated chemical receptors are blocked with a blocking substance 36' in an overlaying blocking layer 36—provide for the third electrode 30 of the reference piezoelectric resonator 20.2 to be configured as close as possible to the first electrode 26 of the active piezoelectric resonator 20.1, which provides for minimizing the effects of ionic strength, viscosity and other common-mode effects, —it should be understood that, depending upon the nature of the sample fluid 14 and the nature of the target analyte 12, that a blocked adsorption layer 34.2 is not essential, and that in some cases, the third electrode 30 of the reference piezoelectric resonator 20.2 could be either uncoated, or coated with a different substance, for example, TEFLON® or a TEFLON®-like substance.

While specific embodiments have been described in detail in the foregoing detailed description and illustrated in the accompanying drawings, those with ordinary skill in the art will appreciate that various modifications and alternatives to those details could be developed in light of the overall teachings of the disclosure. It should be understood, that any reference herein to the term "or" is intended to mean an "inclusive or" or what is also known as a "logical OR", wherein when used as a logic statement, the expression "A or B" is true if either A or B is true, or if both A and B are true, and when used as a list of elements, the expression "A, B or C" is intended to include all combinations of the elements recited in the expression, for example, any of the elements selected from the group consisting of A, B, C, (A, B), (A, C), (B, C), and (A, B, C); and so on if additional elements are listed. Furthermore, it should also be understood that the indefinite articles "a" or "an", and the corresponding associated definite articles "the' or "said", are each intended to mean one or more unless otherwise stated, implied, or physically impossible. Yet further, it should be understood that the expressions "at least one of A and B, etc.", "at least one of A or B, etc.", "selected from A and B, etc." and "selected from A or B, etc." are each intended to mean either any recited element individually or any combination of two or more elements, for example, any of the elements from the group consisting of "A", "B", and "A AND B together", etc. Yet further, it should be understood that the expressions "one of A and B, etc." and "one of A or B, etc." are each intended to mean any of the recited elements individually alone, for example, either A alone or B alone, etc., but not A AND B together. Furthermore, it should also be understood that unless indicated otherwise or unless physically impossible, that the above-described embodiments and aspects can be used in combination with one another and are not mutually exclusive. Accordingly, the particular arrangements disclosed are meant to be illustrative only and not limiting as to the scope of the invention, which is to be given the full breadth of the appended claims, and any and all equivalents thereof.

What is claimed is:

1. A method of sensing a substance in a sample fluid, comprising:
   a. automatically resonating a first piezoelectric resonator associated with a first cavity, wherein said first piezoelectric resonator comprises:
      i. a first portion of piezoelectric material, wherein said first portion of piezoelectric material has opposing first and second surfaces spanning a thickness of said first portion of piezoelectric material, and a lateral extent of said first portion of piezoelectric material underlying said first and second surfaces is substantially greater than said thickness of said first portion of piezoelectric material;
      ii. a first electrode on said first surface of said first portion of piezoelectric material, wherein a first side of said first electrode is attached to said first surface of said first portion of piezoelectric material, a second side of said first electrode is exposed to a first fluid in said first cavity, and said second side of said first electrode incorporates a coating that provides for preferentially adsorbing the substance if said substance is contained in said first fluid; and
      iii. a second electrode on said second surface of said first portion of piezoelectric material, wherein a first side of said second electrode is attached to said second surface of said first portion of piezoelectric material, and the operation of automatically resonating said first piezoelectric resonator comprises applying a first time-varying voltage across said first and second electrodes at a first frequency sufficient to cause said first portion of piezoelectric material to mechanically resonate;
   b. automatically resonating a second piezoelectric resonator associated with a second cavity, wherein said second cavity is distinct from said first cavity, and said second piezoelectric resonator comprises:
      i. a second portion of piezoelectric material, wherein said piezoelectric material of said second portion of piezoelectric material is either distinct from, or continuous with, said piezoelectric material of said first portion of piezoelectric material, said second portion of piezoelectric material has opposing third and fourth surfaces spanning a thickness of said second portion of piezoelectric material, and a lateral extent of said second portion of piezoelectric material underlying said third and fourth surfaces is substantially greater than said thickness of said second portion of piezoelectric material;
ii. a third electrode on said third surface of said second portion of piezoelectric material, wherein a first side of said third electrode is attached to said third surface of said second portion of piezoelectric material, and a second side of said third electrode is exposed to a second fluid in said second cavity; and
iii. a fourth electrode on said fourth surface of said second portion of piezoelectric material, wherein a first side of said fourth electrode is attached to said fourth surface of said second portion of piezoelectric material, and the operation of automatically resonating said second piezoelectric resonator comprises applying a second time-varying voltage across said third and fourth electrodes at a second frequency sufficient to cause said second portion of piezoelectric material to mechanically resonate, wherein a frequency difference by which said second frequency differs from said first frequency is responsive to an amount of said substance adsorbed by said coating on said second side of said first electrode of said first portion of piezoelectric material of said first piezoelectric resonator;
c. automatically commencing or continuing a sampling process, wherein said sampling process comprises:
i. automatically pumping the sample fluid as said first fluid through said first cavity and detecting said first frequency responsive thereto; and
ii. automatically pumping said sample fluid as said second fluid through said second cavity and detecting said second frequency responsive thereto;
d. continuing with said sampling process until a change in said frequency difference, by which said second frequency differs from said first frequency during said sampling process, relative to an initial frequency difference, crosses a first threshold, then automatically interrupting said sampling process and automatically commencing a refresh process to provide for refreshing said coating incorporated on said second side of said first electrode, wherein said refresh process comprises:
i. automatically pumping a regeneration fluid as said first fluid through said first cavity, and detecting said first frequency responsive thereto;
ii. automatically pumping a neutral fluid as said second fluid through said second cavity, and detecting said second frequency responsive thereto;
e. continuing said refresh process until said change in said frequency difference, by which said second frequency differs from said first frequency during said refresh process, crosses a second threshold; and
f. automatically terminating said refresh process, and automatically resuming said sampling process at step c.

2. A method of sensing a substance in a sample fluid as recited in claim 1, further comprising:
a. automatically commencing a rinse process after completion of step e of claim 1 and prior to commencement of step f of claim 1, wherein said rinse process comprises:
i. automatically pumping said neutral fluid as said first fluid through said first cavity, and detecting said first frequency responsive thereto;
ii. automatically pumping said neutral fluid as said second fluid through said second cavity, and detecting said second frequency responsive thereto; and b. continuing said rinse process until a change, over a period of time, of said change in said frequency difference, by which said second frequency differs from said first frequency during said rinse process, crosses a third threshold, then automatically terminating said rinse and refresh processes.

3. A method of sensing a substance in a sample fluid as recited in claim 1, wherein said second side of said first electrode incorporates said coating that, without modification thereof, would provide for preferentially adsorbing said substance if contained in said second fluid, and said coating is modified so as to substantially prevent said substance from being adsorbed thereby if said substance is contained in said second fluid.

4. A method of sensing a substance in a sample fluid as recited in claim 1, wherein said first portion of piezoelectric material and said second portion of piezoelectric material are different, distinct and non-overlapping portions of, or from, an integral piece of said piezoelectric material, said first surface of said first portion of piezoelectric material is continuous with said third surface of said second portion of piezoelectric material, and said second surface of said first portion of piezoelectric material is continuous with said fourth surface of said second portion of piezoelectric material.

5. A method of sensing a substance in a sample fluid as recited in claim 1, wherein said piezoelectric material of said first portion of piezoelectric material is distinct from said piezoelectric material of said second portion of piezoelectric material so that said first and second portions of piezoelectric material are discontinuous with respect to one another.

6. A method of sensing a substance in a sample fluid as recited in claim 1, wherein said piezoelectric material of said first portion of piezoelectric material comprises an AT-cut quartz crystal, and said piezoelectric material of said second portion of piezoelectric material comprises either a second, distinct portion of said AT-cut quartz crystal, or a different AT-cut quartz crystal.

7. A method of sensing a substance in a sample fluid as recited in claim 1, wherein said first piezoelectric resonator is part of a corresponding first quartz-crystal microbalance (QCM), and said second piezoelectric resonator is part of a corresponding second quartz-crystal microbalance (QCM).

8. A method of sensing a substance in a sample fluid as recited in claim 1, wherein said first and second electrodes constitute a first pair of electrodes, said third and fourth electrodes constituting a second pair of electrodes, and said first pair of electrodes is distinct from said second pair of electrodes.

9. A method of sensing a substance in a sample fluid as recited in claim 1, wherein said second and fourth electrodes are either interconnected with one another or are different portions of a corresponding continuous electrode.

10. A method of sensing a substance in a sample fluid as recited in claim 1, wherein said first and second piezoelectric resonators are resonated by said corresponding first and second time-varying voltages during mutually-exclusive, alternating periods of time.

11. A method of sensing a substance in a sample fluid as recited in claim 10, further comprising switching a shared resonator drive and measurement circuit between said first and second piezoelectric resonators so as to provide for applying said first time-varying voltage to said first and second electrodes, and applying said second time-varying voltage to said third and fourth electrodes, during said mutually-exclusive, alternating periods of time.

12. A method of sensing a substance in a sample fluid as recited in claim 1, wherein said first time-varying voltage is generated by a first resonator drive circuit, said second time-varying voltage is generated by a second resonator drive circuit, and said first resonator drive circuit is distinct from said second resonator drive circuit.

13. A method of sensing a substance in a sample fluid as recited in claim 1, wherein said sample fluid comprises water, said substance is selected from the group consisting of lead, mercury, cadmium and arsenite, said regeneration fluid comprises hydrochloric acid if said substance is either lead, mercury or cadmium, and said regeneration fluid comprises sodium hydroxide if said substance is arsenite.

14. A method of sensing a substance in a sample fluid as recited in claim 1, further comprising:
   a. calculating an amount of said substance adsorbed on said second side of said first electrode responsive to said change in said frequency difference and responsive to stored calibration data; and
   b. calculating a total amount or volume of said sample fluid responsive to a duration of time over which said sample fluid was pumped through said first cavity.

15. A method of sensing a substance in a sample fluid as recited in claim 1, further comprising mechanically filtering said sample fluid prior to the operation of pumping said sample fluid through said first cavity and prior to the operation of pumping said sample fluid through said second cavity.

16. A method of sensing a substance in a sample fluid as recited in claim 1, further comprising at least one of:
   a. filtering at least one anion from said sample fluid with an anion exchanger in chloride form prior to the operation of pumping said sample fluid through said first cavity; or
   b. filtering at least one cation from said sample fluid with a cation exchanger in sodium form prior to the operation of pumping said sample fluid through said first cavity.

17. A method of sensing a substance in a sample fluid as recited in claim 16, further comprising:
   a. monitoring said sample fluid following at least of the operation of filtering at least one anion or the operation of filtering at least one cation to detect either a breakthrough of said anion exchanger or a breakthrough of said cation exchanger;
   b. if said breakthrough of said anion exchanger is detected, then pumping a first regenerating fluid through said anion exchanger so as to provide for regenerating said anion exchanger; and
   c. if said breakthrough of said cation exchanger is detected, then pumping a second regenerating fluid through said cation exchanger so as to provide for regenerating said cation exchanger.

18. A method of sensing a substance in a sample fluid as recited in claim 1, further comprising monitoring and controlling a pH of said sample fluid prior to the operation of pumping said sample fluid through said first cavity, wherein the operation of controlling said pH of said sample fluid comprises at least one of:
   a. if said pH of said sample fluid is greater than a first threshold, then pumping a first generating fluid through a cation exchanger and mixing an output therefrom with said sample fluid, wherein said cation exchanger is in H+ form; or
   b. if said pH of said sample fluid crosses a second threshold, then pumping a second generating fluid through an anion exchanger and mixing an output therefrom with said sample fluid, wherein said anion exchanger is in OH− form, wherein said first and second generating fluids are either the same type of fluid or are different types of fluids.

19. A method of sensing a substance in a sample fluid as recited in claim 1, further comprising communicating with a remote monitor or control device via a wired or wireless communication link using either a direct or networked connection so as to provide for transmitting either sensed, intermediate or error condition data to said remote monitor or control device, or so as to provide for receiving either data or commands from said remote monitor or control device.

20. A method of sensing a substance in a sample fluid as recited in claim 1, wherein said neutral fluid is deionized water.

21. A method of sensing a substance in a sample fluid as recited in claim 1, wherein the operation of pumping said sample fluid through said first cavity comprises pumping said sample fluid with a positive displacement pump so that a volume or amount of said sample fluid pumped through said first cavity can be determined responsive to a period of time over which said sample fluid is pumped.

22. A method of sensing a substance in a sample fluid as recited in claim 21, further comprising:
   a. measuring a temperature of said sample fluid; and
   b. either adjusting a flow rate of said positive displacement pump so as to provide for normalizing the flow rate of said sample fluid with respect to said temperature or accounting for an effect of said temperature on a calculation of a flow of said sample fluid through said first cavity.

23. A method of sensing a substance in a sample fluid as recited in claim 1, wherein said refresh process further comprises:
   a. prior to the operation of pumping said regeneration fluid, automatically pumping said neutral fluid through said second cavity and measuring a first flow rate of said neutral fluid pumped through said second cavity; and
   b. performing the operation of automatically pumping said regeneration fluid through said first cavity at a second flow rate that is substantially the same as said first flow rate.

24. A system for sensing a substance in a sample fluid, comprising:
   a. a first sensor, wherein said first sensor comprises a first piezoelectric resonator, and said first piezoelectric resonator comprises:
      i. a first portion of piezoelectric material, wherein said first portion of piezoelectric material has opposing first and second surfaces spanning a thickness of said first portion of piezoelectric material, and a lateral extent of said first portion of piezoelectric material underlying said first and second surfaces is substantially greater than said thickness of said first portion of piezoelectric material;
      ii. a first electrode on said first surface of said first portion of piezoelectric material, wherein a first side of said first electrode is attached to said first surface of said first portion of piezoelectric material;
      iii. a second electrode on said second surface of said first portion of piezoelectric material, wherein a first side of said second electrode is attached to said second surface of said first portion of piezoelectric material; and
      iv. a first cavity, wherein said first cavity cooperates with a first inlet and a first outlet, said first cavity is closed except at said first inlet and said first outlet, a second side of said first electrode is exposed to a first fluid in said first cavity, and said second side of said first electrode incorporates a coating that provides for preferentially adsorbing the substance to be detected if said substance is contained in said first fluid, and said first cavity is bounded in part by said first surface of said first portion of piezoelectric material or by the coated first electrode thereon;

b. a second sensor, wherein said second sensor comprises a second piezoelectric resonator, and said second piezoelectric resonator comprises:

i. a second portion of piezoelectric material, wherein said piezoelectric material of said second portion of piezoelectric material is either distinct from, or continuous with, said piezoelectric material of said first portion of piezoelectric material, said second portion of piezoelectric material has opposing third and fourth surfaces spanning a thickness of said second portion of piezoelectric material, and a lateral extent of said second portion of piezoelectric material underlying said third and fourth surfaces is substantially greater than said thickness of said second portion of piezoelectric material;

ii. a third electrode on said third surface of said second portion of piezoelectric material, wherein a first side of said third electrode is attached to said third surface of said second portion of piezoelectric material;

iii. a fourth electrode on said fourth surface of said second portion of piezoelectric material, wherein a first side of said fourth electrode is attached to said fourth surface of said second portion of piezoelectric material; and iv. a second cavity, wherein said second cavity cooperates with a second inlet and a second outlet, said second cavity is closed except at said second inlet and said second outlet, a second side of said third electrode is exposed to a second fluid in said second cavity, and said second cavity is bounded in part by said third surface of said second portion of piezoelectric material or by said third electrode thereon;

c. at least one piezoelectric resonator drive circuit, wherein each piezoelectric resonator drive circuit of said at least one piezoelectric resonator drive circuit comprises:

i. an oscillator driver to which at least one of said first and second piezoelectric resonators is connected, wherein at any given time, one of said first and second piezoelectric resonators provides for controlling a frequency of oscillation of said oscillator driver so as to oscillate at a resonant frequency of said one of said first and second piezoelectric resonators; and ii. a frequency detector for determining a magnitude of said frequency of oscillation;

d. a controller operatively coupled to said at least one piezoelectric resonator drive circuit, wherein said controller provides for determining at least one measure of, or responsive to, a mass of said substance adsorbed on said second side of said first electrode, responsive to a change in frequency difference relative to an initial frequency difference, wherein said change in said frequency difference is responsive to an amount by which a second frequency corresponding to said frequency of oscillation of said second piezoelectric resonator differs from a first frequency corresponding to said frequency of oscillation of said first piezoelectric resonator;

e. a source of neutral fluid, wherein said neutral fluid, when in said first cavity, has substantially no effect on said substance if said substance has been adsorbed by said coating on said second side of said first electrode;

f. a first controllable valve under control of said controller, wherein said first controllable valve can operate in either of two mutually-exclusive states under control of said controller, and said first controllable valve comprises:

i. first and second inlets, and ii. an outlet, wherein in a first operating state, said outlet of said first controllable valve is in fluid communication with said second inlet which is in fluid communication with a source of the sample fluid, in a second operating state, said outlet of said first controllable valve is in fluid communication with said first inlet which is in fluid communication with said source of neutral fluid;

g. a first pump, wherein said first pump is a positive displacement pump under control of said controller, an inlet of said first pump is in fluid communication with said outlet of said first controllable valve, and an outlet of said first pump is operatively coupled to said first inlet of said first cavity, and said outlet of said first pump is operatively coupled to said second inlet of said second cavity;

h. a source of regeneration fluid, wherein said regeneration fluid provides for removing said substance adsorbed by said coating on said second side of said first electrode when said regeneration fluid is pumped into said first cavity;

i. a second pump, wherein said second pump is under control of said controller, an inlet of said second pump is in fluid communication with said source of regeneration fluid, and an outlet of said second pump is operatively coupled to said first inlet of said first cavity;

j. at least one second valve, wherein said at least one second valve provides for selectively and mutually-exclusively coupling said outlet of said first pump and said outlet of said second pump to said first inlet of said first cavity;

k. wherein in a first mode of operation, said controller provides for automatically operating said first controllable valve in said first operating state, and provides for automatically operating said first pump, so as to provide for pumping said sample fluid through said first cavity and through said second cavity, either at the same time or during alternate time periods; during said first mode of operation, said controller provides for comparing said change in said frequency difference with a first threshold, and if said change in said frequency difference crosses said first threshold, said controller provides for automatically switching to a second mode of operation;

l. in said second mode of operation, said controller provides for automatically operating said first controllable valve in said second operating state, provides for automatically operating said first pump, and provides for automatically operating said second pump, so as to provide for pumping said regeneration fluid through said first cavity, and so as to provide for pumping said neutral fluid through said second cavity; during said second mode of operation, said controller provides for comparing said change in said frequency difference with a second threshold, and if said change in said frequency difference does not cross said second threshold, said controller provides for automatically terminating said second mode of operation; and m. said controller provides for automatically resuming said first mode of operation after terminating said second mode of operation.

25. A system for sensing a substance in a sample fluid as recited in claim 24, wherein during said second mode of operation, if said change in said frequency difference does not cross said second threshold, said controller provides for automatically switching to a third mode of operation, wherein in said third mode of operation, said controller provides for automatically operating said first controllable valve in said second operating state, provides for automatically operating said first pump, and provides for automatically terminating operation of said second pump, so as to provide for pumping said neutral fluid through said first cavity and through said second cavity, either at the same time or during alternate time periods; during said third mode of operation, said controller provides for comparing a variation of said change in said frequency difference over time with a third threshold, and if said variation of said change in said frequency difference over time does not cross said third threshold, said controller provides for automatically resuming said first mode of operation.

26. A system for sensing a substance in a sample fluid as recited in claim 24, wherein said second side of said first electrode incorporates said coating that, without modification thereof, would provide for preferentially adsorbing the substance if contained in said first fluid, said coating is modified so as to substantially prevent said substance from being adsorbed thereby if said substance is contained in said second fluid, and said second cavity is bounded in part by said third surface of said second portion of piezoelectric material or by the coated third electrode thereon.

27. A system for sensing a substance in a sample fluid as recited in claim 24, wherein said first portion of piezoelectric material and said second portion of piezoelectric material are different, distinct and non-overlapping portions of, or from, an integral piece of said piezoelectric material, said first surface of said first portion of piezoelectric material is continuous with said third surface of said second portion of piezoelectric material, and said second surface of said first portion of piezoelectric material is continuous with said fourth surface of said second portion of piezoelectric material.

28. A system for sensing a substance in a sample fluid as recited in claim 24, wherein said piezoelectric material of said first portion of piezoelectric material is distinct from said piezoelectric material of said second portion of piezoelectric material so that said first and second portions of piezoelectric material are discontinuous with respect to one another.

29. A system for sensing a substance in a sample fluid as recited in claim 24, wherein said piezoelectric material of said first portion of piezoelectric material comprises an AT-cut quartz crystal, and said piezoelectric material of said second portion of piezoelectric material comprises either a second, distinct portion of said AT-cut quartz crystal, or a different AT-cut quartz crystal.

30. A system for sensing a substance in a sample fluid as recited in claim 29, wherein said first piezoelectric resonator is part of a corresponding first quartz-crystal microbalance (QCM), and said second piezoelectric resonator is part of a corresponding second quartz-crystal microbalance (QCM).

31. A system for sensing a substance in a sample fluid as recited in claim 24, wherein said first and second electrodes constitute a first pair of electrodes, said third and fourth electrodes constituting a second pair of electrodes, and said first pair of electrodes is distinct from said second pair of electrodes.

32. A system for sensing a substance in a sample fluid as recited in claim 24, wherein said second and fourth electrodes are either interconnected with one another or are different portions of a corresponding continuous electrode.

33. A system for sensing a substance in a sample fluid as recited in claim 24, wherein said first and second piezoelectric resonators are resonated by said at least one piezoelectric resonator drive circuit during mutually-exclusive, alternating periods of time.

34. A system for sensing a substance in a sample fluid as recited in claim 33, wherein said at least one piezoelectric resonator drive circuit comprises a single piezoelectric resonator drive circuit that is shared between said first and second piezoelectric resonators, further comprising at least one switch operatively coupling said single piezoelectric resonator drive circuit to said first and second piezoelectric resonators, wherein in a first operating state of said at least one switch, said single piezoelectric resonator drive circuit is operatively coupled to said first piezoelectric resonator, and in a second operating state of said at least one switch, said single piezoelectric resonator drive circuit is operatively coupled to said second piezoelectric resonator.

35. A system for sensing a substance in a sample fluid as recited in claim 24, wherein said at least one piezoelectric resonator drive circuit comprises distinct first and second piezoelectric resonator drive circuits, said first piezoelectric resonator drive circuit is operatively coupled to said first piezoelectric resonator, and said second piezoelectric resonator drive circuit is operatively coupled to said second piezoelectric resonator.

36. A system for sensing a substance in a sample fluid as recited in claim 24, wherein said sample fluid comprises water, said substance is selected from the group consisting of lead, mercury, cadmium and arsenite, said regeneration fluid comprises hydrochloric acid if said substance is either lead, mercury or cadmium, and said regeneration fluid comprises sodium hydroxide if said substance is arsenite.

37. A system for sensing a substance in a sample fluid as recited in claim 24, wherein said controller provides for:
a. calculating an amount of said substance adsorbed on said second side of said first electrode responsive to said change in said frequency difference and responsive to stored calibration data; and
b. calculating a total amount or volume of said sample fluid responsive to a duration of time over which said sample fluid was pumped through said first cavity.

38. A system for sensing a substance in a sample fluid as recited in claim 24, further comprising at least one filter upstream of said first pump configured to remove other substances that might otherwise adsorb to said coated first electrode.

39. A system for sensing a substance in a sample fluid as recited in claim 24, further comprising at least one of:
a. an anion exchange filter in chloride form upstream of said first pump; or
b. a cation exchange filter in sodium form upstream of said first pump.

40. A system for sensing a substance in a sample fluid as recited in claim 39, further comprising:
a at least one chemical monitor downstream of a corresponding at least one of said anion exchange filter or said cation exchange filter, wherein said at least one chemical monitor provides for detecting a breakthrough of a corresponding at least one of said anion exchange filter or said cation exchange filter;
b. at least one source of regeneration fluid;
c. at least one controllable valve operatively coupling said at least one source of regeneration fluid to a corresponding at least one of said anion exchange filter or said cation exchange filter; and
d. at least one pump operatively coupling said at least one source of regeneration fluid to a corresponding said at least one controllable valve, wherein said controller or a separate controller operatively coupling said at least one chemical monitor to said at least one controllable valve, provides for controlling said at least one pump and said at least one controllable valve responsive to a corresponding output of said at least one chemical monitor.

41. A system for sensing a substance in a sample fluid as recited in claim 24, further comprising a pH monitoring and control system upstream of said first pump, wherein said pH monitoring and control system comprises:
a. at least one of a cation exchanger and an anion exchanger;
b. at least one source of generating fluid;
c. at least one pump operatively coupling said at least one source of generating fluid to a corresponding at least one of an input port of said cation exchanger or an input port of said anion exchanger, wherein at least one output port of said cation exchanger or said anion exchanger is in fluid communication with said inlet of said first pump.

42. A system for sensing a substance in a sample fluid as recited in claim 24, wherein said controller provides for communicating with a remote monitor or control device via a wired or wireless communication link using either a direct or networked connection so as to provide for transmitting either sensed, intermediate or error condition data to said remote monitor or control device, or so as to provide for receiving either data or commands from said remote monitor or control device.

43. A system for sensing a substance in a sample fluid as recited in claim 24, wherein said neutral fluid is deionized water.

44. A system for sensing a substance in a sample fluid as recited in claim 24, wherein said first pump comprises a positive displacement pump.

45. A system for sensing a substance in a sample fluid as recited in claim 44, further comprising a temperature sensor configured to generate a temperature signal responsive to a temperature of said sample fluid, wherein said temperature signal is operatively coupled to said controller, and either said controller provides for adjusting a flow rate of said positive displacement pump so as to normalize a flow rate of said sample fluid with respect to temperature, or said controller provides for accounting for an effect of said temperature on a calculation of a flow of said sample fluid through said first cavity.

46. A system for sensing a substance in a sample fluid as recited in claim 24, further comprising:
a. a first flow sensor for sensing a first rate of flow of said neutral fluid into said second cavity; and
b. a second flow sensor for sensing a second rate of flow of said regeneration fluid into said first cavity, wherein said controller provides for controlling at least one of said first and second pumps so that said second rate of flow is substantially equal to said first rate of flow during at least a portion of said second mode of operation.

47. A method of providing for sensing a substance in a sample fluid, comprising:
a. providing for automatically resonating a first piezoelectric resonator associated with a first cavity, wherein said first piezoelectric resonator comprises:
i. a first portion of piezoelectric material, wherein said first portion of piezoelectric material has opposing first and second surfaces spanning a thickness of said first portion of piezoelectric material, and a lateral extent of said first portion of piezoelectric material underlying said first and second surfaces is substantially greater than said thickness of said first portion of piezoelectric material;
ii. a first electrode on said first surface of said first portion of piezoelectric material, wherein a first side of said first electrode is attached to said first surface of said first portion of piezoelectric material, a second side of said first electrode is exposed to a first fluid in said first cavity, and said second side of said first electrode incorporates a coating that provides for preferentially adsorbing the substance if said substance is contained in said first fluid; and
iii. a second electrode on said second surface of said first portion of piezoelectric material, wherein a first side of said second electrode is attached to said second surface of said first portion of piezoelectric material, and the operation of providing for automatically resonating said first piezoelectric resonator comprises providing for applying a first time-varying voltage across said first and second electrodes at a first frequency sufficient to cause said first portion of piezoelectric material to mechanically resonate;
b. providing for automatically resonating a second piezoelectric resonator associated with a second cavity, wherein said second cavity is distinct from said first cavity, and said second piezoelectric resonator comprises:
i. a second portion of piezoelectric material, wherein said piezoelectric material of said second portion of piezoelectric material is either distinct from, or continuous with, said piezoelectric material of said first portion of piezoelectric material, said second portion of piezoelectric material has opposing third and fourth surfaces spanning a thickness of said second portion of piezoelectric material, and a lateral extent of said second portion of piezoelectric material underlying said third and fourth surfaces is substantially greater than said thickness of said second portion of piezoelectric material;
ii. a third electrode on said third surface of said second portion of piezoelectric material, wherein a first side of said third electrode is attached to said third surface of said second portion of piezoelectric material, and a second side of said third electrode is exposed to a second fluid in said second cavity; and
iii. a fourth electrode on said fourth surface of said second portion of piezoelectric material, wherein a first side of said fourth electrode is attached to said fourth surface of said second portion of piezoelectric material, and the operation of providing for automatically resonating said second piezoelectric resonator comprises providing for applying a second time-varying voltage across said third and fourth electrodes at a second frequency sufficient to cause said second portion of piezoelectric material to mechanically resonate, wherein a frequency difference by which said second frequency differs from said first frequency is responsive to an amount of said substance adsorbed by said coating on said second side of said first electrode of said first portion of piezoelectric material of said first piezoelectric resonator;

c. providing for automatically commencing or continuing a sampling process, wherein said sampling process comprises:
 i. automatically pumping the sample fluid as said first fluid through said first cavity and detecting said first frequency responsive thereto; and
 ii. automatically pumping said sample fluid as said second fluid through said second cavity and detecting said second frequency responsive thereto;

d. providing for continuing with said sampling process until a change in said frequency difference, by which said second frequency differs from said first frequency during said sampling process, relative to an initial frequency difference, crosses a first threshold, then providing for automatically interrupting said sampling process and providing for automatically commencing a refresh process to provide for refreshing said coating incorporated on said second side of said first electrode, wherein said refresh process comprises:
 i. automatically pumping a regeneration fluid as said first fluid through said first cavity, and detecting said first frequency responsive thereto;
 ii. automatically pumping a neutral fluid as said second fluid through said second cavity, and detecting said second frequency responsive thereto;

e. providing for continuing said refresh process until said change in said frequency difference, by which said second frequency differs from said first frequency during said refresh process, crosses a second threshold; and f. providing for automatically terminating said refresh process, and providing for automatically resuming said sampling process at step c.

48. A method of providing for sensing a substance in a sample fluid as recited in claim 47, further comprising:
a. providing for automatically commencing a rinse process after completion of step e of claim 47 and prior to commencement of step f of claim 47, wherein said rinse process comprises:
 i. automatically pumping said neutral fluid as said first fluid through said first cavity, and detecting said first frequency responsive thereto;
 ii. automatically pumping said neutral fluid as said second fluid through said second cavity, and detecting said second frequency responsive thereto; and
b. providing for continuing said rinse process until a change, over a period of time, of said change in said frequency difference, by which said second frequency differs from said first frequency during said rinse process, crosses a third threshold, then providing for automatically terminating said rinse and refresh processes.

49. A method of providing for sensing a substance in a sample fluid as recited in claim 47, wherein said second side of said first electrode incorporates said coating that, without modification thereof, would provide for preferentially adsorbing said substance if contained in said second fluid, and said coating is modified so as to substantially prevent said substance from being adsorbed thereby if said substance is contained in said second fluid.

50. A method of providing for sensing a substance in a sample fluid as recited in claim 47, wherein said first portion of piezoelectric material and said second portion of piezoelectric material are different, distinct and non-overlapping portions of, or from, an integral piece of said piezoelectric material, said first surface of said first portion of piezoelectric material is continuous with said third surface of said second portion of piezoelectric material, and said second surface of said first portion of piezoelectric material is continuous with said fourth surface of said second portion of piezoelectric material.

51. A method of providing for sensing a substance in a sample fluid as recited in claim 47, wherein said piezoelectric material of said first portion of piezoelectric material is distinct from said piezoelectric material of said second portion of piezoelectric material so that said first and second portions of piezoelectric material are discontinuous with respect to one another.

52. A method of providing for sensing a substance in a sample fluid as recited in claim 47, wherein said piezoelectric material of said first portion of piezoelectric material comprises an AT-cut quartz crystal, and said piezoelectric material of said second portion of piezoelectric material comprises either a second, distinct portion of said AT-cut quartz crystal, or a different AT-cut quartz crystal.

53. A method of providing for sensing a substance in a sample fluid as recited in claim 47, wherein said first piezoelectric resonator is part of a corresponding first quartz-crystal microbalance (QCM), and said second piezoelectric resonator is part of a corresponding second quartz-crystal microbalance (QCM).

54. A method of providing for sensing a substance in a sample fluid as recited in claim 47, wherein said first and second electrodes constitute a first pair of electrodes, said third and fourth electrodes constituting a second pair of electrodes, and said first pair of electrodes is distinct from said second pair of electrodes.

55. A method of providing for sensing a substance in a sample fluid as recited in claim 47, wherein said second and fourth electrodes are either interconnected with one another or are different portions of a corresponding continuous electrode.

56. A method of providing for sensing a substance in a sample fluid as recited in claim 47, wherein said first and second piezoelectric resonators are resonated by said corresponding first and second time-varying voltages during mutually-exclusive, alternating periods of time.

57. A method of providing for sensing a substance in a sample fluid as recited in claim 56, further comprising providing for switching a shared resonator drive and measurement circuit between said first and second piezoelectric resonators so as to provide for applying said first time-varying voltage to said first and second electrodes, and providing for applying said second time-varying voltage to said third and fourth electrodes, during said mutually-exclusive, alternating periods of time.

58. A method of providing for sensing a substance in a sample fluid as recited in claim 47, wherein said first time-varying voltage is generated by a first resonator drive circuit, said second time-varying voltage is generated by a second resonator drive circuit, and said first resonator drive circuit is distinct from said second resonator drive circuit.

59. A method of providing for sensing a substance in a sample fluid as recited in claim 47, wherein said sample fluid comprises water, said substance is selected from the group consisting of lead, mercury, cadmium and arsenite, said regeneration fluid comprises hydrochloric acid if said substance is either lead, mercury or cadmium, and said regeneration fluid comprises sodium hydroxide if said substance is arsenite.

60. A method of providing for sensing a substance in a sample fluid as recited in claim 47, further comprising:
   a. providing for calculating an amount of said substance adsorbed on said second side of said first electrode responsive to said change in said frequency difference and responsive to stored calibration data; and
   b. providing for calculating a total amount or volume of said sample fluid responsive to a duration of time over which said sample fluid was pumped through said first cavity.

61. A method of providing for sensing a substance in a sample fluid as recited in claim 47, further comprising providing for mechanically filtering said sample fluid prior to the operation of pumping said sample fluid through said first cavity and prior to the operation of pumping said sample fluid through said second cavity.

62. A method of providing for sensing a substance in a sample fluid as recited in claim 47, further comprising at least one of:
   a. providing for filtering at least one anion from said sample fluid with an anion exchanger in chloride form prior to the operation of pumping said sample fluid through said first cavity; or
   b. providing for filtering at least one cation from said sample fluid with a cation exchanger in sodium form prior to the operation of pumping said sample fluid through said first cavity.

63. A method of providing for sensing a substance in a sample fluid as recited in claim 62, further comprising:
   a. providing for monitoring said sample fluid following at least of the operation of filtering at least one anion or the operation of filtering at least one cation to detect either a breakthrough of said anion exchanger or a breakthrough of said cation exchanger;
   b. if said breakthrough of said anion exchanger is detected, then providing for pumping a first regenerating fluid through said anion exchanger so as to provide for regenerating said anion exchanger; and
   c. if said breakthrough of said cation exchanger is detected, then providing for pumping a second regenerating fluid through said cation exchanger so as to provide for regenerating said cation exchanger.

64. A method of providing for sensing a substance in a sample fluid as recited in claim 47, further comprising providing for monitoring and controlling a pH of said sample fluid prior to the operation of pumping said sample fluid through said first cavity, wherein the operation of controlling said pH of said sample fluid comprises at least one of:
   a. if said pH of said sample fluid is greater than a first threshold, then providing for pumping a first generating fluid through a cation exchanger and mixing an output therefrom with said sample fluid, wherein said cation exchanger is in H+ form; or
   b. if said pH of said sample fluid crosses a second threshold, then providing for pumping a second generating fluid through an anion exchanger and mixing an output therefrom with said sample fluid, wherein said anion exchanger is in OH– form, wherein said first and second generating fluids are either the same type of fluid or are different types of fluids.

65. A method of providing for sensing a substance in a sample fluid as recited in claim 47, further comprising providing for communicating with a remote monitor or control device via a wired or wireless communication link using either a direct or networked connection so as to provide for transmitting either sensed, intermediate or error condition data to said remote monitor or control device, or so as to provide for receiving either data or commands from said remote monitor or control device.

66. A method of providing for sensing a substance in a sample fluid as recited in claim 47, wherein said neutral fluid is deionized water.

67. A method of providing for sensing a substance in a sample fluid as recited in claim 47, wherein the operation of pumping said sample fluid through said first cavity comprises pumping said sample fluid with a positive displacement pump so that a volume or amount of said sample fluid pumped through said first cavity can be determined responsive to a period of time over which said sample fluid is pumped.

68. A method of providing for sensing a substance in a sample fluid as recited in claim 67, further comprising:
   a. providing for measuring a temperature of said sample fluid; and
   b. providing for either adjusting a flow rate of said positive displacement pump so as to provide for normalizing the flow rate of said sample fluid with respect to said temperature or accounting for an effect of said temperature on a calculation of a flow of said sample fluid through said first cavity.

69. A method of providing for sensing a substance in a sample fluid as recited in claim 47, wherein said refresh process further comprises:
   a. prior to the operation of pumping said regeneration fluid, providing for automatically pumping said neutral fluid through said second cavity and measuring a first flow rate of said neutral fluid pumped through said second cavity; and
   b. providing for performing the operation of automatically pumping said regeneration fluid through said first cavity at a second flow rate that is substantially the same as said first flow rate.

* * * * *